(12) United States Patent
Morin et al.

US006777203B1

(10) Patent No.: US 6,777,203 B1
(45) Date of Patent: *Aug. 17, 2004

(54) TELOMERASE PROMOTER DRIVING EXPRESSION OF THERAPEUTIC GENE SEQUENCES

(75) Inventors: Gregg B. Morin, Oakville (CA); Serge P. Lichtsteiner, Encinitas, CA (US); Alain P. Vasserot, Carlsbad, CA (US); Robert R. Adams, Redwood City, CA (US); William H. Andrews, Reno, NV (US)

(73) Assignee: Geron Corporation, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/244,438

(22) Filed: Feb. 4, 1999

Related U.S. Application Data

(63) Continuation-in-part of application No. 08/974,584, filed on Nov. 19, 1997, and a continuation-in-part of application No. 08/974,549, filed on Nov. 19, 1997, now Pat. No. 6,166,178.

(51) Int. Cl.[7] .......................... C12P 21/06; C12N 15/00
(52) U.S. Cl. .......................... 435/69.1; 435/455; 435/6; 435/320.1; 536/24.1
(58) Field of Search .............................. 435/320.1, 455, 435/69.1; 536/24.1

(56) References Cited

U.S. PATENT DOCUMENTS

| | | | |
|---|---|---|---|
| 5,416,017 A | 5/1995 | Burton et al. | 435/240.2 |
| 5,631,236 A | 5/1997 | Woo et al. | 514/44 |
| 5,728,379 A | 3/1998 | Martuza et al. | 424/93.2 |
| 5,907,083 A | 5/1999 | Robert et al. | 800/205 |
| 5,998,205 A | 12/1999 | Hallenbeck et al. | 435/325 |
| 6,054,575 A | 4/2000 | Villeponteau et al. | 536/24.31 |
| 6,093,809 A | 7/2000 | Cech et al. | 536/23.5 |
| 6,166,178 A * | 12/2000 | Cech | 530/324 |
| 6,228,643 B1 | 5/2001 | Greenland et al. | 435/419 |
| 6,274,790 B1 | 8/2001 | Kunst et al. | 800/287 |
| 6,281,409 B1 | 8/2001 | Woodhead et al. | 800/287 |
| 6,300,095 B1 | 10/2001 | Barredo Fuente et al. | 435/69.1 |
| 6,306,656 B1 | 10/2001 | Liu et al. | 435/419 |
| 6,331,527 B1 | 12/2001 | Parmacek et al. | 514/44 |
| 6,610,839 B1 | 8/2003 | Morin et al. | 536/24.1 |

FOREIGN PATENT DOCUMENTS

| | | | |
|---|---|---|---|
| GB | 2317891 | | 4/1998 |
| WO | WO 98/07838 | | 2/1998 |
| WO | WO 98/14592 | | 4/1998 |
| WO | WO 98/14593 | * | 4/1998 |
| WO | WO 98/21343 | | 5/1998 |
| WO | WO 98/37181 | | 8/1998 |
| WO | WO 99/01560 | | 1/1999 |
| WO | WO 99/33998 | | 7/1999 |
| WO | WO 99/38964 | | 8/1999 |
| WO | WO 00/46355 | | 8/2000 |

OTHER PUBLICATIONS

Cong et al (Hum. Mol. Genet. 8(1): 137–142, 1999).*

Majumdar et al. The telomerase reverse transcriptase promoter drives efficacious tumor suicide gene therapy while preventing hepatotoxicity encountered with constitutive promoters. Gene Therapy 8:568, 2001.

Koga et al. A novel telomerase–specific gene therapy: Gene transfer of caspase–8 utilizing the human telomerase catalytic subunit gene promoter. Hu. Gene Ther. 11:1397, 2000.

Gu et al. Tumor–specific transgene expression from the human telomerase reverse transcriptase promoter enables targeting of the therapeutic effects of the Bax gene to cancers. Cancer Res. 60:5339, 2000.

Komata et al. Treatment of malignant glioma cells with the transfer of constitutively active Caspase–6 using the human telomerase catalytic subunit (human telomerase reverse transcriptase) gene promoter. Cancer Res. 61:5796, 2001.

Geron Corporation Press Release.. Geron Corporation and Genetic tTherapy, Inc. partner to develop cancer therapy. Jan. 7, 2002.

Berenstein, M., et al., "Different efficacy of in vivo herpes simplex virus thymidine kinase gene transduction and ganciclovir treatment on the inhibition of tumor growth of murine and human melanoma cells and rat glioblastoma cells", *Cancer Gene Therapy*, 6(4):358–366 (1999).

Bi, W., et al., "An HSV tk–mediated local and distant antitumor bystander effect in tumors of head and neck origin in athymic mice", *Cancer Gene Therapy*, 4(4):246–252 (1997).

Brand, K., et al., "Tumor cell–specific transgene expression prevents liver toxicity of the adeno–HSVtk/GCV approach", *Gene Therapy*, 5:1363–1371 (1998).

Cong, YS., et al., "The Human Telomerase Catalytic Subunit hTERT: Organization of the Gene and Characterization of the Promoter", *Human Molecular Genetics*, 8(1):137–142 (1999).

(List continued on next page.)

*Primary Examiner*—Dave T. Nguyen
*Assistant Examiner*—Richard Schnizer
(74) *Attorney, Agent, or Firm*—J. Michael Schiff; David J. Earp

(57) ABSTRACT

The present invention is related to novel nucleic acids comprising telomerase reverse transcriptase (TERT) cis-acting transcriptional control sequences, including TERT human and mouse promoter sequences. The present invention is further directed to methods of using these cis-acting transcriptional control sequences, for example, to drive heterologous gene sequences; to modulate the level of transcription of TERT or to isolate novel trans-acting regulatory factors which bind to and modulate the activity of a TERT promoter.

23 Claims, 13 Drawing Sheets

OTHER PUBLICATIONS

Devereux, T.R., et al., "DNA Methylation Analysis of the Promoter Region of the Human Telomerase Reverse Transcriptase (hTERT) Gene", *Cancer Res.*, 59:6087–6090 (Dec 15, 1999).

Elshami, A.A., et al., "The effect of promoter strength in adenoviral vectors containing herpes simplex virus thymidine kinase on cancer gene therapy in vitro and in vivo", *Cancer Gene Therapy*, 4(4):213–221 (1997).

Horikawa, I., et al., "Cloning and Characterization of the Promoter Region of Human Telomerase Reverse Transcriptase Gene", *Cancer Res.*, 59:826–830 (Feb. 15, 1999).

Klatzmann, D., et al., "A Phase I/II Dose–Escalation Study of Herpes Simplex Virus Type I Thymidine Kinase "Suicide" Gene Therapy for Metastatic Melanoma", *Human Gene Therapy*, 9:2585–2594 (Nov. 20, 1998).

Klatzmann, D., et al., "A Phase I/II Study of Herpes Simplex Virus Type I Thymidine Kinase "Suicide" Gene Therapy for Recurrent Glioblastoma", *Human Gene Therapy*, 9:2595–2604 (Nov. 20, 1998).

Li, P–X., et al., "Differential chemosensitivity of breast cancer cells to ganciclovir treatment following adenovirus–mediated herpes simplex virus thymidine kinase gene transfer", *Cancer Gene Therapy*, 6(2):179–190 (1999).

Princen, F., et al., "Repeated cycles of retrovirus–mediated HSVtk gene transfer plus ganciclovir increase survival of rats with peritoneal carcinomatosis", *Gene Therapy*, 5:1054–1060 (1998).

Robertson, M.W., III, et al., "Use of a tissue–specific promoter for targeted expression of the herpes simplex virus thymidine kinase gene in cervical carcinoma cells", *Cancer Gene Therapy*, 5(5):331–336 (1998).

Shand, N., et al., "A Phase 1–2 Clinical Trial of Gene Therapy for Recurrent Glioblastoma Multiforme by Tumor Transduction with the Herpes Simplex Thymidine Kinase Gene Followed by Ganciclovir", *Human Gene Therapy*, 10:2325–2335 (Sep. 20, 1999).

Siders, W.M., et al., "Melanoma–specific cytotoxicity induced by a tyrosinase promoter–enhancer/herpes simplex virus thymidine kinase adenovirus", *Cancer Gene Therapy*, 5(5):281–291 (1998).

Smiley, W.R., et al., "Establishment of Parameters for Optimal Transduction Efficiency and Antitumor Effects with Purified High–Titer HSV–TK Retroviral Vector in Established Solid Tumors", *Human Gene Therapy*, 8:965–977 (May 20, 1997).

Sterman, D.H., et al., "Adenovirus–Mediated Herpes Simplex Virus Thymidine Kinase/Ganciclovir Gene Therapy in Patients with Localized Malignancy: Results of a Phase I Clinical Trial in Malignant Mesothelioma", *Human Gene Therapy*, 9:1083–1092 (May 1, 1998).

Su, H., et al., "Tissue–specific expression of herpes simplex virus thymidine kinase gene delivered by adeno–associated virus inhibits the growth of human hepatocellular carcinoma in athymic mice", *Proc. Natl. Acad. Sci. USA*, 94 : 13891–13896 (Dec. 1997).

Takakura, M., et al., "Cloning of Human Telomerase Catalytic Subunit (hTERT) Gene Promoter and Identification of Proximal Core Promoter Sequences Essential for Transcriptional Activation in Immortalized and Cancer Cells", *Cancer Res.*, 59:551–557 (Feb. 1, 1999).

Wick, M., et al., "Genomic organization and promoter characterization of the gene encoding the human telomerase reverse transcriptase (hTERT)", *Gene*, 232:97–106 (1999).

Wildner, O., et al., "Adenoviral vectors capable of replication improve the efficacy of HSVtkGCV suicide gene therapy of cancer", *Gene Therapy*, 6:57–62 (1999).

Wildner, O., et al., "Therapy of Colon Cancer with Oncolytic Adenovirus Is Enhanced by the Addition of Herpes Simplex Virus–thymidine kinase", *Cancer Research*, 59:410/413 (1999).

Wu, K.–J., et al., "Direct activation of TERT transcription by c–MYC", *Nature Genetics*, 21:220–224 (Feb. 1999).

Yang, L., et al., "Intercellular Communication Mediates the Bystander Effect During Herpes Simplex Thymidine Kinase/Ganciclovir–Based Gene Therapy of Human Gastrointestinal Tumor Cells", *Human Gene Therapy*, 9:719–728 (Mar. 20, 1998).

\* cited by examiner

Figure 2(A)

SEQUENCE LISING SEQ. ID NO:1
ATTORNEY DOCKET NO. 015389-004000US
INFORMATION FOR SEQ. ID NO:1
   (i) SEQUENCE CHARACTERISTICS:
      (A) LENGTH: 15418 base pairs
      (B) TYPE: nucleic acid
      (C) STRANDEDNESS: single
      (D) TOPOLOGY: linear
   (ii) MOLECULE TYPE: DNA (genomic)

```
GCGGCCGCGA GCTCTAATAC GACTCACTAT AGGGCGTCGA CTCGATCAAT GGAAGATGAG   60
GCATTGCCGA AGAAAAGATT AATGGATTTG AACACACAGC AACAGAAACT ACATGAAGTG  120
AAACACAGGA AAAAAAAGAT AAAGAAACGA AAAGAAAAGG GCATCAGTGA GCTTCAGCAG  180
AAGTTCCATC GGCCTTACAT ATGTGTAAGC AGAGGCCCTG TAGGAGCAGA GGCAGGGGGA  240
AAATACTTTA AGAAATAATG TCTAAAAGTT TTTCAAATAT GAGGAAAAAC ATAAAACCAC  300
AGATCCAAGA AGCTCAACAA AACAAAGCAC AAGAAACAGG AAGAAATTAA AAGTTATATC  360
ACAGTCAAAT TGCTGAAAAC CAGCAACAAA GAGAATATCT TAAGAGTATC AGAGGAAAAG  420
AGATTAATGA CAGGCCAAGA AACAATGAAA ACAATACAGA TTTCTTGTAG GAAACACAAG  480
ACAAAAGACA TTTTTTAAAA CCAAAAGGAA AAAAATGCT ACATTAAAAT GTTTTTTACC   540
CACTGAAAGT ATATTTCAAA ACATATTTTA GGCCAGGCTT GGTGGCTCAC ACCTGTAATC  600
CCAGCACTTT GGGAGGCCAA GGTGGGTGGA TCGCTTAAGG TCAGGAGTTC GAGACCAGCC  660
TGGCCAATAT AGCGAAACCC CATCTGTACT AAAAACACAA AAATTAGCTG GGTGTGGTGA  720
CACATGCCTG TAATCCCAGG TACTCAGGAG GCTAAGGCAG GAGAATTGCT TGAACTGGGA  780
GGCAGAGGTG GTGAGCCAAG ATTGCACCAG TGCACTCCAG CCTTGGTGAC AGAGTGAAAC  840
TCCATCTCAA AAACAAACAA ACAAAATACA TATACATAAA TATATATGCA CATATATATA  900
CATATATAAA TATATATACA CATATATAAA TCTATATACA TATATACATA TATACACATA  960
TATAAATCTA TATACATATA TATACATATA TAATATATTT ACATATATAA ATATATACAT 1020
ATATAAATAT ACATATATAA ATACATATAT AAATATACAT ATATAAATAT ACATATATAA 1080
ATATACATAT ATAAATATAT ACATATATAA ATACATATAT ATAAATATAT ATACATATAT 1140
AAATATATAA ATATACAAGT ATATACAAAT ATATACATAT ATAAATGTAT ATACGTATAT 1200
ACATATATAT ATAAATATAT AAAAAAACTT TTGGCTGGGC ACCTTTCCAA ATCTCATGGC 1260
ACATATAAGT CTCATGGTAA CCTCAAATAA AAAAACATAT AACAGATACA CCAAAAATAA 1320
AAACCAATAA ATTAAATCAT GCCACCAGAA GAAATTACCT TCACTAAAAG GAACACAGGA 1380
AGGAAAGAAA GAAGGAAGAG AAGACCATGA AACAACCAGA AAACAAACAA CAAAACAGCA 1440
GGAGTAATTC CTGACTTATC AATAATAATG CTGGGTGTAA ATGGACTAAA CTCTCCAATC 1500
AAAAGACATA GAGTGGCTGA ATGGACGAAA AAAACAAGAC TCAATAATCT GTTGCCTACA 1560
AGAATATACT TCACCTATAA AGGGACACAT AGACTGAAAA TAAAAGGAAG GAAAAATATT 1620
CTATGCAAAT GGAAACCAAA AAAAGAACAG AACTAGCTAC ACTTATATCA GACAAAATAG 1680
ATTTCAAGAC AAAAAGTACA AAAAGAGACA AAGTAATTAT ATAATAATAA AGCAAAAAGA 1740
TATAACAATT GTGAATTTAT ATGCGCCCAA CACTGGGACA CCCAGATATA TACAGCAAAT 1800
ATTATTAGAA CTAAGGAGAG AGAGAGATCC CCATACAATA ATAGCTGGAG ACTTCACCCC 1860
GCTTTTAGCA TTGGACAGAT CATCCAGACA GAAAATCAAC CAAAAAATTG GACTTAATCT 1920
ATAATATAGA ACAAATGTAC CTAATTGATG TTTACAAGAC ATTTCATCCA GTAGTTGCAG 1980
AATATGCATT TTTTCCTCAG CATATGGATC ATTCTCAAGG ATAGACCATA TATTAGGCCA 2040
CAGAACAAGC CATTAAAAAT TCAAAAAAAT TGAGCCAGGC ATGATGGCTT ATGCTTGTAA 2100
TTACAGCACT TTGGGGAGGG TGAGGTGGGA GGATGTCTTG AGTACAGGAG TTTGAGACCA 2160
GCCTGGGCAA AATAGTGAGA CCCTGTCTCT ACAAACTTTT TTTTTAATT AGCCAGGCAT  2220
AGTGGTGTGT GCCTGTAGTC CCAGCTACTT AGGAGGCTGA AGTGGGAGGA TCACTTGAGC 2280
```

Figure 2(B)

```
CCAAGAGTTC AAGGCTACGG TGAGCCATGA TTGCAACACC ACACACCAGC CTTGGTGACA 2340
GAATGAGACC CTGTCTCAAA AAAAAAAAAA AAAATTGAAA TAATATAAAG CATCTTCTCT 2400
GGCCACAGTG GAACAAAACC AGAAATCAAC AACAAGAGGA ATTTTGAAAA CTATACAAAC 2460
ACATGAAAAT TAAACAATAT ACTTCTGAAT AACCAGTGAG TCAATGAAGA AATTAAAAAG 2520
GAAATTGAAA AATTTATTTA AGCAAATGAT AACGGAAACA TAACCTCTCA AAACCCACGG 2580
TATACAGCAA AAGCAGTGCT AAGAAGGAAG TTTATAGCTA TAAGCAGCTA CATCAAAAAA 2640
GTAGAAAAGC CAGGCGCAGT GGCTCATGCC TGTAATCCCA GCACTTTGGG AGGCCAAGGC 2700
GGGCAGATCG CCTGAGGTCA GGAGTTCGAG ACCAGCCTGA CCAACACAGA GAAACCTTGT 2760
CGCTACTAAA AATACAAAAT TAGCTGGGCA TGGTGGCACA TGCCTGTAAT CCCAGCTACT 2820
CGGGAGGCTG AGGCAGGATA ACCGCTTGAA CCCAGGAGGT GGAGGTTGCG GTGAGCCGGG 2880
ATTGCGCCAT TGGACTCCAG CCTGGGTAAC AAGAGTGAAA CCCTGTCTCA AGAAAAAAAA 2940
AAAAGTAGAA AAACTTAAAA ATACAACCTA ATGATGCACC TTAAAGAACT AGAAAAGCAA 3000
GAGCAAACTA AACCTAAAAT TGGTAAAAGA AAAGAAATAA TAAAGATCAG AGCAGAAATA 3060
AATGAAACTG AAAGATAACA ATACAAAAGA TCAACAAAAT TAAAAGTTGG TTTTTTGAAA 3120
AGATAAACAA AATTGACAAA CCTTTGCCCA GACTAAGAAA AAAGGAAAGA AGACCTAAAT 3180
AAATAAAGTC AGAGATGAAA AAAGAGACAT TACAACTGAT ACCACAGAAA TTCAAAGGAT 3240
CACTAGAGGC TACTATGAGC AACTGTACAC TAATAAATTG AAAAACCTAG AAAAAATAGA 3300
TAAATTCCTA GATGCATACA ACCTACCAAG ATTGAACCAT GAAGAAATCC AAAGCCCAAA 3360
CAGACCAATA ACAATAATGG GATTAAAGCC ATAATAAAAA GTCTCCTAGC AAAGAGAAGC 3420
CCAGGACCCA ATGGCTTCCC TGCTGGATTT TACCAATCAT TTAAAGAAGA ATGAATTCCA 3480
ATCCTACTCA AACTATTCTG AAAAATAGAG GAAAGAATAC TTCCAAACTC ATTCTACATG 3540
GCCAGTATTA CCCTGATTCC AAAACCAGAC AAAAACACAT CAAAAACAAA CAAACAAAAA 3600
AACAGAAAGA AAGAAAACTA CAGGCCAATA TCCCTGATGA ATACTGATAC AAAAATCCTC 3660
AACAAAACAC TAGCAAACCA AATTAAACAA CACCTTCGAA AGATCATTCA TTGTGATCAA 3720
GTGGGATTTA TTCCAGGGAT GGAAGGATGG TTCAACATAT GCAAATCAAT CAATGTGATA 3780
CATCATCCCA ACAAAATGAA GTACAAAAAC TATATGATTA TTTCACTTTA TGCAGAAAAA 3840
GCATTTGATA AAATTCTGCA CCCTTCATGA TAAAAACCCT CAAAAAACCA GGTATACAAG 3900
AAACATACAG GCCAGGCACA GTGGCTCACA CCTGCGATCC CAGCACTCTG GGAGGCCAAG 3960
GTGGGATGAT TGCTTGGGCC CAGGAGTTTG AGACTAGCCT GGGCAACAAA ATGAGACCTG 4020
GTCTACAAAA AACTTTTTTA AAAATTAGC CAGGCATGAT GGCATATGCC TGTAGTCCCA 4080
GCTAGTCTGG AGGCTGAGGT GGGAGAATCA CTTAAGCCTA GGAGGTCGAG GCTGCAGTGA 4140
GCCATGAACA TGTCACTGTA CTCCAGCCTA GACAACAGAA CAAGACCCCA CTGAATAAGA 4200
AGAAGGAGAA GGAGAAGGGA GAAAGGAGGG AGAAGGGAGG AGGAGGAGAA GGAGGAGGTG 4260
GAGGAGAAGT GGAAGGGGAA GGGGAAGGGA AAGAGGAAGA AGAAGAAACA TATTTCAACA 4320
TAATAAAAGC CCTATATGAC AGACCGAGGT AGTATTATGA GGAAAAACTG AAAGCCTTTC 4380
CTCTAAGATC TGGAAAATGA CAAGGGCCCA CTTTCACCAC TGTGATTCAA CATAGTACTA 4440
GAAGTCCTAG CTAGAGCAAT CAGATAAGAG AAAGAAATAA AAGGCATCCA AACTGGAAAG 4500
GAAGAAGTCA AATTATCCTG TTTGCAGATG ATATGATCTT ATATCTGGAA AAGACTTAAG 4560
ACACCACTAA AAAACTATTA GAGCTGAAAT TTGGTACAGC AGGATACAAA ATCAATGTAC 4620
AAAAATCAGT AGTATTTCTA TATTCCAACA GCAAACAATC TGAAAAAGAA ACCAAAAAAG 4680
CAGCTACAAA TAAAATTAAA CAGCTAGGAA TTAACCAAAG AAGTGAAAGA TCTCTACAAT 4740
GAAAACTATA AATATTGAT AAAAGAAATT GAAGAGGGCA CAAAAAAAGA AAAGATATTC 4800
CATGTTCATA GATTGGAAGA ATAAATACTG TTAAAATGTC CATACTACCC AAAGCAATTT 4860
ACAAATTCAA TGCAATCCCT ATTAAAATAC TAATGACGTT CTTCACAGAA ATAGAAGAAA 4920
CAATTCTAAG ATTTGTACAG AACCACAAAA GACCCAGAAT AGCCAAAGCT ATCCTGACCA 4980
AAAAGAACAA AACTGGAAGC ATCACATTAC CTGACTTCAA ATTATACTAC AAAGCTATAG 5040
TAACCCAAAC TACATGGTAC TGGCATAAAA ACAGATGAGA CATGGACCAG AGGAACAGAA 5100
TAGAGAATCC AGAAACAAAT CCATGCATCT ACAGTGAACT CATTTTTGAC AAAGGTGCCA 5160
AGAACATACT TTGGGGAAAA GATAATCTCT TCAATAAATG GTGCTGGAGG AACTGGATAT 5220
```

Figure 2(C)

```
CCATATGCAA AATAACAATA CTAGAACTCT GTCTCTCACC ATATACAAAA GCAAATCAAA 5280
ATGGATGAAA GGCTTAAATC TAAAACCTCA AACTTTGCAA CTACTAAAAG AAAACACCGG 5340
AGAAACTCTC CAGGACATTG GAGTGGGCAA AGACTTCTTG AGTAATTCCC TGCAGGCACA 5400
GGCAACCAAA GCAAAAACAG ACAAATGGGA TCATATCAAG TTAAAAAGCT TCTGCCCAGC 5460
AAAGGAAACA ATCAACAAAG AGAAGAGACA ACCCACAGAA TGGGAGAATA TATTTGCAAA 5520
CTATTCATCT AACAAGGAAT TAATAACCAG TATATATAAG GAGCTCAAAC TACTCTATAA 5580
GAAAAACACC TAATAAGCTG ATTTTCAAAA ATAAGCAAAA GATCTGGGTA GACATTTCTC 5640
AAAATAAGTC ATACAAATGG CAAACAGGCA TCTGAAAATG TGCTCAACAC CACTGATCAT 5700
CAGAGAAATG CAAATCAAAA CTACTATGAG AGATCATCTC ACCCCAGTTA AAATGGCTTT 5760
TATTCAAAAG ACAGGCAATA ACAAATGCCA GTGAGGATGT GGATAAAAGG AAACCCTTGG 5820
ACACTGTTGG TGGGAATGGA AATTGCTACC ACTATGGAGA ACAGTTTGAA AGTTCCTCAA 5880
AAAACTAAAA ATAAAGCTAC CATACAGCAA TCCCATTGCT AGGTATATAC TCCAAAAAAG 5940
GGAATCAGTG TATCAACAAG CTATCTCCAC TCCCACATTT ACTGCAGCAC TGTTCATAGC 6000
AGCCAAGGTT TGGAAGCAAC CTCAGTGTCC ATCAACAGAC GAATGGAAAA AGAAAATGTG 6060
GTGCACATAC ACAATGGAGT ACTACGCAGC CATAAAAAAG AATGAGATCC TGTCAGTTGC 6120
AACAGCATGG GGGGCACTGG TCAGTATGTT AAGTGAAATA AGCCAGGCAC AGAAAGACAA 6180
ACTTTTCATG TTCTCCCTTA CTTGTGGGAG CAAAAATTAA AACAATTGAC ATAGAAATAG 6240
AGGAGAATGG TGGTTCTAGA GGGGTGGGGG ACAGGGTGAC TAGAGTCAAC AATAATTTAT 6300
TGTATGTTTT AAAATAACTA AAAGAGTATA ATTGGGTTGT TTGTAACACA AAGAAAGGAT 6360
AAATGCTTGA AGGTGACAGA TACCCCATTT ACCCTGATGT GATTATTACA CATTGTATGC 6420
CTGTATCAAA ATATCTCATG TATGCTATAG ATATAAACCC TACTATATTA AAAATTAAAA 6480
TTTTAATGGC CAGGCACGGT GGCTCATGTC CATAATCCCA GCACTTTGGG AGGCCGAGGC 6540
GGTGGATCAC CTGAGGTCAG GAGTTTGAAA CCAGTCTGGC CACCATGATG AAACCCTGTC 6600
TCTACTAAAG ATACAAAAAT TAGCCAGGCG TGGTGGCACA TACCTGTAGT CCCAACTACT 6660
CAGGAGGCTG AGACAGGAGA ATTGCTTGAA CCTGGGAGGC GGAGGTTGCA GTGAGCCGAG 6720
ATCATGCCAC TGCACTGCAG CCTGGGTGAC AGAGCAAGAC TCCATCTCAA AACAAAAACA 6780
AAAAAAAGAA GATTAAAATT GTAATTTTTA TGTACCGTAT AAATATATAC TCTACTATAT 6840
TAGAAGTTAA AAATTAAAAC AATTATAAAA GGTAATTAAC CACTTAATCT AAAATAAGAA 6900
CAATGTATGT GGGGTTTCTA GCTTCTGAAG AAGTAAAAGT TATGGCCACG ATGGCAGAAA 6960
TGTGAGGAGG GAACAGTGGA AGTTACTGTT GTTAGACGCT CATACTCTCT GTAAGTGACT 7020
TAATTTTAAC CAAAGACAGG CTGGGAGAAG TTAAAGAGGC ATTCTATAAG CCCTAAAACA 7080
ACTGCTAATA ATGGTGAAAG GTAATCTCTA TTAATTACCA ATAATTACAG ATATCTCTAA 7140
AATCGAGCTG CAGAATTGGC ACGTCTGATC ACACCGTCCT CTCATTCACG GTGCTTTTTT 7200
TCTTGTGTGC TTGGAGATTT TCGATTGTGT GTTCGTGTTT GGTTAAACTT AATCTGTATG 7260
AATCCTGAAA CGAAAAATGG TGGTGATTTC CTCCAGAAGA ATTAGAGTAC CTGGCAGGAA 7320
GCAGGTGGCT CTGTGGACCT GAGCCACTTC AATCTTCAAG GGTCTCTGGC CAAGACCCAG 7380
GTGCAAGGCA GAGGCCTGAT GACCCGAGGA CAGGAAAGCT CGGATGGGAA GGGGCGATGA 7440
GAAGCCTGCC TCGTTGGTGA GCAGCGCATG AAGTGCCCTT ATTTACGCTT TGCAAAGATT 7500
GCTCTGGATA CCATCTGGAA AAGGCGGCCA GCGGGAATGC AAGGAGTCAG AAGCCTCCTG 7560
CTCAAACCCA GGCCAGCAGC TATGGCGCCC ACCCGGGCGT GTGCCAGAGG GAGAGGAGTC 7620
AAGGCACCTC GAAGTATGGC TTAAATCTTT TTTTCACCTG AAGCAGTGAC CAAGGTGTAT 7680
TCTGAGGGAA GCTTGAGTTA GGTGCCTTCT TTAAAACAGA AAGTCATGGA AGCACCCTTC 7740
TCAAGGGAAA ACCAGACGCC CGCTCTGCGG TCATTTACCT CTTTCCTCTC TCCCTCTCTT 7800
GCCCTCGCGG TTTCTGATCG GGACAGAGTG ACCCCGTGG AGCTTCTCCG AGCCCGTGCT 7860
GAGGACCCTC TTGCAAAGGG CTCCACAGAC CCCCGCCCTG GAGAGAGGAG TCTGAGCCTG 7920
GCTTAATAAC AAACTGGGAT GTGGCTGGGG GCGGACAGCG ACGGCGGGAT TCAAAGACTT 7980
AATTCCATGA GTAAATTCAA CCTTTCCACA TCCGAATGGA TTTGGATTTT ATCTTAATAT 8040
TTTCTTAAAT TTCATCAAAT AACATTCAGG AGTGCAGAAA TCCAAGGCG TAAAACAGGA 8100
ACTGAGCTAT GTTTGCCAAG GTCCAAGGAC TTAATAACCA TGTTCAGAGG GATTTTTCGC 8160
```

Figure 2(D)

```
CCTAAGTACT TTTTATTGGT TTTCATAAGG TGGCTTAGGG TGCAAGGGAA AGTACACGAG 8220
GAGAGGACTG GGCGGCAGGG CTATGAGCAC GGCAAGGCCA CCGGGGAGAG AGTCCCCGGC 8280
CTGGGAGGCT GACAGCAGGA CCACTGACCG TCCTCCCTGG GAGCTGCCAC ATTGGGCAAC 8340
GCGAAGGCGG CCACGCTGCG TGTGACTCAG GACCCCATAC CGGCTTCCTG GGCCCACCCA 8400
CACTAACCCA GGAAGTCACG GAGCTCTGAA CCCGTGGAAA CGAACATGAC CCTTGCCTGC 8460
CTGCTTCCCT GGGTGGGTCA AGGGTAATGA AGTGGTGTGC AGGAAATGGC CATGTAAATT 8520
ACACGACTCT GCTGATGGGG ACCGTTCCTT CCATCATTAT TCATCTTCAC CCCCAAGGAC 8580
TGAATGATTC CAGCAACTTC TTCGGGTGTG ACAAGCCATG ACAACACTCA GTACAAACAC 8640
CACTCTTTTA CTAGGCCCAC AGAGCACGGC CCACACCCCT GATATATTAA GAGTCCAGGA 8700
GAGATGAGGC TGCTTTCAGC CACCAGGCTG GGGTGACAAC AGCGGCTGAA CAGTCTGTTC 8760
CTCTAGACTA GTAGACCCTG GCAGGCACTC CCCCAGATTC TAGGGCCTGG TTGCTGCTTC 8820
CCGAGGGCGC CATCTGCCCT GGAGACTCAG CCTGGGGTGC CACACTGAGG CCAGCCCTGT 8880
CTCCACACCC TCCGCCTCCA GGCCTCAGCT TCTCCAGCAG CTTCCTAAAC CCTGGGTGGG 8940
CCGTGTTCCA GCGCTACTGT CTCACCTGTC CCACTGTGTC TTGTCTCAGC GACGTAGCTC 9000
GCACGGTTCC TCCTCACATG GGGTGTCTGT CTCCTTCCCC AACACTCACA TGCGTTGAAG 9060
GGAGGAGATT CTGCGCCTCC CAGACTGGCT CCTCTGAGCC TGAACCTGGC TCGTGGCCCC 9120
CGATGCAGGT TCCTGGCGTC CGGCTGCACG CTGACCTCCA TTTCCAGGCG CTCCCCGTCT 9180
CCTGTCATCT GCCGGGGCCT GCCGGTGTGT TCTTCTGTTT CTGTGCTCCT TTCCACGTCC 9240
AGCTGCGTGT GTCTCTGTCC GCTAGGGTCT CGGGGTTTTT ATAGGCATAG GACGGGGGCG 9300
TGGTGGGCCA GGGCGCTCTT GGGAAATGCA ACATTTGGGT GTGAAAGTAG GAGTGCCTGT 9360
CCTCACCTAG GTCCACGGGC ACAGGCCTGG GGATGGAGCC CCCGCCAGGG ACCCGCCCTT 9420
CTCTGCCCAG CACTTTTCTG CCCCCCTCCC TCTGGAACAC AGAGTGGCAG TTTCCACAAG 9480
CACTAAGCAT CCTCTTCCCA AAAGACCCAG CATTGGCACC CCTGGACATT TGCCCCACAG 9540
CCCTGGGAAT TCACGTGACT ACGCACATCA TGTACACACT CCCGTCCACG ACCGACCCCC 9600
GCTGTTTTAT TTTAATAGCT ACAAAGCAGG GAAATCCCTG CTAAAATGTC CTTTAACAAA 9660
CTGGTTAAAC AAACGGGTCC ATCCGCACGG TGGACAGTTC CTCACAGTGA AGAGGAACAT 9720
GCCGTTTATA AAGCCTGCAG GCATCTCAAG GGAATTACGC TGAGTCAAAA CTGCCACCTC 9780
CATGGGATAC GTACGCAACA TGCTCAAAAA GAAAGAATTT CACCCCATGG CAGGGGAGTG 9840
GTTGGGGGGT TAAGGACGGT GGGGGCAGCA GCTGGGGGCT ACTGCACGCA CCTTTTACTA 9900
AAGCCAGTTT CCTGGTTCTG ATGGTATTGG CTCAGTTATG GGAGACTAAC CATAGGGGAG 9960
TGGGGATGGG GGAACCCGGA GGCTGTGCCA TCTTTGCCAT GCCGAGTGT CCTGGGCAGG 10020
ATAATGCTCT AGAGATGCCC ACGTCCTGAT TCCCCCAAAC CTGTGGACAG AACCCGCCCG 10080
GCCCCAGGGC CTTTGCAGGT GTGATCTCCG TGAGGACCCT GAGGTCTGGG ATCCTTCGGG 10140
ACTACCTGCA GGCCCGAAAA GTAATCCAGG GGTTCTGGGA AGAGGCGGGC AGGAGGGTCA 10200
GAGGGGGGCA GCCTCAGGAC GATGGAGGCA GTCAGTCTGA GGCTGAAAAG GGAGGGAGGG 10260
CCTCGAGCCC AGGCCTGCAA GCGCCTCCAG AAGCTGGAAA AAGCGGGGAA GGGACCCTCC 10320
ACGGAGCCTG CAGCAGGAAG GCACGGCTGG CCCTTAGCCC ACCAGGGCCC ATCGTGGACC 10380
TCCGGCCTCC GTGCCATAGG AGGGCACTCG CGCTGCCCTT CTAGCATGAA GTGTGTGGGG 10440
ATTTGCAGAA GCAACAGGAA ACCCATGCAC TGTGAATCTA GGATTATTTC AAAACAAAGG 10500
TTTACAGAAA CATCCAAGGA CAGGGCTGAA GTGCCTCCGG GCAAGGGCAG GGCAGGCACG 10560
AGTGATTTTA TTTAGCTATT TTATTTTATT TACTTACTTT CTGAGACAGA GTTATGCTCT 10620
TGTTGCCCAG GCTGGAGTGC AGCGGCATGA TCTTGGCTCA CTGCAACCTC CGTCTCCTGG 10680
GTTCAAGCAA TTCTCGTGCC TCAGCCTCCC AAGTAGCTGG GATTTCAGGC GTGCACCACC 10740
ACACCCGGCT AATTTTGTAT TTTTAGTAGA GATGGGCTTT CACCATGTTG GTCAGGCTGA 10800
TCTCAAAATC CTGACCTCAG GTGATCCGCC CACCTCAGCC TCCCAAAGTG CTGGGATTAC 10860
AGGCATGAGC CACTGCACCT GGCCTATTTA ACCATTTTAA AACTTCCCTG GCTCAAGTC 10920
ACACCCACTG GTAAGGAGTT CATGGAGTTC AATTTCCCCT TTACTCAGGA GTTACCCTCC 10980
TTTGATATTT TCTGTAATTC TTCGTAGACT GGGGATACAC CGTCTCTTGA CATATTCACA 11040
GTTTCTGTGA CCACCTGTTA TCCCATGGGA CCCACTGCAG GGGCAGCTGG GAGGCTGCAG 11100
```

Figure 2(E)

```
GCTTCAGGTC CCAGTGGGGT TGCCATCTGC CAGTAGAAAC CTGATGTAGA ATCAGGGCGC 11160
GAGTGTGGAC ACTGTCCTGA ATCTCAATGT CTCAGTGTGT GCTGAAACAT GTAGAAATTA 11220
AAGTCCATCC CTCCTACTCT ACTGGGATTG AGCCCCTTCC CTATCCCCCC CCAGGGGCAG 11280
AGGAGTTCCT CTCACTCCTG TGGAGGAAGG AATGATACTT TGTTATTTTT CACTGCTGGT 11340
ACTGAATCCA CTGTTTCATT TGTTGGTTTG TTTGTTTTGT TTTGAGAGGC GGTTTCACTC 11400
TTGTTGCTCA GGCTGGAGGG AGTGCAATGG CGCGATCTTG GCTTACTGCA GCCTCTGCCT 11460
CCCAGGTTCA AGTGATTCTC CTGCTTCCGC CTCCCATTTG GCTGGGATTA CAGGCACCCG 11520
CCACCATGCC CAGCTAATTT TTTGTATTTT TAGTAGAGAC GGGGGTGGGG GTGGGGTTCA 11580
CCATGTTGGC CAGGCTGGTC TCGAACTTCT GACCTCAGAT GATCCACCTG CCTCTGCCTC 11640
CTAAAGTGCT GGGATTACAG GTGTGAGCCA CCATGCCCAG CTCAGAATTT ACTCTGTTTA 11700
GAAACATCTG GGTCTGAGGT AGGAAGCTCA CCCCACTCAA GTGTTGTGGT GTTTTAAGCC 11760
AATGATAGAA TTTTTTTATT GTTGTTAGAA CACTCTTGAT GTTTTACACT GTGATGACTA 11820
AGACATCATC AGCTTTTCAA AGACACACTA ACTGCACCCA TAATACTGGG GTGTCTTCTG 11880
GGTATCAGCG ATCTTCATTG AATGCGGGA GGCGTTTCCT CGCCATGCAC ATGGTGTTAA 11940
TTACTCCAGC ATAATCTTCT GCTTCCATTT CTTCTCTTCC CTCTTTTAAA ATTGTGTTTT 12000
CTATGTTGGC TTCTCTGCAG AGAACCAGTG TAAGCTACAA CTTAACTTTT GTTGGAACAA 12060
ATTTTCCAAA CCGCCCCTTT GCCCTAGTGG CAGAGACAAT TCACAAACAC AGCCCTTTAA 12120
AAAGGCTTAG GGATCACTAA GGGGATTTCT AGAAGAGCGA CCCGTAATCC TAAGTATTTA 12180
CAAGACGAGG CTAACCTCCA GCGAGCGTGA CAGCCCAGGG AGGGTGCGAG GCCTGTTCAA 12240
ATGCTAGCTC CATAAATAAA GCAATTTCCT CCGGCAGTTT CTGAAAGTAG GAAAGGTTAC 12300
ATTTAAGGTT GCGTTTGTTA GCATTTCAGT GTTTGCCGAC CTCAGCTACA GCATCCCTGC 12360
AAGGCCTCGG GAGACCCAGA AGTTTCTCGC CCCTTAGATC CAAACTTGAG CAACCCGGAG 12420
TCTGGATTCC TGGGAAGTCC TCAGCTGTCC TGCGGTTGTG CCGGGGCCCC AGGTCTGGAG 12480
GGGACCAGTG GCCGTGTGGC TTCTACTGCT GGGCTGGAAG TCGGGCCTCC TAGCTCTGCA 12540
GTCCGAGGCT TGGAGCCAGG TGCCTGGACC CCGAGGCTGC CCTCCACCCT GTGCGGGCGG 12600
GATGTGACCA GATGTTGGCC TCATCTGCCA GACAGAGTGC CGGGGCCCAG GGTCAAGGCC 12660
GTTGTGGCTG GTGTGAGGCG CCCGGTGCGC GGCCAGCAGG AGCGCCTGGC TCCATTTCCC 12720
ACCCTTTCTC GACGGGACCG CCCCGGTGGG TGATTAACAG ATTTGGGGTG GTTTGCTCAT 12780
GGTGGGGACC CCTCGCCGCC TGAGAACCTG CAAAGAGAAA TGACGGGCCT GTGTCAAGGA 12840
GCCCAAGTCG CGGGGAAGTG TTGCAGGGAG GCACTCCGGG AGGTCCCGCG TGCCCGTCCA 12900
GGGAGCAATG CGTCCTCGGG TTCGTCCCCA GCCGCGTCTA CGCGCCTCCG TCCTCCCCTT 12960
CACGTCCGGC ATTCGTGGTG CCCGGAGCCC GACGCCCCGC GTCCGGACCT GGAGGCAGCC 13020
CTGGGTCTCC GGATCAGGCC AGCGGCCAAA GGGTCGCCGC ACGCACCTGT TCCCAGGGCC 13080
TCCACATCAT GGCCCCTCCC TCGGGTTACC CCACAGCCTA GGCCGATTCG ACCTCTCTCC 13140
GCTGGGGCCC TCGCTGGCGT CCCTGCACCC TGGGAGCGCG AGCGGCGCGC GGGCGGGGAA 13200
GCGCGGCCCA GACCCCGGG TCCGCCCGGA GCAGCTGCGC TGTCGGGGCC AGGCCGGGCT 13260
CCCAGTGGAT TCGCGGGCAC AGACGCCCAG GACCGCGCTT CCCACGTGGC GGAGGGACTG 13320
GGACCCGGG CACCCGTCCT GCCCCTTCAC CTTCCAGCTC CGCCTCCTCC GCGCGGACCC 13380
CGCCCCGTCC CGACCCCTCC CGGGTCCCCG GCCCAGCCCC CTCCGGGCCC TCCCAGCCCC 13440
TCCCCTTCCT TTCCGCGGCC CCGCCCTCTC CTCGCGGCGC GAGTTTCAGG CAGCGCTGCG 13500
TCCTGCTGCG CACGTGGGAA GCCCTGGCCC CGGCCACCCC CGCGATGCCG CGCGCTCCCC 13560
GCTGCCGAGC CGTGCGCTCC CTGCTGCGCA GCCACTACCG CGAGGTGCTG CCGCTGGCCA 13620
CGTTCGTGCG GCGCCTGGGG CCCCAGGGCT GGCGGCTGGT GCAGCGCGGG GACCCGGCGG 13680
CTTTCCGCGC GCTGGTGGCC CAGTGCCTGG TGTGCGTGCC CTGGGACGCA CGGCCGCCCC 13740
CCGCCGCCCC CTCCTTCCGC CAGGTGGGCC TCCCCGGGGT CGGCGTCCGG CTGGGGTTGA 13800
GGGCGGCCGG GGGGAACCAG CGACATGCGG AGAGCAGCGC AGGCGACTCA GGGCGCTTCC 13860
CCCGCAGGTG TCCTGCCTGA AGGAGCTGGT GGCCCGAGTG CTGCAGAGGC TGTGCGAGCG 13920
CGGCGCGAAG AACGTGCTGG CCTTCGGCTT CGCGCTGCTG GACGGGGCCC GCGGGGCCC 13980
CCCCGAGGCC TTCACCACCA GCGTGCGCAG CTACCTGCCC AACACGGTGA CCGACGCACT 14040
```

Figure 2(F)

```
GCGGGGGAGC GGGGCGTGGG GGCTGCTGCT GCGCCGCGTG GGCGACGACG TGCTGGTTCA 14100
CCTGCTGGCA CGCTGCGCGC TCTTTGTGCT GGTGGCTCCC AGCTGCGCCT ACCAGGTGTG 14160
CGGGCCGCCG CTGTACCAGC TCGGCGCTGC CACTCAGGCC CGGCCCCCGC CACACGCTAG 14220
TGGACCCCGA AGGCGTCTGG GATGCGAACG GGCCTGGAAC CATAGCGTCA GGGAGGCCGG 14280
GGTCCCCCTG GGCCTGCCAG CCCCGGGTGC GAGGAGGCGC GGGGGCAGTG CCAGCCGAAG 14340
TCTGCCGTTG CCCAAGAGGC CCAGGCGTGG CGCTGCCCCT GAGCCGGAGC GGACGCCCGT 14400
TGGGCAGGGG TCCTGGGCCC ACCCGGGCAG GACGCGTGGA CCGAGTGACC GTGGTTTCTG 14460
TGTGGTGTCA CCTGCCAGAC CCGCCGAAGA AGCCACCTCT TTGGAGGGTG CGCTCTCTGG 14520
CACGCGCCAC TCCCACCCAT CCGTGGGCCG CCAGCACCAC GCGGGCCCCC CATCCACATC 14580
GCGGCCACCA CGTCCCTGGG ACACGCCTTG TCCCCGGTG TACGCCGAGA CCAAGCACTT 14640
CCTCTACTCC TCAGGCGACA AGGAGCAGCT GCGGCCCTCC TTCCTACTCA GCTCTCTGAG 14700
GCCCAGCCTG ACTGGCGCTC GGAGGCTCGT GGAGACCATC TTTCTGGGTT CCAGGCCCTG 14760
GATGCCAGGG ACTCCCCGCA GGTTGCCCCG CCTGCCCCAG CGCTACTGGC AAATGCGGCC 14820
CCTGTTTCTG GAGCTGCTTG GGAACCACGC GCAGTGCCCC TACGGGGTGC TCCTCAAGAC 14880
GCACTGCCCG CTGCGAGCTG CGGTCACCCC AGCAGCCGGT GTCTGTGCCC GGGAGAAGCC 14940
CCAGGGCTCT GTGGCGGCCC CCGAGGAGGA GGACACAGAC CCCCGTCGCC TGGTGCAGCT 15000
GCTCCGCCAG CACAGCAGCC CCTGGCAGGT GTACGGCTTC GTGCGGGCCT GCCTGCGCCG 15060
GCTGGTGCCC CCAGGCCTCT GGGGCTCCAG GCACAACGAA CGCCGCTTCC TCAGGAACAC 15120
CAAGAAGTTC ATCTCCCTGG GGAAGCATGC CAAGCTCTCG CTGCAGGAGC TGACGTGGAA 15180
GATGAGCGTG CGGGACTGCG CTTGGCTGCG CAGGAGCCCA GGTGAGGAGG TGGTGGCCGT 15240
CGAGGGCCCA GGCCCCAGAG CTGAATGCAG TAGGGGCTCA GAAAAGGGGG CAGGCAGAGC 15300
CCTGGTCCTC CTGTCTCCAT CGTCACGTGG GCACACGTGG CTTTTCGCTC AGGACGTCGA 15360
GTGGACACGG TGATCGAGTC GACTCCCTTT AGTGAGGGTT AATTGAGCTC GCGGCCGC     15418
```

Figure 4(A)

[Sequence alignment figure showing human and mouse TERT promoter sequences from approximately -290 to +1, with positions labeled. The figure displays alignments between Human and Mouse sequences, Human ORF and Mouse ORF sequences, and Promoter/reporter constructs including hTERT sequence, 2.4 Kb reporter, and ΔE reporter ORF.]

Figure 5(A)

```
SEQUENCE LISING SEQ. ID NO:1
ATTORNEY DOCKET NO. 015389-004000US
INFORMATION FOR SEQ. ID NO:2
    LOCUS B2.128  7498 bp DNA
    DEFINITION: Genomic sequence of the murine Telomerase
                reverse transcriptase gene promoter region
    GenBank ACCESSION NO: B2.18 AF121949
    BASE COUNT:  1944 a   1857 c   1815 g   1882 t
```

```
aagcttccag caaaccagtt agagctgagt tgatgctctg aagaagagaa aatgtagaga   60
cggtactgaa caaataatgt ctgggcaaac ctcagacatg aaaatggaag acgtggaaat  120
ccagagaact ctgagggaaa ataaaacaca actccaggtc atcacgggac tcatcaaact  180
gctgaggtgc agccacagag aaaaatctta aaatagccta gaacgatgca tgacacataa  240
agcacagaga agacgaagct gagtctgtct tgtaggaaca acttgagaag acctaaacca  300
ctgcaatgag tgcattctgc taacttagaa tttgctaccc agttcagatc caaaaagggt  360
ttcacaaagt tcaacacaaa acagtagcag gagtggctaa gggggacaca ctgataggaa  420
ttcagagaag tagggaatgc tcatatgggg acattacaaa atgtactttc atgttgctta  480
aatcatttta attgtcaacc acatcaagct aaataatgct ttgaggttca taacatttgg  540
agattatgtc tacactagca gagaaggcac caataacatc ccaattgcta gattctcata  600
gaatcatgag tcacaatggc agagacaggt tctgagagtg tgtccttgtt gtaaacagta  660
tgctctacaa actaagttgg ctgcaatatc actaggcagt gttgtcccat aagacaacta  720
tcacatatgt ggtccagtga tgaccaaagc atcttttagc attttgcaaa tgaagctcaa  780
atcgaatatg actaagctca tgcagtacaa atcaaaggta cactgggata gtttaaaaga  840
tacatacttg tactggttag ttttgtgtca gcttgacaca gctggagtta tcacagagaa  900
aagagcttca gttgaggaaa ttcctccatg agatccagct atagggcatt ttctcaatta  960
gtgatcaagg ggggaaggcc ccttgtgggt gggaccatct ctgggctggt agtcttggtt 1020
ctataagaga gcaggctgag caagccagga gaagcaagcc agtaaagaac atccctccat 1080
ggcttctgca tcagctcctg ctccctgacc tgcttgagtt ccagttctaa cttctttcag 1140
tgatgaacag caatgtggaa atgaaagctg aataaaccct ttcctcccca ttttgcttct 1200
tggtcatgat gtttgtgcag gaatagaaac cctgactaag acaatactat aaaccctaaa 1260
agttgtaaac caaacacatg tgtttccatt aagccatcgt agaacaataa gtactcaacc 1320
ccaagtcaca taactataat cccagccttt gaaaaccggg atcaggaatt caaggctagc 1380
ctcatctata tgtaagatta agcctgtttt gggctgcatg agactttgtt tcaaaaaaaa 1440
aaaaaaaaaa gcaaacaggc aaaaacaaac acaagacaag acagatgtaa aatgaaggag 1500
gggtagatgg gtcaagtaga aaatagcata ggaaacgagt caagtataga agaggtggta 1560
gtaaccagat catgcagaag gactcaaggc catctcctca cagtggctta ggtaggcctt 1620
cctctgctct tgagcagggg cagagttgcc gctttaagga ggggatcagt cacctttaag 1680
aactgaaaag ctgaacagtc ttctcaagtc agaagccagt ggcttcatct tacacctctc 1740
ttccttccct tgctactcat attggatctg atgatttgcc caacttggaa gaaacatctc 1800
ttctgaaggg tttcacagac accccatctt tccgagaaag gaccgcatag gctggccatc 1860
cctgtgctta caaaggaat aattaagaaa cttaattcca taagcaaata caaccttttcc 1920
aagccccaag tggatgattt tatcttactg ttttttttata tctcatcaaa taacttccaa 1980
gggctcaaaa atccaaagat gtaaaaaagg aactgagctc tgtttgccaa gccatgagga 2040
ttaaataatg acattcaaag agatttttgt gccctaagta ctttttattg gttttcatag 2100
atggtttaat gtgcaagatg aagcaaacag agatgggagt ggtatcagca tggattaagg 2160
tggcagttgt gagggagggg tactgagaga acaggacaag gtaacctatc taaggagagg 2220
ccaagttggc aagtgccagg gacttctaag cccagaacta gtacacattc cttaggtgct 2280
gtttgggaag tcagggagtc accagccttg ggatctataa aagtgcatgg tggcattcac 2340
tcacatactt cctgagctgt tcgatgttga tgaagtcgtg ggtatgagac tgttgtgtca 2400
```

Figure 5(B)

```
gtgacaaact atgtaaatga gaatgattgt ttccatcttg accactaaga cgtaaaccgg 2460
ttccagtgat ctccaaacat ggcaagctac agcagagcag cagccccatc cagagccttg 2520
ccctggttct gaatggggga gaatccagtg ggagtcggtt gctgccagca tgttggggta 2580
gaaggctgga gcatgacagg tccccgagga tttcctgctt cctatatggg tagggatact 2640
tgaggtcctc tcttctacct ccttccctgc agggtttata acctctacca ctgtctgtct 2700
ctgggatagc tcctagggtg cagcccctcc ccaaaaaggc ctctccctgg cctcatgtct 2760
ctaagaacag cttttctaaag caggcctgtt acacaaaggc tcccttttcc tggcttcatc 2820
gttgctggta gacaacttcc actcgttttc cacttcagtt tcttctactc tgttgttatt 2880
tgattctgat gcttgaaccc agggttgtgt agtcagcaag tgctaccccc tccctcctct 2940
tctttgtttt tttgaggcag ggtctcattt tgcccaagtg gacctaaatt tcagcatgta 3000
gctggcctgg ttttgaatgc cttctcatcc tgcctctact tcccaagagt agcttacaag 3060
tgtgcaccac catgccccgc gatattctta tttttgagac tgttttctat gctggtttct 3120
ttggggaact acactaaggt agcttacaag tgtgcaccac catgccccgc gatattctta 3180
tttttgagac tgttttctat gctggtttct ttggggaact acactaaggt agcttcattg 3240
ttggcataaa tttctcagtt caggcccata tctcctaagt agcagaacta agcaaatctc 3300
aaacaaaccc ctcaaaaaga ctgatgtcca ctaaacggac ttctaaaata gctcctgtaa 3360
tcctgagcat ttacaaggcg gcagacctcc tataagggag taaatatgaa aacgcgcctg 3420
ttcaaatgct aggtcggtgg atagaagcaa ttcctcaga aagctgaagg caccaaaggt 3480
tatatttgtt agcatttcag tgtttgccaa actcagctac agtagagatc acagattccc 3540
tatttcccag agattcaaaa ttcagcagcc cctctctaac tatggctcag agtcgtgtca 3600
ttacatatgc cccaacaaca accccccaccc ctatcctacc cccgcctcac acgtgcaagt 3660
actatcacag ttgccaacct agcagagctg ccatcctaag gtcgaggtcg ccgctttggc 3720
tgtgtgcaca ggcaagcgcc ctcacccaat ggccctggcc ttgctatggg tgcgtgagtt 3780
gagatgatgc tctggactct gaggtgaagg ccactggaac agtgaaaaaa gctaacgcag 3840
ggcttttacc tagtcccctt cctttggtgg tgggtgttta cggaacatat ttgggatctg 3900
agtgtatggt cgcaccacaa taaagcctta acctatatag tagaatttca gctgtaatca 3960
ttaagaactg agattgccac cacccacctc actgtctgtg tcaaccacag caggctggag 4020
cagtcagctc aggaacaggc aaaaccttag gtccctccgc ctacctaacc ttcaatacat 4080
caaggatagg cttctttgct tgcccaaacc tcgccccagt ctagaccacc tggggattcc 4140
cagctcaggg cgaaaaggaa gcccgagaag cattctgtag agggaaatcc tgcatgagtg 4200
cgcccccttt cgttactcca acacatccag caaccactga acttggccgg ggaacacacc 4260
tggtcctcat gcaccagcat tgtgaccatc aacggaaaag tactattgct gcgaccccgc 4320
cccttccgct acaacgcttg gtccgcctga atcccgcccc ttcctccgtt cccagcctca 4380
tcttttttcgt cgtggactct cagtggcctg ggtcctggct gttttctaag cacacccttg 4440
catcttggtt cccgcacgtg ggaggcccat cccggccttg agcacaatga cccgcgctcc 4500
tcgttgcccc gcggtgcgct ctctgctgcg cagccgatac cgggaggtgt ggccgctggc 4560
aacctttgtg cggcgcctgg ggcccgaggg caggcggctt tgcaacccg ggacccgaa 4620
gatctaccgc actttggttg cccaatgcct agtgtgcatg cactggggct cacagcctcc 4680
acctgccgac cttccttcc accaggtggg cctccaggcg ggatccccat gggtcagggg 4740
cggaaagccg ggaggacgtg ggatagtgcg tctagctcat gtgtcaagac cctcttctcc 4800
ttaccaggtg tcatccctga aagagctggt ggccagggtt gtgcagagac tctgcgagcg 4860
caacgagaga aacgtgctgg cttttggctt tgagctgctt aacgaggcca gaggcgggcc 4920
tcccatggcc ttcactagta gcgtgcgtag ctacttgccc aacactgtta ttgagaccct 4980
gcgtgtcagt ggtgcatgga tgctactgtt gagccgagtg ggcgacgacc tgctggtcta 5040
cctgctggca cactgtgctc tttatcttct ggtgccccc agctgtgcct accaggtgtg 5100
tgggtctccc ctgtaccaaa tttgtgccac cacggatatc tggccctctg tgtccgctag 5160
ttacaggccc acccgacccg tgggcaggaa tttcactaac cttaggttct tacaacagat 5220
caagagcagt agtcgccagg aagcaccgaa accccctggcc ttgccatctc gaggtacaaa 5280
gaggcatctg agtctcacca gtacaagtgt gccttcagct aagaaggcca gatgctatcc 5340
```

Figure 5(C)

```
tgtcccgaga gtggaggagg gaccccacag gcaggtgcta ccaaccccat caggcaaatc 5400
atgggtgcca agtcctgctc ggtcccccga ggtgcctact gcagagaaag atttgtcttc 5460
taaaggaaag gtgtctgacc tgagtctctc tgggtcggtg tgctgtaaac acaagcccag 5520
ctccacatct ctgctgtcac caccccgcca aaatgccttt cagctcaggc catttattga 5580
gaccagacat ttcctttact ccaggggaga tggccaagag cgtctaaacc cctcattcct 5640
actcagcaac ctccagccta acttgactgg ggccaggaga ctggtggaga tcatctttct 5700
gggctcaagg cctaggacat caggaccact ctgcaggaca caccgtctat cgcgtcgata 5760
ctggcagatg cggcccctgt tccaacagct gctggtgaac catgcagagt gccaatatgt 5820
cagactcctc aggtcacatt gcaggtttcg aacagcaaac caacaggtga cagatgcctt 5880
gaacaccagc ccaccgcacc tcatggattt gctccgcctg cacagcagtc cctggcaggt 5940
atatggtttt cttcgggcct gtctctgcaa ggtggtgtct gctagtctct ggggtaccag 6000
gcacaatgag cgccgcttct ttaagaactt aaagaagttc atctcgttgg ggaaatacgg 6060
caagctatca ctgcaggaac tgatgtggaa gatgaaagta gaggattgcc actggctccg 6120
cagcagcccg ggtgagcatg gctggtctcc agctgaatgc attaggggcc cagaaaaggg 6180
agacaatggg tggcagtaac ccaggtcccc agtggtgtgg tggctttatg cagtccgtgg 6240
ttggatgagt tccatcttat ggtctctgac tccaagctcc ctccagctcg ccttgcacaa 6300
actaagattc ttgtccaagc cctgggcagg ttctcagggc tggggacatt gtggtgaaca 6360
gataagcaga cggggagcat ggtggatagg agttctggca cagtgcacca gagagagtct 6420
ggaagcgcta gtgagagcta atgtaagggc ccgtggttcg ccaaagaatg ataacccgg 6480
actcaaatag tatgccaaag caaggagcat ttcattctgc agaaatcaag catgcaggtg 6540
ggggggggg gttgctctca ttccaagatg gagagacaac caagtataga ttttaagggg 6600
atcgggggcc tttatcttac tccatctcta ggggcattcc attactgggg catggggttg 6660
gaggttggaa actgttaatg gggaggtctg gaaacttgct gccccattgt ccttgcttca 6720
ggctaggtag ctgagtagct tctaatggca ggatagtttc tgactagctg tctaaagtct 6780
ggggtgtttg ttttttttgtt ttttctagta acttacttgc ctgaacttgc tcagttttta 6840
ggcctggtct cctggactgc caatttgaag cctattaagg agtcagcctg tctcactact 6900
ccaggttatc tataatcccc ctgtagaacg gtacctcact gataacaatg acagaccaac 6960
ataggaaccc actatccttg tggtgcatga gtttcaaagg ttcttctggt cctcccagtg 7020
tgcagatcca tgcttaagct atggtcctcc cagtgtgcag atccgtgctt aagctatggt 7080
cttgcagctg ctcgatctac aaagggtagg gtgaacgaag gaaagataaa tgaaaaaaaa 7140
aaaactgttt cctacagtga agatcgctgc cccatcttag ctatgagaag ggactgggga 7200
gtggagcctg gtgcataaaa gaggattgtg ttacttggaa ggctgcagag cctggactcc 7260
tgtgccctcc ttgcctggtt ttctgggttt aatgttgagg ttggccctct gtagtcacta 7320
cctgacccct tcccttttcag ccaaccctcc ggttacaccc tgtgcatgta tggaaggggc 7380
caaacgccct atcctgctct cccttcccca aaattcttag gatattaaca acttatgggg 7440
aaaagatggt agagctatgt ttacccacca tgtacttggg aagctccgaa gtaagctt 7498
``` ated as WO 98/14593 on Apr. 9, 1998); which is a
TELOMERASE PROMOTER DRIVING EXPRESSION OF THERAPEUTIC GENE SEQUENCES

RELATED APPLICATIONS

This application is a continuation-in-part of U.S. Ser. No. 08/974,584 (filed Nov. 19, 1997, pending); and U.S. Ser. No. 08/974,549 (filed Nov. 19, 1997, now U.S. Pat. No. 6,166, 178); which are continuations-in-part of U.S. Ser. No. 09/402,181 (now U.S. Pat. No. 6,610,839), which is the U.S. Nation Stage of PCT/US97/17885 (filed Oct. 1, 1997, published as WO 98/14593 on Apr. 9, 1998); which is a continuation-in-part of U.S. Ser. No. 08/911,312 (filed Aug. 14, 1997, abandoned); and Ser. No. 08/912,051 (filed Aug. 14, 1997, now U.S. Pat. No. 6,475,789).

The following applications are explicitly incorporated herein by reference in their entirety and for all purposes: U.S. applications Ser. No. 08/724,643 (abandoned); Ser. No. 08/844,419 (abandoned); Ser. No. 08/846,017 (abandoned); Ser. No. 08/851,843 (now U.S. Pat. No. 6,093,809); Ser. No. 08/854,050 (now U.S. Pat. No. 6,261,836); Ser. No. 08/911, 312 (abandoned); Ser. No. 08/912,951 (now U.S. Pat. No. 6,475,789); Ser. No. 08/915,503 (abandoned); Ser. No. 08/974,584 (pending); Ser. No. 08/974,549 (now U.S. Pat. No. 6,166,178); Ser. No. 08/979,742 (abandoned); and Ser. No. 09/042,460 (pending); and International Applications PCT/US97/17618 (WO 98/14592) and PCT/US97/17885 (WO 98/14593).

STATEMENT AS TO RIGHTS TO INVENTIONS MADE UNDER FEDERALLY SPONSORED RESEARCH AND DEVELOPMENT

This invention was made with United States Government support under Grant Nos. HD/CA 34880; 5T32GM07491; R01HD28317, R01EY09300, R01EY11267; all awarded by the National Institute of Health. The United States Government has certain rights in this invention.

FIELD OF THE INVENTION

The present invention is related to novel nucleic acids comprising telomerase reverse transcriptase (TERT, or TRT) cis-acting transcriptional control sequences. The present invention is further directed to methods of using these cis-acting transcriptional control sequences, for example, to drive heterologous gene sequences; to modulate the level of transcription of TERT or to isolate novel trans-acting regulatory factors which bind to and modulate the activity of a TERT promoter.

BACKGROUND OF THE INVENTION

The following discussion is intended to introduce the field of the present invention to the reader. The citation of various references in this section is not to be construed as an admission of prior invention.

It has long been recognized that complete replication of the ends of eukaryotic chromosomes requires specialized cell components (Watson (1972) Nature New Biol. 239:197; Olovnikov (1973) J. Theor. Biol. 41:181). Replication of a linear DNA strand by conventional DNA polymerases requires an RNA primer, and can proceed only 5' to 3'. When the RNA primer bound at the extreme 5' ends of eukaryotic chromosomal DNA strands is removed, a gap is introduced, leading to a progressive shortening of daughter strands with each round of replication. This shortening of telomeres, the protein-DNA structures physically located on the ends of chromosomes, is thought to account for the phenomenon of cellular senescence or aging of normal human somatic cells in vitro and in vivo (see, e.g., Goldstein (1990) Science 249:1129; Martin (1979) Lab. Invest. 23:86; Goldstein (1969) Proc. Natl. Acad. Sci. USA 64:155; Schneider (1976) Proc. Natl. Acad. Sci. USA, 73:3584; Harley (1990) Nature 345:458–460; Hastie (1990) Nature 346:866–868; Counter (1992) EMBO J. 11:1921–1929; Bodnar (1998) Science 279:349–52).

The length and integrity of telomeres is thus related to entry of a cell into a senescent stage (i.e., loss of proliferative capacity). Moreover, the ability of a cell to maintain (or increase) telomere length may allow a cell to escape senescence, i.e., to become immortal.

The maintenance of telomeres is a function of a specific DNA polymerase known as telomerase reverse transcriptase (TERT, or TRT). Telomerase is a ribonucleoprotein (RNP) that uses a portion of its RNA moiety as a template for telomere repeat DNA synthesis (see, e.g., Morin (1997) Eur. J. Cancer 33:750). Consistent with the relationship of telomeres and TERT to the proliferative capacity of a cell (i.e., the ability of the cell to divide indefinitely), telomerase activity is detected in immortal cell lines and an extraordinarily diverse set of tumor tissues, but is not detected (i.e., was absent or below the assay threshold) in normal somatic cell cultures or normal tissues adjacent to a tumor (see, U.S. Pat. Nos. 5,629,154; 5,489,508; 5,648,215; and 5,639,613; see also, Morin (1989) Cell 59:521; Shay (1997) Eur. J. Cancer 33:787; Kim (1994) Science 266:2011). Moreover, a correlation between the level of telomerase activity in a tumor and the likely clinical outcome of the patient has been reported (see e.g., U.S. Pat. No. 5,639,613; Langford (1997) Hum. Pathol. 28:416).

Telomerase activity has also been detected in human germ cells, proliferating stem or progenitor cells, and activated lymphocytes. In somatic stem or progenitor cells, and in activated lymphocytes, telomerase activity is typically either very low or only transiently expressed (see, e.g., Chiu (1996) Stem Cells 14:239; Bodnar (1996) Exp. Cell Res. 228:58; Taylor (1996) J. Invest. Dermatol. 106:759).

Accordingly, human TERT (hTERT, hTRT) is an ideal target for treating human diseases relating to cellular proliferation and senescence, such as cancer. The cis-acting transcriptional control elements of TERT provided herein also allow for the identification of trans-acting transcription control factors. Moreover, the discovery and characterization of the TERT cis-acting sequences provide opportunities to develop useful disease therapies. The present invention fulfills this and other needs.

SUMMARY OF THE INVENTION

The invention provides an isolated, synthetic, or recombinant polynucleotide comprising a human telomerase reverse transcriptase (hTERT) promoter sequence. In alternative embodiments, the promoter sequence comprises at least 15, 50, 100, 150, 200, 250, 500, 1000, 2500 or at least 13,000 bases as set forth in residues 44 to 13490 in SEQ ID NO:1 or SEQ ID NO:2. Other embodiments include sequences starting within about one to 5 nucleotides of a translation start codon and ending at about 50, 100, 150, 200, 250, 500, 1000, 2500 or 13500 nucleotides upstream of the translation start codon in SEQ ID NO:1 or SEQ ID NO:2. The promoter sequence can comprise the sequence as set forth in residues 44 to 13490 in SEQ ID NO: 1.

The invention provides an isolated, synthetic, or recombinant polynucleotide comprising a human telomerase reverse transcriptase (hTERT) promoter or a mouse telomerase reverse transcriptase (mTERT) sequence operably linked to a transcribable sequence. The transcribable sequence can encode a protein other than hTERT or mTERT. The protein can be a cellular toxin. In one embodiment, the protein has activity that is not itself toxic to a cell, but which renders the cell sensitive to an otherwise nontoxic drug; e.g., the protein can be a Herpes virus thymidine kinase. Alternatively, the transcribable sequence can encode a protein that is detectable by fluorescence, phosphorescence, or by virtue of its possessing an enzymatic activity. The detectable protein can be firefly luciferase, alpha-glucuronidase, alpha-galactosidase, chloramphenicol acetyl transferase, green fluorescent protein, enhanced green fluorescent protein, and the human secreted alkaline phosphatase.

The invention also provides a method for screening for a compound that binds to TERT promoter, such as an hTERT or an mTERT promoter, comprising the following steps: (i) providing an isolated, synthetic, or recombinant polynucleotide comprising a TERT promoter sequence and a test compound, (ii) contacting the polynucleotide with the test compound, and (iii) measuring the ability of the test compound to bind to the polynucleotide.

The invention also provides a method for a method for screening for a compound that modulates a TERT promoter, such as hTERT or mTERT promoter activity, comprising the following steps (i) providing a first polynucleotide comprising an isolated, synthetic, or recombinant TERT promoter sequence operably linked to a transcribable second nucleotide, and a test compound, (ii) contacting the polynucleotide with the test compound, and (iii) measuring the ability of the test compound to modulate transcription of the second nucleotide. The transcribable sequence can encode a protein. The protein can be detectable by fluorescence or phosphorescence or by virtue of its possessing an enzymatic activity. The detectable protein can be firefly luciferase, alpha-glucuronidase, alpha-galactosidase, chloramphenicol acetyl transferase, green fluorescent protein, enhanced green fluorescent protein, and the human secreted alkaline phosphatase.

The invention also provides a method for identifying a cis-acting transcriptional regulatory sequence that modulates a TERT promoter, such as hTERT or mTERT, promoter activity, comprising the following steps (i) providing a first construct comprising a first polynucleotide comprising an isolated, synthetic, or recombinant TERT promoter sequence operably linked to a transcribable second nucleotide, (ii) providing a second construct comprising a modification in a subsequence of the first polynucleotide of step 1 operably linked to a transcribable second nucleotide, and (iii) measuring independently under the same conditions the ability of the first construct and the second construct to induce transcription of the transcribable second nucleotide, wherein an increase or decrease in the ability of the second modified construct to induce transcription of the transcribable second nucleotide as compared to the first unmodified construct identifies in the second modified construct a subsequence acting functionally as a cis-acting transcriptional regulatory sequence that modulates TERT promoter activity.

The invention also provides a method for generating a cell that lacks a TERT promoter activity, comprising the following steps (i) providing a polynucleotide comprising an isolated, synthetic, or recombinant TERT promoter sequence; (ii) introducing into the cell the polynucleotide of step (i), and (iii) measuring ability of the cell to transcribe TERT message; wherein the inability of the cell to transcribe TERT message indicates that a cell that lacks TERT promoter activity has been generated.

The invention also provides a genetically engineered cell lacking TERT, e.g., hTERT or mTERT, promoter activity, produced by introducing into the cell a polynucleotide comprising an isolated, synthetic, or recombinant TERT promoter sequence.

The invention also provides a composition comprising an isolated nucleic acid molecule comprising a TERT promoter, wherein the promoter comprises about 100 to about 200, 200 to about 400, 400 to about 900, or 900 to about 2500, or 2500 to about 5000 nucleotides upstream of a transcriptional start site in SEQ ID NO:1 or SEQ ID NO:2.

The invention also provides a vector comprising a TERT promoter operably linked to a heterologous nucleic acid sequence, wherein the promoter comprises about 100 to about 200, 200 to about 400, 400 to about 900, or 900 to about 2500, or 2500 to about 5000 nucleotides upstream of a transcriptional start site in SEQ ID NO:1 or SEQ ID NO:2.

The invention provides a transformed cell comprising a TERT promoter operably linked to a heterologous nucleic acid sequence, wherein the promoter comprises about 100 to about 200, 200 to about 400, 400 to about 900, or 900 to about 2500, or 2500 to about 5000 nucleotides upstream of a transcriptional start site in SEQ ID NO:1 or SEQ ID NO:2. The heterologous nucleic acid can code for a cellular toxin. The cellular toxin can be a Herpes virus thymidine kinase, ricin, abrin, diphtheria, gelonin, Pseudomonas exotoxin A, tumor necrosis factor alpha (TNF-alpha), *Crotalus durissus terrificus* toxin, *Crotalus adamenteus* toxin, *Naja naja* toxin, and *Naja mocambique* toxin.

The invention also provides a method of expressing a heterologous nucleic acid sequence in a cell comprising: (a) transforming said cell with a vector or an expression cassette comprising a TERT promoter, wherein the promoter consists of about 100 to about 200, 200 to about 400, 400 to about 900, or 900 to about 2500, or 2500 to about 5000 nucleotides upstream of a transcriptional start site in SEQ ID NO:1 or SEQ ID NO:2, and wherein the promoter is operably linked to the heterologous nucleic acid sequence; and (b) growing said cell under conditions where the heterologous nucleic acid sequence is expressed in said cell.

The invention also provides an isolated nucleic acid molecule which hybridizes to SEQ ID NO:1 or SEQ ID NO:2 under stringent hybridization conditions. The nucleic acid can consist of about 100 to about 200, 200 to about 400, 400 to about 900, or 900 to about 2500, or 2500 to about 5000 nucleotides upstream of a transcriptional start site in SEQ ID NO:1 or SEQ ID NO:2. The stringent hybridization conditions can comprise a hybridization step comprising a salt concentration of about 0.02 molar at pH 7 and a temperature of about 60° C. The stringent hybridization conditions can also comprise a washing step at 65° C. in 0.1×SSC, 0.1% SDS. In an alternative embodiment, the stringent hybridization conditions are selected to be about 5–10° C. lower than the thermal melting point (Tm) for the specific sequence at a defined ionic strength and pH.

The invention also provides transgenic non-human animals comprising a TERT promoter sequence operably linked to transcribable sequence, such as a reporter gene. In a preferred embodiment, an hTERT promoter is operably linked to a reporter gene in a transgenic mouse.

A further understanding of the nature and advantages of the present invention may be realized by reference to the remaining portions of the specification, the figures and claims.

All publications, GenBank deposited sequences, ATCC deposits, patents and patent applications cited herein are hereby expressly incorporated by reference for all purposes.

BRIEF DESCRIPTION OF THE DRAWINGS

FIG. 2 shows the sequence of a Not 1 fragment (SEQ ID NO:1) from the lambda Gphi5 insert containing the hTERT promoter region.

FIG. 4A shows, in the upper panel, sequence alignment of the murine (SEQ ID NO:18) and human (SEQ ID NO:17) TERT promoters. Also shown are the positions of conserved cis-acting transcriptional regulatory motifs, including the motifs designated as the "E-box" or "Myc/Max binding site" and SP1 sites. E-boxes are indicated by shaded ("shaded") sequence. SP1 sites are indicated by underlines. FIG. 4A, lower panel, illustrates the proximal sequences of the 2.5 kb hTERT (SEQ ID NO:19) and E-box reporter (SEQ ID NO:20) constructs, including the region deleted in the E-box reporter construct, (SEQ ID NO:21) as described below in Example 8.

FIG. 5 shows the sequence of the mouse telomerase reverse transcriptase promoter sequence (SEQ ID NO:2).

DETAILED DESCRIPTION OF THE INVENTION

Figure 1:
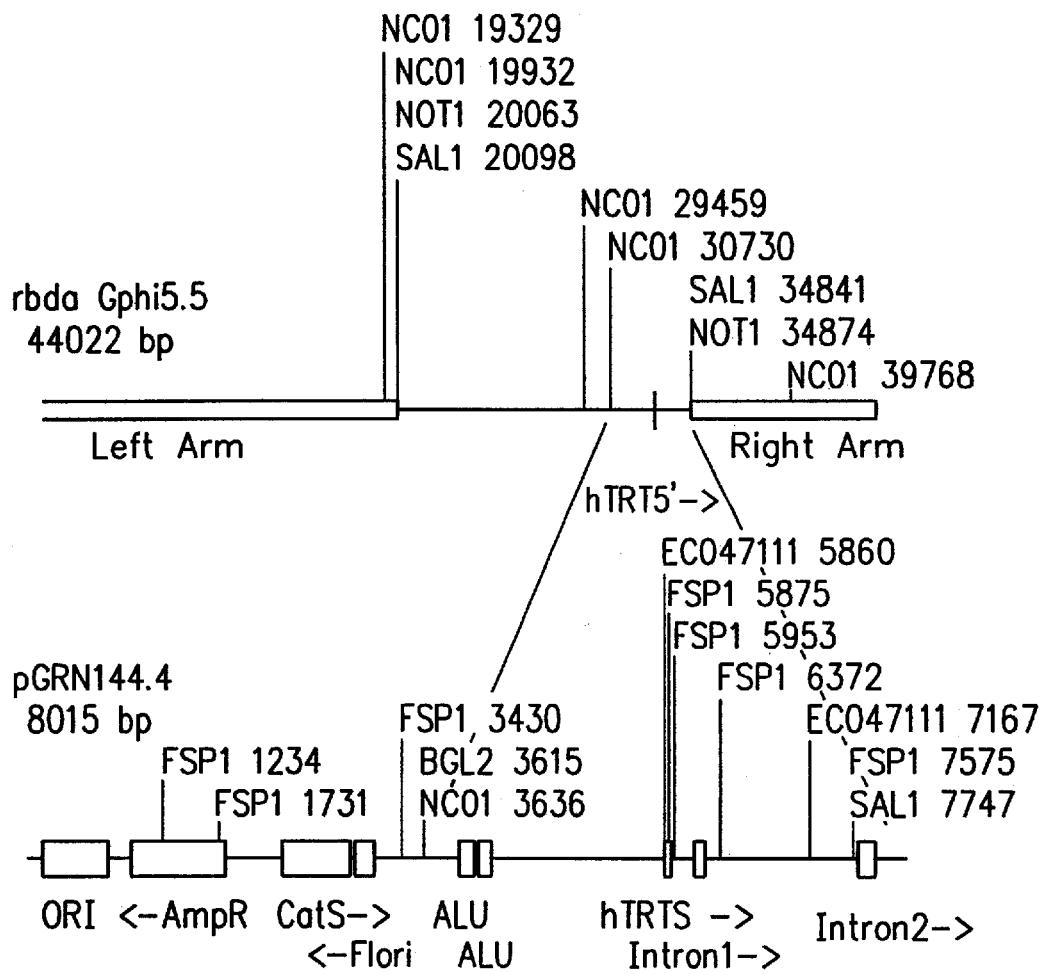
FIG. 1 shows a restriction map of lambda phage clone Gphi5, discussed in detail in Example 1, below.

The invention provides novel isolated polynucleotides comprising cis-acting transcriptional control sequences of telomerase reverse transcriptase genes. The polynucleotides of the invention include those based on or derived from genomic sequences of untranscribed, transcribed and intronic regions of TERT genes, including the human TERT (hTERT) and mouse TERT (mTERT) genes. Cis-acting TERT transcriptional control sequences, also referred to as the "TERT promoter sequences," include all cis-acting TERT transcriptional control elements and regulatory sequences, including (without limitation) those that regulate and modulate timing and rates of transcription of the TERT gene. Thus, the TERT promoter sequences of the invention include cis-acting elements such as, e.g., promoters, enhancers, transcription terminators, origins of replication, chromosomal integration sequences, introns, exons, and 5' and 3' untranslated regions, with which proteins or other biomolecules interact to carry out and regulate transcription of the TERT transcript.

Isolating and Characterizing Human TERT Promoter Sequences

As described in Example 1, the hTERT promoter (SEQ ID NO:1) was obtained by sequencing an insert from a lambda phage isolated from a human genomic library. This lambda clone is designated "Gϕ5". It was deposited under terms of the Budapest Treaty with the American Type Culture Collection (ATCC), 10801 University Blvd., Manassas, Va. 20110-2209 U.S.A., on Aug. 14, 1997, under Accession No. 98505. Lambda Gϕ5 contains a 15.3 kilobasepair (kbp) insert including approximately 13,500 bases 5' (upstream) to the hTERT coding sequence (i.e., 5' untranscribed promoter sequence). These hTERT promoter sequences were further subcloned into plasmids. A Not1 fragment (SEQ ID NO:1) from lambda Gphi5 containing the hTERT promoter sequences was subcloned in opposite orientations into the Not1 site of pUC derived plasmids (designated pGRN142 and pGRN143, respectively, (see discussion below) and pGRN142 was sequenced.

In SEQ ID NO:1, the hTERT genomic insert begins at residue 44 and ends at residue 15375. The hTERT cDNA start site is at residue 13490. The hTERT ATG codon starts at residue 13545. Thus, untranscribed hTERT promoter sequences of the invention lie downstream of residue 44 and upstream of residue 13489 of SEQ ID NO:1. In immortal cells, a reporter gene driven by a sequence upstream of the TERT coding sequence drove expression as efficiently as the positive control (containing an SV40 early promoter and enhancer).

TERT promoter sequences (i.e., TERT genomic sequences capable of driving transcription in a telomerase activity positive cell) of the invention also include intronic sequences.

Identification of Cis-Acting Transcriptional Regulatory Sequences in the Human and Mouse TERT Promoter To identify cis-acting transcriptional regulatory sequences in human TERT (hTERT) and mouse TERT (mTERT) sequences 5' to their respective TERT coding sequence, the human and mouse promoter sequences were analyzed for sequence identity between themselves and publicly accessible sequences (see Example 8, below). Alignment of the first 300 bases upstream of the human and mouse coding sequences indicated a number of conserved regions, i.e. putative cis-acting transcriptional regulatory sequences (see FIG. 4A).

In particular, located at residues −34 to −29 upstream of the human TERT translation start site (ATG, A at 13545 of SEQ ID NO:1) and at residues −32 to −27 upstream of the mouse TERT translation start site (ATG) are highly conserved motifs. They correspond to a cis-acting motif known to interact with c-Myc, the so-called "E-box" or "Myc/Max binding site." Specifically, they are highly conserved with respect to the core nucleotides which comprise the E-box, nucleotides flanking the E-box and position of the E-box relative to the translation start site. A second E-box was identified at residues −242 to −237 upstream of the human TERT translation start site. This second E-box was not conserved in the mouse promoter. These observations support the finding (see discussion on E-box deletion construct experiments, below) that the conserved Myc binding site, by interacting with c-Myc as a trans-acting transcriptional regulatory factor, plays a major role in TERT promoter regulation and telomerase expression.

Sequence alignment identified additional conserved cis-acting transcriptional regulatory elements in the TERT gene promoter. For example, two SP1 binding sites, located at residue −168 to −159 and residue −133 to −121 relative to the TERT translation start site (FIG. 4A) were identified, which are highly conserved between the mouse and human TERT promoters.

Binding sites (cis-acting sequences) for a number of other transcription factors, including the sex determining region Y gene product (SRY), hepatic nuclear factors 3-beta (HNF-3_) and 5 (HNF-5), TFIID-MBP, E2F and c-Myb were also found within this region of both the mouse and human promoters.

TERT-Specific Promoter Motif Identified

Figure 4B:
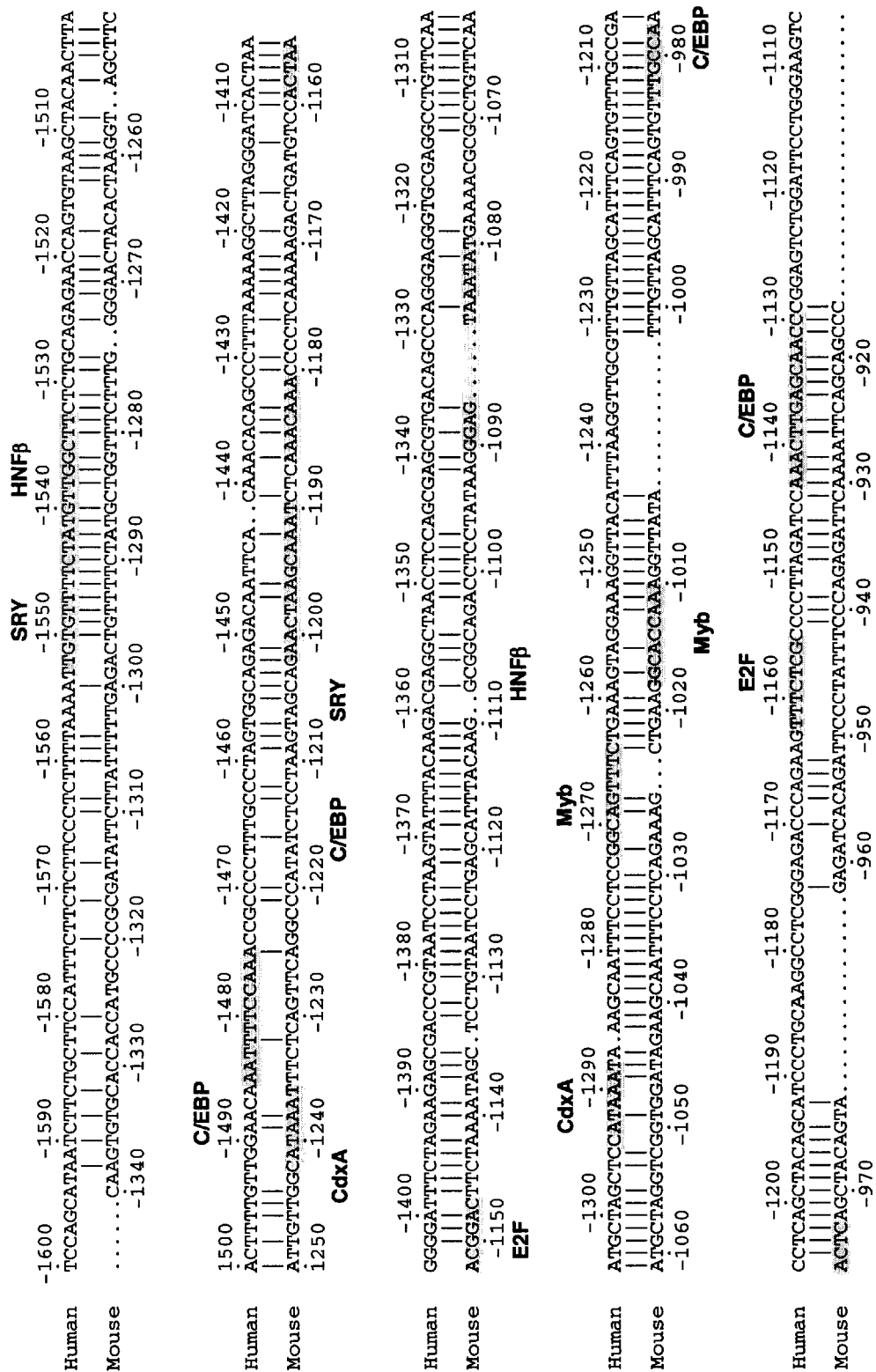
FIG. 4B shows the alignment of human (SEQ ID NO:22) (residues −1106 to −1612) and mouse (SEQ ID NO:23) (residues −916 to −1340) TERT promoter sequences. Alignments were performed and identity calculated as described in Example 8. Cis-acting transcriptional regulatory elements common to both TERT promoters are indicated by shaded regions.

Further analysis of the human and mouse TERT promoter sequences indicated other regions of sequence conservation. In particular, a region with a high degree of sequence identity between human and mouse promoter was found between residue −1106 and residue −1602 upstream of the human TERT translation start site and residue −916 and residue −1340 upstream of the mouse TERT translation start site (FIG. 4B). Thus, the invention provides cis-acting sequences specific for the modulation of TERT transcription.

In a preferred embodiment, the methods of the invention use these human and mouse TERT-specific transcriptional regulatory motifs to identify and isolate TERT-specific, and other, trans-acting transcriptional regulatory factors (as described in detail below).

Screening and Isolating Trans-Acting TERT Transcriptional Modulators

The invention also provides the reagents and methods for screening and isolating trans-acting TERT transcriptional regulatory factors. Alternative embodiments include novel in vitro and cell-based in vivo assay systems to screen for TERT promoter binding agents (trans-acting TERT transcriptional regulatory factors) using the nucleic acids of the invention.

Many assays are available that screen for nucleic acid binding proteins and all are adapted and used with the novel TERT sequences provided by the invention, as described below.

c-Myc Acts as a Potent Activator of TERT Gene Transcription

Use of recombinant constructs comprising TERT promoter sequences of the invention has, for the first time, demonstrated that c-Myc acts as a potent activator of telomerase activity by direct interaction with cis-acting regulatory sequences in the TERT promoter. c-Myc acts through the rapid upregulation of hTERT gene expression (see Example 8, below). Significantly, the studies demonstrate that transcriptional activation of the hTERT promoter by c-Myc can be abrogated by deletion or mutation of a single cis-acting regulatory sequence, the "Myc/Max binding site," within the hTERT promoter. Furthermore, also as discussed below, the ability of an inducible c-Myc to enhance expression of hTERT is resistant to inhibition of protein synthesis.

Screening for Small Molecules and Biological Agents which are Modulators of the TERT Promoter The invention also provides constructs, cell lines and methods for screening for small molecule modulators of TERT promoter activity in vitro and in vivo. Many assays are available that screen for small molecule modulators of TERT transcription, including high throughput assays; all are adapted and used with the novel TERT sequences provided by the invention.

As described in detail in Example 5, below, various constructs containing hTERT promoter sequences driving a marker gene (in this example, the human secreted alkaline phosphatase, SEAP, gene) indicated that a fragment of approximately 2.5 kb of hTERT promoter sequence contains sufficient sequence elements to support both activation and repression of gene expression in response to proliferation and/or growth arrest stimuli that control telomerase activity in a model cell line, IDH4. Clones were selected and expanded for high throughput screening of small molecule activators of telomerase.

TERT Promoter used to Drive Heterologous Gene Sequences

The invention also provides constructs in which the TERT promoter sequences of the invention are operably linked to a heterologous gene (in a preferred embodiment, a structural gene). In this way the heterologous gene is transcribed in the same cells at the same time the natural TERT transcript would be expressed. Thus, when the construct is expressed in a transformed cell or transgenic (non-human) animal, the heterologous gene (and protein, if the gene is a coding sequence) is expressed in the same temporal pattern over the same cell range as the wild type, TERT promoter-driven TERT gene.

These constructs are useful for TERT promoter-based assays, for example, to identify biological modulators of TERT and telomerase activity. In alternative embodiments, the heterologous coding sequence operably linked to a TERT promoter of the invention is a marker gene (e.g., alkaline phosphatase, SEAP; β-galactosidase), a modified TERT structural gene or a TERT antisense, a therapeutic gene (e.g., a "cancer cell cytotoxic gene" as thymidine kinase).

In a further embodiment, cytopathic viruses are provided, in particular human cytopathic viruses, such as modified adenovirus or Herpes virus. Viruses, such as adenovirus or Herpes virus require essential virally encoded genes to proliferate and lyse specific cells. If any one of these essential viral genes were modified such that expression of the essential element would be driven by the TERT promoter, proliferation of the virus, and its cytopathic effects, would be restricted to telomerase-expressing cells, in particular tumor cells.

Definitions

The following terms are defined infra to provide additional guidance to one of skill in the practice of the invention.

As used herein, the terms "allele" or "allelic sequence" refer to an alternative form of a nucleic acid sequence (i.e., a nucleic acid corresponding to a TERT promoter, particularly, an hTERT promoter). Alleles result from mutations (i.e., changes in the nucleic acid sequence), and can produce differently regulated mRNAs. Common mutational changes that give rise to alleles are generally ascribed to natural deletions, additions, or substitutions of nucleotides. Each of these types of changes may occur alone, in combination with the others, or one or more times within a given gene, chromosome or other cellular nucleic acid. Thus, the term "TERT promoter" includes allelic forms of TERT promoter sequences, i.e., TERT cis-acting transcriptional control elements, including, e.g., the exemplary human and mouse sequences described herein.

The term "amplifying" as used herein incorporates its common usage and refers to the use of any suitable amplification methodology for generating or detecting recombinant or naturally expressed nucleic acid, as described in detail, below. For example, the invention provides methods and reagents (e.g., specific oligonucleotide PCR primer pairs) for amplifying (e.g., by PCR) naturally expressed or recombinant nucleic acids of the invention (e.g., TERT promoter sequences of the invention) in vivo or in vitro. An indication that two polynucleotides are "substantially identical" can be obtained by amplifying one of the polynucleotides with a pair of oligonucleotide primers or pool of degenerate primers (e.g., fragments of an TERT promoter sequence) and then using the product as a probe under stringent hybridization conditions to isolate the second sequence (e.g., the TERT promoter sequence) from a genomic library or to identify the second sequence in, e.g., a Northern or Southern blot.

As used herein, the term "TERT promoter" includes any TERT genomic sequences capable of driving transcription in a telomerase activity positive cells. Thus, TERT promoters of the invention include without limitation cis-acting transcriptional control elements and regulatory sequences that are involved in regulating or modulating the timing and/or rate of transcription of a TERT gene. For example, the TERT promoter of the invention comprises cis-acting transcriptional control elements, including enhancers, promoters, transcription terminators, origins of replication, chromosomal integration sequences, 5' and 3' untranslated regions, exons and introns, which are involved in transcriptional regulation. These cis-acting sequences typically interact with proteins or other biomolecules to carry out (turn on/off, regulate, modulate, etc.) transcription.

In alternative embodiments, the TERT promoter sequence comprises TERT sequences 5' (upstream) of the translational start site (ATG), for example, in one embodiment, the hTERT promoter comprises residues 44 to 13545 of SEQ ID NO:1. Other embodiments include sequences starting within about one to 5 nucleotides of a translation start codon (for example in SEQ ID NO:1 or SEQ ID NO:2) and ending at about 50, 100, 150, 200, 250, 500, 1000, 2500 or 13500 nucleotides upstream of the translation start codon. Such embodiments can optionally include other regulatory sequences, such as, exon and/or intron sequences. Another embodiment includes TERT intronic sequences with regulatory activity, as described in Example 2, below. hTERT promoters of the invention also include sequences substantially identical (as defined herein) to an exemplary hTERT promoter sequence of the invention, having the sequence set forth by SEQ ID NO:1. Similarly, mTERT promoters of the invention also include sequences substantially identical to an exemplary mTERT promoter sequence of the invention, having the sequence set forth by SEQ ID NO:2.

The term "heterologous" when used with reference to portions of a nucleic acid, indicates that the nucleic acid comprises two or more subsequences which are not found in the same relationship to each other in nature. For instance, the nucleic acid is typically recombinantly produced, having two or more sequences from unrelated genes arranged in a manner not found in nature; e.g., a promoter sequence of the invention operably linked to a polypeptide coding sequence that, when operably linked, does not reform the naturally occuring TERT gene. For example, the invention provides recombinant constructs (expression cassettes, vectors, viruses, and the like) comprising various combinations of promoters of the invention, or subsequences thereof, and heterologous coding sequences, many examples of which are described in detail below.

As used herein, "isolated," when referring to a molecule or composition, such as, e.g., an hTERT promoter sequence, means that the molecule or composition is separated from at least one other compound, such as a protein, DNA, RNA, or other contaminants with which it is associated in vivo or in its naturally occurring state. Thus, a nucleic acid sequence is considered isolated when it has been isolated from any other component with which it is naturally associated. An isolated composition can, however, also be substantially pure. An isolated composition can be in a homogeneous state. It can be in a dry or an aqueous solution. Purity and homogeneity can be determined, e.g., using analytical chemistry techniques such as, e.g., polyacrylamide gel electrophoresis (PAGE), agarose gel electrophoresis or high pressure liquid chromatography (HPLC).

As used herein, the terms "nucleic acid" and "polynucleotide" are used interchangeably, and include oligonucleotides (i.e., short polynucleotides). They also refer to synthetic and/or non-naturally occurring nucleic acids (i.e., comprising nucleic acid analogues or modified backbone residues or linkages). The terms also refer to deoxyribonucleotide or ribonucleotide oligonucleotides in either single-or double-standed form. The terms encompass nucleic acids containing known analogues of natural nucleotides. The term also encompasses nucleic acid-like structures with synthetic backbones. DNA backbone analogues provided by the invention include phosphodiester, phosphorothioate, phosphorodithioate, methyl-phosphonate, phosphoramidate, alkyl phosphotriester, sulfamate, 3'-thioacetal, methylene (methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923–1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) Toxicol. Appl. Pharmacol. 144:189–197. Other synthetic backbones encompassed by the term include methylphosphonate linkages or alternating methylphosphonate and phosphodiester linkages (Strauss-Soukup (1997) Biochemistry 36:8692–8698), and benzyl-phosphonate linkages (Samstag (1996) Antisense Nucleic Acid Drug Dev 6:153–156).

As used herein, the term "operably linked" refers to a functional relationship between two or more nucleic acid (e.g., DNA) segments. Typically, it refers to the functional relationship of a transcriptional regulatory sequence to a transcribed sequence. For example, a TERT promoter sequence of the invention, including any combination of cis-acting transcriptional control elements, is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant means" also encompass the ligation of nucleic acids having coding or promoter sequences from different sources into an expression cassette or vector for expression of, e.g., a fusion protein; or, inducible, constitutive expression of a protein (i.e., a TERT promoter of the invention operably linked to a heterologous nucleotide, such as a polypeptide coding sequence).

As used herein, the "sequence" of a gene (unless specifically stated otherwise) or nucleic acid refers to the order of nucleotides in the polynucleotide, including either or both strands of a double-stranded DNA molecule, e.g., the sequence of both the coding strand and its complement, or of a single-stranded nucleic acid molecule. For example, in alternative embodiments, the promoter of the invention comprises untranscribed, untranslated, and intronic TERT sequences, e.g., as set forth in the exemplary SEQ ID NO:1 and SEQ ID NO:2.

As used herein, the term "transcribable sequence" refers to any sequence which, when operably linked to a cis-acting transcriptional control element, e.g., a promoter, such as the TERT promoters of the invention, and when placed in the appropriate conditions, is capable of being transcribed to generate RNA, e.g., messenger RNA (mRNA).

The terms "identical" or percent "identity," in the context of two or more nucleic acids or polypeptide sequences, refer to two or more sequences or subsequences that are the same or have a specified percentage of nucleotides (or amino acid residues) that are the same, when compared and aligned for maximum correspondence over a comparison window, as measured using one of the following sequence comparison algorithms or by manual alignment and visual inspection. This definition also refers to the complement of a sequence. For example, in alternative embodiments, nucleic acids within the scope of the invention include those with a nucleotide sequence identity that is at least about 60%, at least about 75–80%, about 90%, and about 95% of the exemplary TERT promoter sequence set forth in SEQ ID NO:1 (including residues 44 to 13544 of SEQ ID NO:1) or SEQ ID NO:2, and the intronic TERT sequences capable of driving a reporter gene in telomerase positive cells, as described below. Two sequences with these levels of identity are "substantially identical." Thus, if a sequence has the requisite sequence identity to a TERT promoter sequence or subsequence of the invention, it also is a TERT promoter sequence within the scope of the invention. Preferably, the percent identity exists over a region of the sequence that is at least about 25 nucleotides in length, more preferably over a region that is at least about 50–100 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identity for the test sequence(s) relative to the reference sequence, based on the designated or default program parameters. A "comparison window", as used herein, includes reference to a segment of any one of the number of contiguous positions selected from the group consisting of from 25 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendrogram showing the clustering relationships used to create the alignment. PILEUP uses a simplification of the progressive alignment method of Feng & Doolittle, J. Mol. Evol. 35:351–360 (1987). The method used is similar to the method described by Higgins & Sharp, CABIOS 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence (e.g., a TERT promoter sequence of the invention as set forth by. e.g., SEQ ID NO:1 or SEQ ID NO:2) is compared to another sequence to determine the percent sequence identity relationship (i.e., that the second sequence is substantially identical and within the scope of the invention) using the following parameters: default gap weight (3.00), default gap length weight (0.10), and weighted end gaps. PILEUP can be obtained from the GCG sequence analysis software package, e.g., version 7.0 (Devereaux (1984) Nuc. Acids Res. 12:387–395).

Another example of algorithm that is suitable for determining percent sequence identity (i.e., substantial similarity or identity) is the BLAST algorithm, which is described in Altschul (1990) J. Mol. Biol. 215:403–410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990) supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues, always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. In one embodiment, to determine if a nucleic acid sequence is within the scope of the invention, the BLASTN program (for nucleotide sequences) is used incorporating as defaults a wordlength (W) of 11, an expectation (E) of 10, M-5, N-4, and a comparison of both strands. For amino acid sequences, the BLASTP program uses as default parameters a wordlength (W) of 3, an expectation (E) of 10, and the BLOSUM62 scoring matrix (see, e.g., Henikoff (1989) Proc. Natl. Acad. Sci. USA 89:10915).

The BLAST algorithm also performs a statistical analysis of the similarity between two sequences (see, e.g., Karlin (1993) Proc. Nat'l. Acad. Sci. USA 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The phrase "selectively (or specifically) hybridizes to" refers to the binding, duplexing, or hybridizing of a molecule to a particular nucleotide sequence under stringent hybridization conditions when that sequence is present in a complex mixture (e.g., total cellular or library DNA or RNA), wherein the particular nucleotide sequence is detected at least twice background, preferably 10 times background. In one embodiment, a nucleic acid can be determined to be within the scope of the invention (e.g., is substantially identical to an hTERT promoter of the invention, as exemplified by residues 44 to 13544 of SEQ ID NO:1, or, SEQ ID NO:2, or, by an intronic promoter sequence, as described below) by its ability to hybridize under stringent conditions to another nucleic acid (such as the exemplary sequences described herein).

The phrase "stringent hybridization conditions" refers to conditions under which a probe will primarily hybridize to its target subsequence, typically in a complex mixture of nucleic acid, but to no other sequences. Stringent conditions are sequence-dependent and will be different in different circumstances, e.g., depending on the length of the probe. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5–10° C. lower than the thermal melting point (Tm) for the specific sequence at a defined ionic strength and pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to about 50 nucleotides) and at least about 60° C. for long probes (e.g., greater than about 50 nucleotides). Stringent conditions may also be achieved with the addition of destabilizing agents such as formamide. For selective or specific hybridization, a positive signal (e.g., identification of a nucleic acid of the invention) is about 5–10 times background hybridization. "Stringent" hybridization conditions that are used to identify substantially identical nucleic acids within the scope of the invention include hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C., for long probes. For short probes, stringent hybridization conditions include hybridization in a buffer comprising 50% formamide, 5×SSC and 1% SDS at room temperature or hybridization in a buffer comprising 5×SSC and 1% SDS at 370° C.–42° C., both with a wash of 0.2×SSC and 0.1% SDS at 37° C.–42° C. However, as is apparent to one of ordinary skill in the art, hybridization conditions can be modified depending on sequence composition. Exemplary "moderately stringent hybridization conditions" include a hybridization in a buffer of 40% formamide, 1 M NaCl, and 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

General Techniques

The TERT promoter sequences of the invention and nucleic acids used to practice this invention, whether RNA, cDNA, genomic DNA, or hybrids thereof, may be isolated from a variety of sources, genetically engineered, amplified, and/or expressed recombinantly. Any recombinant expression system can be used, including, e.g., bacterial, yeast, insect or mammalian systems. Alternatively, these nucleic acids can be chemically synthesized in vitro. Techniques for the manipulation of nucleic acids, such as, e.g., subcloning into expression vectors, labeling probes, sequencing, and hybridization are well described in the scientific and patent literature, see e.g., ed., MOLECULAR CLONING: A LABORATORY MANUAL (2ND ED.), Vols. 1–3, Cold Spring Harbor Laboratory, (1989) ("Sambrook"); CURRENT PROTOCOLS IN MOLECULAR BIOLOGY, Ausubel, ed. John Wiley & Sons, Inc., New York (1997) ("Ausubel"); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993) ("Tijssen"). Nucleic acids can be analyzed and quantified by any of a number of general means well known to those of skill in the art. These include, e.g., analytical biochemical methods such as NMR, spectrophotometry, radiography, electrophoresis, capillary electrophoresis, high pressure liquid chromatography (HPLC), thin layer chromatography (TLC), and hyperdiffusion chromatography, various immunological methods, such as fluid or gel precipitin reactions, immunodiffusion (single or double), immunoelectrophoresis, radioimmunoassays (RIAs), enzyme-linked immunosorbent assays (ELISAs), immunofluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

Amplification of hTERT Promoter Sequences

The invention provides oligonucleotide primers that can amplify all or any specific region within the TERT promoter sequence of the invention, including, e.g., specific promoter and enhancer subsequences. The nucleic acids of the invention can also be generated or measured quantitatively using amplification techniques. Using the TERT promoter sequences of the invention (e.g., as in the exemplary hTERT SEQ ID NO:1 or mTERT SEQ ID NO:2), the skilled artisan can select and design suitable oligonucleotide amplification primers. Amplification methods are also well known in the art, and include, e.g., polymerase chain reaction, PCR (PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (Wu (1989) Genomics 4:560; Landegren (1988) Science 241:1077; Barringer (1990) Gene 89:117); transcription amplification (Kwoh (1989) Proc. Natl. Acad. Sci. USA, 86:1173); and, self-sustained sequence replication (Guatelli (1990) Proc. Natl. Acad. Sci. USA, 87:1874); Q Beta replicase amplification (Smith (1997) J. Clin. Microbiol. 35:1477–1491, automated Q-beta replicase amplification assay; Burg (1996) Mol. Cell. Probes 10:257–271) and other RNA polymerase mediated techniques (e.g., NASBA, Cangene, Mississauga, Ontario); see also Berger (1987) Methods Enzymol. 152:307–316, Sambrook, Ausubel, Mullis (1987) U.S. Pat. Nos. 4,683,195, and 4,683,202; Arnheim (1990) C&EN 36–47; Lomell J. Clin. Chem., 35:1826 (1989); Van Brunt (1990) Biotechnology, 8:291–294; Wu (1989) Gene 4:560;

Sooknanan (1995) Biotechnology 13:563–564. Once amplified, TERT genomic DNA, TERT promoter sequences, and the like, can be cloned, if desired, into any of a variety of vectors using routine molecular biological methods; methods for cloning in vitro amplified nucleic acids are described, e.g., in Wallace, U.S. Pat. No. 5,426,039.

Modified hTERT Promoter Sequences

The invention also provides for TERT promoter sequences that have been modified in a site-specific manner to alter, add to, or delete some or all of the promoter's functions. For example, specific base pairs can be modified to alter, increase or decrease the binding affinity to trans-acting transcriptional regulatory factors, thus modifying the relative level of transcriptional activation or repression. Modifications can also change secondary structures of specific subsequences, such as those associated with many cis-acting transcriptional elements. Site-specific mutations can be introduced into nucleic acids by a variety of conventional techniques, well described in the scientific and patent literature. Illustrative examples include, e.g., site-directed mutagenesis by overlap extension polymerase chain reaction (OE-PCR), as in Urban (1997) Nucleic Acids Res. 25:2227–2228; Ke (1997) Nucleic Acids Res 25:3371–3372, and Chattopadhyay (1997) Biotechniques 22:1054–1056, describing PCR-based site-directed mutagenesis "megaprimer" method; Bohnsack (1997) Mol. Biotechnol. 7:181–188; Ailenberg (1997) Biotechniques 22:624–626, describing site-directed mutagenesis using a PCR-based staggered re-annealing method without restriction enzymes; Nicolas (1997) Biotechniques 22:430–434, site-directed mutagenesis using long primer-unique site elimination and exonuclease III. See also Sambrook and Ausubel. Modified TERT promoter sequences of the invention can be further produced by chemical modification methods, see, e.g., Belousov (1997) Nucleic Acids Res. 25:3440–3444; Frenkel (1995) Free Radic. Biol. Med. 19:373–380; Blommers (1994) Biochemistry 33:7886–7896. Designing Antisense Oligonucleotides The invention also provides antisense oligonucleotides capable of binding TERT promoter regions which, at least in part, modulate TERT transcription and telomerase activity. For example, antisense oligonucleotides that form triplexes with promoter regions inhibit the activity of that promoter, see, e.g., Joseph (1997) Nucleic Acids Res. 25:2182–2188; Alunni-Fabbroni (1996) Biochemistry 35:16361–16369; Olivas (1996) Nucleic Acids Res 24:1758–1764. Alternatively, antisense oligonucleotides that hybridize to the promoter sequence can be used to inhibit promoter activity. Means to design antisense oligonucleotides are well known in the art.

For example, antisense polynucleotides of the invention can comprise an antisense sequence of at least 7 to 10 to about 20 or more nucleotides that specifically hybridize to a sequence complementary to the TERT promoter sequences of the invention (e.g., including part of the exemplary hTERT SEQ ID NO:1 or mTERT SEQ ID NO:2, as discussed above). Alternatively, the antisense polynucleotide of the invention can be from about 10 to about 50 nucleotides in length or from about 14 to about 35 nucleotides in length. In other embodiments, they are less than about 100 nucleotides or less than about 200 nucleotides. In general, the antisense polynucleotide should be long enough to form a stable duplex (or triplex) but, if desired, short enough, depending on the mode of delivery, to be administered in vivo. The minimum length of a polynucleotide required for specific hybridization to a target sequence depends on several factors, such as G/C content, positioning of mismatched bases (if any), degree of uniqueness of the sequence as compared to the population of target polynucleotides, and chemical nature of the nucleotides used in the antisense reagent (e.g., methylphosphonate backbone, peptide nucleic acid, phosphorothioate), among other factors. Methods relating to antisense polynucleotides, are also described, e.g., by ANTISENSE RNA AND DNA, (1988), D. A. Melton, Ed., Cold Spring Harbor Laboratory, Cold Spring Harbor, N.Y.); Dagle (1991) Nucleic Acids Research 19:1805; Kim (1998) J. Controlled Release 53:175–182; for antisense therapy, see, e.g., Uhlmann (1990) Chem. Reviews 90:543–584; Poston (1998) J. Thorac. Cardiovasc. Surg. 116:386–396 (ex vivo gene therapy); Haller (1998) Kidney Int. 53:1550–1558; Nguyen (1998) Cancer Res 58:5673–7.

Identifying hTERT Genomic Sequences

The present invention provides TERT promoters comprising genomic sequences, including, e.g., 5' (upstream) of an hTERT or mTERT transcriptional start site, and intronic sequences, as described below. The promoter of the invention contains cis-acting transcriptional regulatory elements involved in TERT message expression. It will be apparent that, in addition to the nucleic acid sequences provided in hTERT SEQ ID NO:1 or mTERT SEQ ID NO:2, additional TERT promoter sequences may be readily obtained using routine molecular biological techniques. For example, additional hTERT genomic (and promoter) sequence may be obtained by screening a human genomic library using an hTERT nucleic acid probe having a sequence or subsequence as set forth in SEQ ID NO:1 (a nucleic acid sequence is within the scope of the invention if it hybridizes under stringent conditions, as defined above, to an hTERT promoter sequence of the invention). Additional hTERT or mTERT genomic sequence can be readily identified by "chromosome walking" techniques, as described by, e.g., Hauser (1998) Plant J 16:117–125; Min (1998) Biotechniques 24:398–400. Other useful methods for further characterization of TERT promoter sequences, e.g., sequences flanking SEQ ID NO:1 or mTERT SEQ ID NO:2, include those general methods described by, e.g., Pang (1997) Biotechniques 22:1046–1048; Gobinda (1993) PCR Meth. Applic. 2:318; Triglia (1988) Nucleic Acids Res. 16:8186; Lagerstrom (1991) PCR Methods Applic. 1:111; Parker (1991) Nucleic Acids Res. 19:3055. As is apparent to one of ordinary skill in the art, these techniques can also be applied to any TERT promoter sequences in addition to the human and mouse genomic sequences described herein.

Chemical Synthesis of TERT Promoter Sequences

The present invention also provides TERT polynucleotides that are produced by direct chemical synthesis. Chemical synthesis will typically be used to produce oligonucleotides and polynucleotides containing nonstandard nucleotides (e.g., probes, primers and antisense oligonucleotides) although nucleic acids containing only standard nucleotides can also be prepared. Direct chemical synthesis of nucleic acids can be accomplished by methods known in the art, such as, e.g., the phosphotriester method of Narang (1979) Meth. Enzymol. 68:90; the phosphodiester method of Brown (1979) Meth. Enzymol. 68:109; the diethyl-phosphoramidite method of Beaucage (1981) Tetra. Lett. 22:1859; and the solid support method of U.S. Pat. No. 4,458,066. Chemical synthesis typically produces a single stranded oligonucleotide, which may be converted into double stranded DNA by hybridization with a complementary sequence, or by polymerization with a DNA polymerase and an oligonucleotide primer using the single strand as a template. One of skill will recognize that while chemical synthesis of DNA is often limited to sequences of less than about 100 or 150 bases, longer sequences may be obtained by the ligation of shorter sequences or by more elaborate synthetic methods. It will be appreciated that the polynucleotides and oligonucleotides of the invention can be made using nonstandard bases (e.g., other than adenine, cytidine, guanine, thymine, and uridine) or nonstandard backbone structures to provide desirable properties (e.g., increased nuclease-resistance, tighter binding, stability or a desired TM). Techniques for rendering oligonucleotides nuclease-resistant include those described in PCT publication WO 94/12633. A wide variety of useful modified oligonucleotides may be produced, including oligonucleotides having a peptide nucleic acid (PNA) backbone (Nielsen (1991) Science 254:1497) or incorporating 2'-O-methyl ribonucleotides, phosphorothioate nucleotides, methyl phosphonate nucleotides, phosphotriester nucleotides, phosphorothioate nucleotides, and phosphoramidates. Still other useful oligonucleotides may contain alkyl and halogen-substituted sugar moieties comprising one of the following at the 2' position: OH, SH, SCH3, F, OCN, OCH3OCH3, OCH3O(CH2)nCH3, O(CH2)nNH2 or O(CH2)nCH3 where n is from 1 to about 10; C1 to C10 lower alkyl, substituted lower alkyl, alkaryl or aralkyl; Cl; Br; CN; CF3; OCF3; O-, S-, or N-alkyl; O-, S-, or N-alkenyl; SOCH3; SO2CH3; ONO2; NO2; N3; NH2; heterocycloalkyl; heterocycloalkaryl; amino-alkylamino; polyalkylamino; substituted silyl; an RNA cleaving group; a cholesteryl group; a folate group; a reporter group; an intercalator; a group for improving the pharmacokinetic properties of an oligonucleotide; or a group for improving the pharmacodynamic properties of an oligonucleotide and other substituents having similar properties. Folate, cholesterol or other groups which facilitate oligonucleotide uptake, such as lipid analogs, may be conjugated directly or via a linker at the 2' position of any nucleoside or at the 3' or 5' position of the 3'-terminal or 5'-terminal nucleoside, respectively. One or more such conjugates may be used. Oligonucleotides may also have sugar mimetics such as cyclobutyls in place of the pentofuranosyl group. Other embodiments may include at least one modified base form or "universal base" such as inosine, or inclusion of other nonstandard bases such as queosine and wybutosine as well as acetyl-, methyl-, thio- and similarly modified forms of adenine, cytidine, guanine, thymine, and uridine which are not as easily recognized by endogenous endonucleases. The invention further provides oligonucleotides having backbone analogues such as phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, chiral-methyl phosphonates, nucleotides with short chain alkyl or cycloalkyl intersugar linkages, short chain heteroatomic or heterocyclic intersugar ("backbone") linkages, or CH2—NH—O—CH2, CH2—N(CH3)—OCH2, CH2—O—N(CH3)—CH2, CH2—N(CH3)—N(CH3)—CH2 and O—N(CH3)—CH2—CH2 backbones (where phosphodiester is O—P—O—CH2), or mixtures of the same. Also useful are oligonucleotides having morpholino backbone structures (see. e.g., U.S. Pat. No. 5,034,506).

Figure 3:
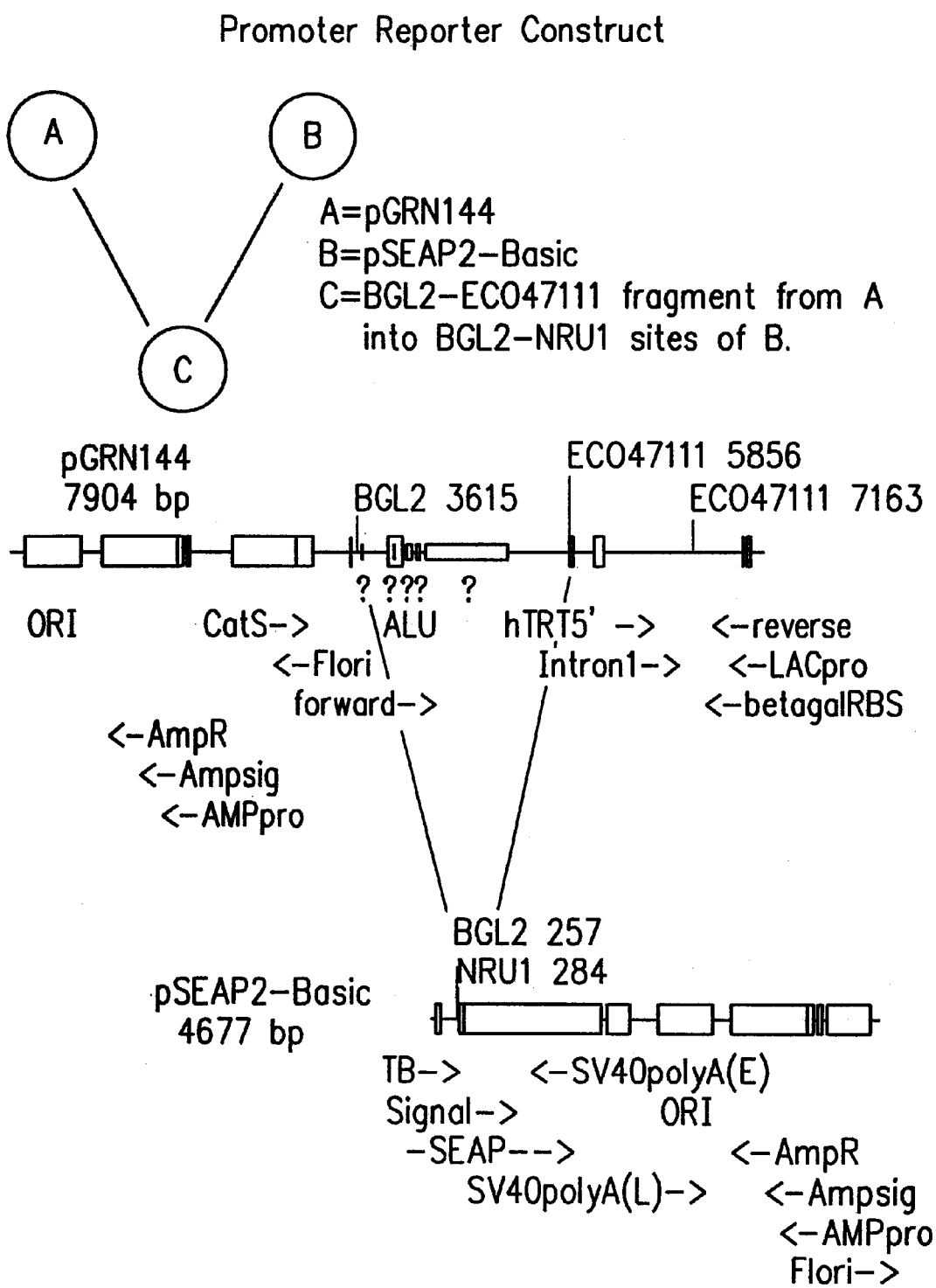
FIG. 3 shows the construction of an hTERT promoter-reporter plasmid, discussed in detail in Example 2, below.

Identifying TERT Promoter Subsequences Bound by Trans-Acting Transcriptional Regulatory Factors The invention provides means to identify and isolate trans-acting transcriptional regulatory factors that are involved in modulating the activity of the TERT promoter. Identification of cis-acting motifs by, e.g., sequence identity comparison, as discussed above, can be a useful initial means to identify promoter sequences bound by trans-acting factors. For example, as discussed above, the hTERT and mTERT promoters contain a variety of cis-acting motifs. The hTERT promoter contains the motif known to bind to c-Myc (the "E-box" or "Myc/Max binding site"). Two SP1 binding sites are located starting at residue −168 and starting at residue −134 (FIG. 3A). Other identified motifs include the sex determining region Y gene product (SRY), hepatic nuclear factors 3-beta (HNF-3_) and 5 (HNF-5), TFIID-MBP, E2F and c-Myb cis-acting transcriptional regulatory elements. All other cis-acting transcriptional regulatory elements known in the art (searchable by, e.g., public data base, e.g., http://www.ncbi.nlm.nih.gov/PubMedl) present in the TERT promoter sequences described herein are incorporated by the invention. To identify these motifs, a variety of comparison algorithms can be used. See, e.g., Karas (1996) Comput. Appl. Biosci. 12:441–6; Frech (1997) Pac Symp Biocomput. 7:151–62; Brzma (1998) Genome Res 8:1202–1215; Tsunoda (1998) Pac Symp Biocomput: 1998:252–63.

In addition to sequence identity analysis, TERT cis-acting transcriptional regulatory elements can be identified or confirmed by any means known in the art, including, e.g., promoter activity assays, DNase assays, binding assays (e.g., mobility shift assays), oligonucleotide affinity column chromatography, and the like.

After positive or tentative identification of a cis-acting binding site in a TERT promoter, these sequences are used to isolate the trans-acting transcriptional regulatory factor(s) by any means known in the art. In a preferred embodiment, the trans-acting factors are isolated using sequence-specific oligonucleotide affinity chromatography, the oligonucleotides comprising TERT sequences of the invention.

Another embodiemtn for identifying transcriptional regulatory motifs involves modifying putative cis-acting regulatory subsequences and assessing the change; if any, of the resultant TERT promoter to modulate transcription. The modification can be, e.g., one or more residue deletions, residue substitution(s), chemical alteration(s) of nucleotides, and the like. The (modified) promoter can be operably linked to TERT, or any transcribable sequence (e.g., "reporter genes"). The relative increase or decrease the modification has on transcriptional rates can be determined, e.g., by measuring the ability of the unaltered TERT promoter to transcriptionally activate the reporter coding sequence under the same conditions as used to test the modified promoter. An increase or decrease in the ability of the modified TERT promoter to induce transcription as compared to the unmodified promoter construct identifies a cis-acting transcriptional regulatory sequence that is involved in the modulation of TERT promoter activity.

The reporter gene can encode any detectable protein known in the art, e.g., detectable by fluorescence or phosphorescence or by virtue of its possessing an enzymatic activity. In alternative embodiments, the detectable protein is firefly luciferase, alpha-glucuronidase, alpha-galactosidase, chloramphenicol acetyl transferase, green fluorescent protein, enhanced green fluorescent protein, and the human secreted alkaline phosphatase.

Another embodiment tests the ability of these cis-acting elements to bind soluble polypeptide trans-acting factors isolated from different cellular compartments, particularly trans-acting factors expressed in nuclei. For identification and isolation of factors that stimulate transcription, cell (e.g. nuclear) extracts from cells that express TERT are used. Means to conduct these studies are well known in the art.

Furthermore, as discussed further below, once a cis-acting motif, or element, is identified, it can be used to identify and isolate trans-acting factors in a variety of cells and under different conditions (e.g., cell proliferation versus cell senescence). Accordingly, the invention provides a method for screening for trans-acting factors that modulate TERT promoter activity under a variety of conditions, developmental states, and cell types (including, e.g., normal versus immortal versus malignant phenotypes).

The cis-acting transcriptional regulatory sequences of the invention that modulate TERT promoter activity can also be used as oligonucleotides which, upon introduction into a cell, can bind trans-acting regulatory factors to modulate TERT transcription in vivo. This results in increased or decreased cell proliferative capacity for the treatment of various diseases and conditions, as discussed below.

High Throughput Screening of Small Molecule Modulators of TERT Transcription

The invention provides constructs and methods for screening modulators, in a preferred embodiment, small molecule modulators, of TERT promoter activity in vitro and in vivo. The invention incorporates all assays available to screen for small molecule modulators of TERT transcription. In a preferred embodiment, high throughput assays are adapted and used with the novel TERT promoter sequences and constructs provided by the invention, e.g., the hTERT and mTERT promoter sequences described herein. See, e.g., Schultz (1998) Bioorg Med Chem Lett 8:2409–2414; Weller (1997) Mol Divers. 3:61–70; Fernandes (1998) Curr Opin Chem Biol 2:597–603; Sittampalam (1997) Curr Opin Chem Biol 1:384–91.

In alternative embodiments, recombinant constructs contain hTERT promoter sequences driving a marker, such as an alkaline phosphatase marker gene (SEAP) or a §-galactosidase gene. Using a SEAP expressing construct of the invention, it was demonstrated that a TERT promoter fragment of approximately 2.5 kb is sufficient to activate and repress TERT transcription in response to proliferation and/or growth arrest stimuli in a model cell line, IDH4. Two cell clones, ID245-1 and ID245-16 whose SEAP profiles closely matched telomerase activity after TERT upregulation by dexamethasone were selected and expanded for high throughput screening of small molecule activators of telomerase.

Treatment of Telomerase-Related Diseases

The present invention provides TERT promoter sequences useful for the treatment of diseases and disease conditions. The recombinant and synthetic nucleic acids comprising TERT promoter, or TERT antisense complementary sequences, can be used to create or elevate telomerase activity in a cell, as well as to inhibit telomerase activity in cells in which it is not desired. In a preferred embodiment, human TERT promoter sequences or antisense sequences are used for the treatment of human diseases and disease conditions.

Identification of cis-acting transcriptional regulatory sequences by the invention further provides for the design of targeted sequences that, as oligonucleotides, can modify TERT promoter activity. In one embodiment, telomerase activity is created or elevated by binding significant amounts of a trans-acting transcriptional repressor or down-regulator with a nucleic acid that binds specifically to the repressor. In another embodiment, telomerase activity is down-regulated by antisense oligonucleotides binding to promoter sequences (see discussion, above). Similarly, telomerase activity can be inhibited by binding significant amounts of a trans-acting transcriptional activator or up-regulator with a nucleic acid that binds specifically to the activator; or telomerase activity is up-regulated by antisense oligonucleotides binding to promoter sequences involved in telomerase repression. Thus, inhibiting, activating or otherwise altering a telomerase activity (e.g., telomerase catalytic activity, fidelity, processivity, telomere binding, etc.) in a cell can be used to change the proliferative capacity of the cell.

For example, reduction of telomerase activity in an immortal cell, such as a malignant tumor cell, can render the cell mortal. Conversely, increasing the telomerase activity in a cell line or a mortal cell (e.g., most human somatic cells) can increase the proliferative capacity of the cell. For example, expression of hTERT protein in dermal fibroblasts, thereby increasing telomere length, will result in increased fibroblast proliferative capacity. Such expression can slow or reverse age-related degenerative processes, such as, e.g., the age-dependent slowing of wound closure (see, e.g., West (1994) Arch. Derm. 130:87). Thus, in one aspect, the present invention provides reagents and methods useful for treating diseases and conditions characterized by the presence, absence, or altered amount of human telomerase activity in a cell (where the diseases and conditions are susceptible to treatment using the compositions and methods disclosed herein). These diseases include, e.g. cancers, other diseases of cell proliferation (particularly, degenerative and aging processes and diseases of aging), immunological disorders, infertility (or fertility).

Treatment of Cancer

The present invention provides methods and compositions for reducing TERT promoter activity (and hence telomerase activity) in immortal cells and tumor cells for treating cancer. Cancer cells (e.g., malignant tumor cells) that express telomerase activity (telomerase-positive cells) can be mortalized by decreasing or inhibiting TERT promoter activity. Moreover, because measurable telomerase activity levels correlate with disease characteristics such as metastatic potential (see, e.g., U.S. Pat. Nos. 5,639,613; 5,648, 215; 5,489,508; and Pandita (1996) Proc. Am. Ass. Cancer Res. 37:559), any reduction in TERT promoter activity could reduce the aggressive nature of a cancer to a more manageable disease state. As noted above, immortal cells and cancer cells, as opposed to non-cancerous, mortal cells, have high levels of TERT promoter activity.

Taking advantage of this characteristic, in one embodiment of the invention, a TERT promoter sequence is operably linked to a gene encoding a toxin and introduced into a cell to kill the cell (a number of protein toxins are well known in the art including, e.g., ricin, diphtheria, gelonin, Pseudomonas toxin, abrin). If or when TERT transcriptional activators are expressed or activated in the cell, the toxin will be expressed, resulting in specific cell killing.

Alternatively, the TERT promoter-linked gene can encode a protein having activity that is not itself toxic to a cell, but which renders the cell sensitive to an otherwise nontoxic drug (such as, e.g., Herpes virus thymidine kinase).

In another embodiment, the invention takes advantage of the fact that normal cytopathic viruses, in particular human cytopathic viruses, such as adenovirus or Herpes virus, require essential virally encoded genes to proliferate thereby lysing specific cells. If any one of these essential viral genes was modified such that expression of the essential element was driven by the TERT promoter, proliferation of the virus and its cytopathic effects would be restricted to tumor cells and other telomerase expressing cells. Accordingly, the invention provides constructs and methods for killing telomerase positive cells (e.g., cancer cells, germ cells) wherein TERT promoter sequences of the invention are operably linked to such viral "essential element" genes. For use in human cells, human cytopathic viruses modified with hTERT promoter sequences are preferred. Any one or more of the genes required for the replication and packaging of the virus could be modified to be driven by the TERT promoter. For instance, in one embodiment, expression of the E1a gene of adenovirus, which is required for the activation of expression of a cascade of adenoviral genes, is placed under the control of the hTERT promoter.

Thus, expression of E1a, and hence downstream replication of the virus, occurs only in those cells that express telomerase (i.e., tumor cells). Likewise, a recombinant adenovirus of the invention is designed so the adenoviral capsid genes are under the control of a TERT promoter. While this construct replicates its DNA in most cell types, it packages itself into active, infectious (and cytotoxic) virus only in those cells that express telomerase. Thus, when these constructs are used as cancer therapeutics, the conditionally replicative virus only infects and yields a productive infection in tumor cells (with no effect in "normal" cells that do not express telomerase). Infection of normal cells that do not express telomerase is expected to produce either no or abortive production of the virus, depending on which gene is driven by the TERT promoter. Thus, these recombinant viruses of the invention allow the natural, yet tumor specific, amplification of an oncolytic virus.

In alternative embodiments, many other elements are incorporated into such an TERT promoter restricted oncolytic virus or a TERT promoter restricted replicative but not lytic. Genes encoding suicide genes, marker genes, apoptotic genes or cell cycle regulators are incorporated in the TERT promoter restricted conditionally replicative recombinant virus. Expression of these elements in such a virus would assist the arrest of tumor growth. In one embodiment, elements to be included within these conditionally replicative viruses of the invention are structures that inhibit telomerase activity. These telomerase inhibitors could incorporate inhibitory oligonucleotides, dominant-negative inhibitors of TERT, or the gene for any agent that would disrupt or prevent TR/TERT assembly, interactions, or activity.

Other elements can also be included in the "TERT promoter restricted" vectors of the invention (i.e., vectors expressing TERT promoter driven genes which are only expressed in telomerase-positive cells). For example, small inhibitory RNA molecules, preferably targetting cancer cells, such as RNA targeting telomerase activity can be synthesized in vivo using a recombinant adenovirus vector. Exemplary sequences are provided in U.S. Pat. No. 5,858,777 and GB 20890.4. RNA production from the adenovirus can be achieved by a variety of expression cassettes. For cell growth inhibition purposes, RNA polymerase III expression cassettes based on the structure of tRNA genes and other RNA polymerase III transcripts, including the U6 snRNA gene, as well as RNA polymerase II snRNP (U1, U2) transcripts are preferred due to their ability to produce high levels of transcripts.

The hTERT promoter restricted viruses of the invention can be designed to express inhibitory RNAs, as antisense molecules complementary to several regions of the hTR molecule, including the template region. The inhibitory RNAs can also mimic sequences and/or structures present in the RNA component of telomerase (e.g., hTR), including potential binding site(s) for TERT or other telomerase-associated proteins that might interact with the RNA component. Other elements can also be designed to generate inhibitory RNAs to target TERT mRNA by preventing its normal processing, folding, modification, transport and/or translation.

Other cytopathic viral vectors of the invention can be designed to generate RNA molecules with sequences necessary for cytoplasmic export and translation into peptides. The resulting polypeptides or peptides can be designed to target telomerase components or other molecules that are associated with telomerase thereby influencing telomerase catalytic activity. The peptides that inhibit telomerase will be produced at high level, paralleling the amount of RNA. For example, peptides could be designed to mimic the stretch of amino acids in hTERT involved in its binding to hTR, thereby acting as competitors in the assembly of a functional telomerase.

The TERT promoter restricted viral vectors of the invention can also be designed to generate peptides or polypeptides for any domain of TERT involved in interactions with other proteins and disrupt contacts that are essential for telomerase function. Other TERT promoter restricted viruses of the invention can be designed to generate polypeptides to bind to telomere complexes and prevent access and/or docking of telomerase or to generate immunogenic peptides, in part TERT peptides.

Other TERT promoter restricted viral vectors of the invention can be designed to generate polypeptides to mimic a variety of apoptosis inducing agents observed during programmed cell death and could result in the onset of apoptosis.

TERT promoter restricted viruses do not necessarily need to be cytopathic. The TERT promoter conditionally restricted virus could be used to amplify any sequences or any element in any TERT expressing cell, e.g., a tumor cell.

Any of these embodiments can be provided with the conditionally replicative viruses of the invention. The TERT promoter constructs of the invention can also be used in gene therapy vectors to prevent telomerase activation and result in specific "mortalization" or death of telomerase-positive cells. Similarly, these gene therapy methods may be used for "treating" a genetic predilection for cancers.

Treatment of Other Conditions

The present invention also provides compositions and methods useful for treatment of diseases and disease conditions (in addition to cancers) characterized by under- or over-expression of telomerase or TERT gene products. Examples include, e.g., diseases of cell proliferation, diseases resulting from cell senescence (particularly processes and diseases of aging), immunological disorders, infertility, and diseases of immune dysfunction. Certain diseases of aging are characterized by cell senescence-associated changes due to reduced telomere length (compared to younger cells), resulting from the absence (or much lower levels) of telomerase activity in the cell. Decreased telomere length and decreased replicative capacity contribute to these diseases. Telomerase activity (resulting in increased telomere length) can be upregulated by, e.g., increasing TERT promoter activity in the cell.

The present invention, by providing methods and compositions for modulating TERT promoter activity, also provides methods to treat infertility. Human germline cells (e.g., spermatogonia cells, their progenitors or descendants) are capable of indefinite proliferation and characterized by high telomerase activity. Abnormal or diminished levels of TERT gene products can result, e.g., in inadequate or abnormal production of spermatozoa, leading to infertility or disorders of reproduction. Accordingly, "telomerase-based" infertility can be treated using the methods and compositions described herein to increase TERT promoter activity levels. Similarly, because inhibition of telomerase may negatively impact spermatogenesis, oogenesis, and sperm and egg viability, the compositions of the invention capable of inhibiting hTERT promoter activity can have contraceptive effects when used to reduce hTERT levels in germline cells.

In a further embodiment, the invention provides methods and composition useful for decreasing the proliferative potential of telomerase-positive cells such as activated lymphocytes and hematopoietic stem cells by reducing TERT promoter activity. Thus, the invention provides means for effecting immunosuppression. Conversely, the methods and reagents of the invention are useful in immunostimulation by increasing TERT promoter activity (resulting in increased proliferative potential) in immune cells, including hematopoietic stem cells (that express a low level of telomerase or no telomerase prior to therapeutic intervention).

Modulating TERT Promoter Activity

As is clear from the foregoing discussion, modulation of the level of TERT promoter transcriptional activity (and thus, the levels of telomerase or telomerase activity of a cell) can have a profound effect on the proliferative potential of the cell, and so has great utility in treatment of disease. This modulation can either be a decrease or an increase in TERT promoter activity. The promoter activity-modulatory nucleic acid molecules of the invention can act through a number of mechanisms. However, the invention is not limited to any particular mechanism of action.

For example, TERT promoter activity may be decreased or increased by single stranded antisense sequences that directly bind to TERT promoter sequences. This will result in decrease in affinity or inhibition of trans-acting transcriptional regulatory factors binding to critical TERT promoter sequences (e.g., TATA boxes, CAAT boxes, and the like). When the cis-acting element bound by a trans-acting factor has inhibitory activity, the binding of the oligonucleotide would result in upregulation of TERT transcription. Conversely, if the promoter subsequence, when bound by a trans-acting factor, has upregulating activity, the binding of the oligonucleotide would result in down-regulation of TERT transcription. In another embodiment, double-stranded oligonucleotides representing TERT promoter subsequences directly bind trans-acting transcriptional modulatory elements, thus preventing them from binding their corresponding cis-acting elements. In summary, TERT promoter activity may be increased or decreased through any of several mechanisms, or a combination of mechanisms. These include any means apparent to those of skill upon review of this disclosure.

Antisense Oligonucleotides Binding to TERT Promoter Control Sequences

As discussed above, antisense oligonucleotides which hybridize to TERT promoter sequences will inhibit the binding of trans-acting transcriptional upregulatory agents to critical TERT promoter sequences. Furthermore, the result will be activation or repression of TERT transcriptional activity, depending on whether the promoter subsequence is down-regulatory or up-regulatory, respectively. Thus, the invention provides antisense oligonucleotides directed to the TERT promoter (cis-acting) binding sites for c-Myc (the "E-box" or "Myc/Max binding sites"), SP1, Y gene product (SRY), hepatic nuclear factors 3-beta (HNF-3_), 5 (HNF-5), TFIID-MBP, E2F, c-Myb, TATA boxes, CAAT boxes, and other, as described herein.

While the invention is not limited by any particular mechanism, oligonucleotides of the invention can also bind to double-stranded or duplex TERT promoter sequences. They can bind in a folded region, forming a triple helix, or "triplex" nucleic acid. Triple helix formation results in inhibition of TERT promoter activity by, e.g., disrupting the secondary structure of the promoter sequence, resulting in a new conformation which the trans-acting factor cannot bind with sufficient affinity to have a transcriptional-modifying effect. Alternatively, triple helix formation (induced by the binding of the antisense oligonucleotide of the invention) compromises the ability of the double helix to open sufficiently for the binding of polymerases, transcription factors, or regulatory trans-acting molecules to occur. Triplex oligo- and polynucleotides design construction (also discussed, above) is well described in the art; see, e.g., Cheng (1988) J. Biol. Chem. 263:15110; Ferrin (1991) Science 354:1494; Ramdas (1989) J. Biol. Chem. 264:17395; Strobel (1991) Science 254:1639; Rigas (1986) Proc. Natl. Acad. Sci. U.S.A. 83: 9591) Carr, 1994, MOLECULAR AND IMMUNOLOGIC APPROACHES, Futura Publishing Co, Mt Kisco N.Y.; Rininsland (1997) Proc. Natl. Acad. Sci. USA 94:5854; Perkins (1998) Biochemistry 37:11315–11322.

Double-Stranded Oligonucleotides Bind to Trans-Acting Molecules

The cis-acting transcriptional regulatory sequences of the invention can also be used as oligonucleotides which, upon introduction into a cell, can bind trans-acting regulatory factors to modulate TERT transcription in vivo. These oligonucleotides can be delivered to target cells through an appropriate delivery scheme or they can be synthesized in vivo by recombinant expression systems (vectors, viruses, and the like). Appropriate expression systems, delivery mechanisms, formulations, and the like are well known in the art (discussed in more detail, below).

Administration of Oligonucleotides IN VIVO

The therapeutic nucleic acids and methods of the invention involve the administration of oligonucleotides or polynucleotides that function to inhibit or stimulate TERT promoter activity under in vivo physiological conditions. In one embodiment, these nucleic acids are, e.g., single stranded antisense sequences capable of binding to promoter sequences. In an alternative embodiment, they are double stranded nucleic acids capable of binding trans-acting transcriptional regulatory factors. They should be sufficiently stable under physiological conditions for a period of time to obtain a therapeutic effect. As noted above, modified nucleic acids may be useful in imparting such stability, as well as for targeting delivery of the oligonucleotide to the desired tissue, organ, or cell. Oligo- and poly-nucleotides can be delivered directly as a drug in a suitable pharmaceutical formulation, or indirectly by means of introducing a nucleic acid expression system (e.g., cassette, vector) which can recombinantly generate the hTERT promoter modulating oligonucleotides into a cell, e.g., by "gene therapy" (see below).

Oligonucleotides or expression vectors can be administered by any means known in the art, including, e.g., liposomes, immunoliposomes, ballistics, direct uptake into cells, and the like. For treatment of disease (see discussion above), the oligonucleotides of the invention will be administered to a patient in a therapeutically effective amount. A therapeutically effective amount is an amount sufficient to ameliorate the symptoms of the disease or modulate hTERT promoter activity (thereby affecting telomerase activity) in the target cell. Methods useful for delivery of oligonucleotides for therapeutic purposes are well known in the art and are described, e.g., in U.S. Pat. No. 5,272,065.

Telomerase activity can be measured by a variety of means, e.g., by TRAP assay or other suitable assay of telomerase biological function, as discussed in detail in related applications.

Gene Therapy

The invention provides methods and reagents for affecting TERT promoter activity in vivo by gene therapy. In one embodiment, as discussed above, gene therapy is used to deliver oligonucleotides that modulate TERT promoter activity by directly binding to cis-acting sequences or, alternatively, that bind to trans-acting regulatory factors. One embodiment exploits the fact that the TERT promoter is only relatively active in a very limited range of cell types, including, significantly, cancer cells.

TERT Promoter Operably Linked to Cellular Toxins

In one embodiment, the TERT promoter of the invention is operably linked to a transcribable sequence which encodes a cellular toxin. A number of polypeptide toxins that can be recombinantly generated are well known in the art including, e.g., ricin, abrin (Hughes (1996) Hum. Exp. Toxicol. 15:443–451), diphtheria, gelonin (Rosenblum (1996) Cancer Immunol. Immunother. 42:115–121), Pseudomonas exotoxin A, tumor necrosis factor alpha (TNF-alpha), Crotalus durissus terrificus toxin, Crotalus adamenteus toxin, Naja naja toxin, and Naja mocambique toxin, see, e.g., Rodriguez (1998) Prostate 34:259–269; Mauceri (1996) Cancer Res. 56:4311–4314.

The cellular toxin can also be capable of inducing apoptosis, such as, e.g., a direct inducer of apoptosis, such as the ICE-family of cysteine proteases, the Bcl-2 family of proteins, bax, bclXs and caspases, see, e.g., Favrot (1998) Gene Ther. 5:728–739; McGill (1997) Front. Biosci. 2:D353–D379; McDonnell (1995) Semin. Cancer Biol. 6:53–60.

Alternatively, the sequence under the control of the TERT promoter can code for polypeptides having activity that is not itself toxic to a cell, but which renders the cell sensitive to an otherwise nontoxic drug, e.g., Herpes virus thymidine kinase (GSV-TK). The HSV-TK is innocuous but converts the anti-herpetic agent ganciclovir (GCV) to a toxic product that interferes with DNA replication in proliferating cells (see, e.g., Delaney (1996) J. Neurosci. 16:6908–6918; Heyman (1989) Proc. Natl. Acad. Sci. USA 86:2698–2702). The art describes numerous other suitable toxic or potentially toxic proteins and systems that may be applied in this embodiment.

The methods of the invention, in addition to enabling the specific killing of telomerase-positive cells, can also be used to prevent transformation of telomerase negative cells to a telomerase positive state. As shown in Example 1, an hTERT promoter sequence can be operably linked to a reporter gene such that activation of the promoter results in expression of the protein encoded by the reporter gene. If, instead of a reporter protein, the encoded protein is toxic to the cell, activation of the promoter leads to cell morbidity or death.

Modifying TERT Promoters by In vivo Homologous Recombination: Generating TERT "Knockout" Cells In another embodiment, the introduced TERT promoter sequence (modified or wild type) can replace or disrupt an endogenous TERT promoter sequence (e.g., gene replacement and "gene knockout," respectively). A newly introduced TERT promoter sequence can be engineered to have greater or lesser transcriptional activity, be responsive to new trans-acting transcriptional modulating agents, and the like.

Disruption of an endogenous TERT promoter sequence typically will decrease or abrogate ("knockout") the transcription of TERT. Therapeutic indications for such TERT promoter activity manipulations are discussed above. In one embodiment, the TERT promoter "knockout" is prepared by deletion or disruption by homologous recombination of the endogenous hTERT promoter. Homologous recombination and other means to alter (and "knockout") expression of endogenous sequences is well known in the art and is described in, e.g., Moynahan (1996) Hum. Mol. Genet. 5:875; Moynahan (1996) Hum. Mol. Genet. 5:875; Baudin (1993) Nucl. Acids Res. 21:3329; Wach (1994) Yeast 10:1793; Rothstein (1991) Methods Enzymol. 194:281; Anderson (1995) Methods Cell Biol. 48:31; Pettitt (1996) Development 122:4149–4157; Ramirez-Solis (1993) Methods Enzymol. 225:855; Thomas (1987) Cell 51:503; Couldrey (1998) Dev. Dyn. 212:284–292). Holzschu (1997) Transgenic Res 6:97–106; U.S. Pat. Nos. 5,464,764; 5,631,153; 5,487,992; 5,627,059, and 5,272,071; WO 91/09955; WO 93/09222; WO 96/29411; WO 95/31560; WO 91/12650.

Vectors useful in TERT gene therapy can be, e.g., viral or nonviral. They may comprise other regulatory or processing sequences. Gene therapy vectors are well known in the art, see, e.g., Lyddiatt (1998) Curr Opin Biotechnol 9:177–85.

As the invention is also directed to methods and reagents for gene replacement therapy (e.g., replacement by homologous recombination of an endogenous TERT gene with a recombinant gene), vectors specifically designed for integration by homologous recombination comprising TERT promoter sequences are also provided by the invention. Important factors for optimizing homologous recombination include the degree of sequence identity and length of homology to chromosomal sequences. The specific sequence mediating homologous recombination is also important, because integration occurs much more easily in transcriptionally active DNA. Methods and materials for constructing homologous targeting constructs are described by e.g., Mansour (1988) Nature 336: 348; Bradley (1992) Bio/Technology 10:534; U.S. Pat. Nos. 5,627,059; 5,487,992; 5,631,153; and 5,464,764.

The invention provides delivery of the expression systems (e.g., gene therapy vectors) of the invention into cells or tissues in vitro or ex vivo. For ex vivo therapy, vectors may be introduced into cells, e.g., stem cells, taken from the patient and clonally propagated for autologous transplant back into the same patient; see, e.g., U.S. Pat. Nos. 5,399,493 and 5,437,994. Cells that can be targeted for TERT promoter gene therapy aimed at increasing the telomerase activity of a target cell include, but are not limited to, embryonic stem or germ cells, particularly primate or human cells, hematopoietic stem cells (AIDS and post-chemotherapy), vascular endothelial cells (cardiac and cerebral vascular disease), skin fibroblasts and basal skin keratinocytes (wound healing and burns), chondrocytes (arthritis), brain astrocytes and microglial cells (Alzheimer's Disease), osteoblasts (osteoporosis), retinal cells (eye diseases), and pancreatic islet cells (Type I diabetes).

In one embodiment, the targeted cells are embryonic stem cells used to generate the non-human transgenic animals (e.g., mice) of the invention, as described herein.

Pharmaceutical Compositions

The invention provides pharmaceutical compositions that comprise TERT promoter-containing nucleic acids (e.g., oligo- and poly-nucleotides, expression vectors, gene therapy constructs, etc.) alone or in combination with at least one other agent, such as, e.g., a stabilizing compound, diluent, carrier, cell targeting agent, or another active ingredient or agent. The therapeutic agents of the invention may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with suitable excipient(s), adjuvants, and/or pharmaceutically acceptable carriers.

The pharmaceutical compositions of the invention can be administered by any means, such as, e.g., oral, parenteral, and the like. Methods of parenteral delivery include e.g., topical, intra-arterial (e.g., directly to the tumor), intramuscular (IM), subcutaneous (SC), intramedullary, intrathecal, intraventricular, intravenous (IV), intraperitoneal (IP), or intranasal administration. Further details on techniques for formulation and administration may be found in the latest edition of "REMINGTON'S PHARMACEUTICAL SCIENCES" (Maack Publishing Co, Easton Pa.). See also, e.g., PCT publication WO 93/23572.

Pharmaceutical compositions of the invention include TERT-containing nucleic acids in an effective amount to achieve the intended purpose. "Therapeutically effective amount" or "pharmacologically effective amount" are well recognized phrases and refer to that amount of an agent effective to produce the intended pharmacological result. For example, a therapeutically effective amount is an amount sufficient to treat a disease or condition or ameliorate the symptoms of the disease being treated. Useful assays to ascertain an effective amount for a given application (e.g., a therapeutically effective amount) includes, e.g., to measure the effect on endogenous TERT promoter activity and telomerase activity in a target cell (in the case of, e.g., inhibition therapy). The amount actually administered will be dependent upon the individual to which treatment is to be applied, and will preferably be an optimized amount such that the desired effect is achieved without significant side effects. The therapeutically effective dose can be estimated initially either in cell culture assays or in any appropriate animal model. The animal model is also used to estimate appropriate dosage ranges and routes of administration in humans. Thus, the determination of a therapeutically effective dose is well within the capability of those skilled in the art.

Production of Immortalized Cells, Cell Lines, and Animals

As described above, as an extension of the various embodiments providing TERT promoter-containing compositions and methods to increase TERT promoter activity, and to thereby increase telomerase expression, thus increasing the proliferative capacity of the cell, the invention also provides immortalized cells, cell lines and animals using the TERT promoter sequences of the invention. As discussed above, most vertebrate cells senesce after a finite number of divisions in culture (e.g., 50 to 100 divisions). Certain variant cells, however, are able to divide indefinitely in culture (e.g., HeLa cells, 293 cells) and, for this reason, are useful for research and industrial applications. Usually these immortal cell lines are derived from spontaneously arising tumors, or by transformation by exposure to, e.g., an oncogene, radiation or a tumor-inducing virus or chemical. Unfortunately, a limited selection of cell lines, especially human cell lines representing differentiated cell function, is available. Moreover, many immortal cell lines presently available are characterized by chromosomal abnormalities (e.g., aneuploidy, gene rearrangements, or mutations). Further, many long-established cell lines are relatively undifferentiated (e.g., they do not produce highly specialized products of the sort that uniquely characterize particular tissues or organs). Thus, there is a need for the TERT promoter activating compositions and methods of the invention to generate new immortal cell lines, especially using cells of human origin, where hTERT promoter activating compositions and methods are preferred.

The "immortalized cells" of the invention are not limited to those that proliferate indefinitely, but also include cells with increased proliferative capacity compared to similar cells whose TERT promoter has not been upregulated. Depending on the cell type, increased proliferative capacity may mean proliferation for at least about 50, about 100, about 150, about 200, or about 400 or more generations, or for at least about 3, about 6, about 12, about 18, about 24 or about 36 or more months in in vitro culture.

Uses for cells with increased proliferative capacity include, e.g., the production of natural proteins and recombinant proteins (e.g., therapeutic polypeptides such as erythropoietin, human growth hormone, insulin, and the like), or antibodies, for which a stable, genetically normal cell line is preferred. Another use is for replacement of diseased or damaged cells or tissue. For example, autologous immune cells immortalized using an TERT promoter sequence of the invention can be used for cell replacement in a patient after aggressive cancer therapy, e.g., whole body irradiation. Another use for immortalized cells is for ex vivo production of "artificial" tissues or organs (e.g., skin) for therapeutic use. Another use for such cells is for screening or validation of drugs, such as telomerase-inhibiting drugs, or for use in production of vaccines or biological reagents. Additional uses of the cells of the invention will be apparent to those of skill.

Karyotype Analysis: Deletions, Amplifications, and Translocations

The present invention further provides methods and reagents for karyotype analysis, gene amplification detection, or other chromosomal analysis using probes comprising the TERT promoter sequences of the invention. In various embodiments, amplifications (e.g., change in copy number), deletions, insertions, substitutions, or changes in the chromosomal location (e.g., translocations) of TERT promoter containing genes are detected. These can be correlated with the presence of a pathological condition or a predisposition to developing a pathological condition (e.g., cancer). Thus, this information can be used in a diagnostic or prognostic manner.

For instance, a translocation event could indicate that activation of TERT expression occurs in some cases by replacing all or part of the TERT promoter with another promoter element (e.g., a non-TERT promoter or enhancer) which directs TERT transcription in an inappropriate manner. Furthermore, the methods and reagents of the invention can be used to inhibit this inappropriate TERT activation.

Determining the chromosomal location of TERT promoter sequence may also be useful for analysis of TERT gene repression in normal somatic cells, for instance, whether the location is part of non-expressing heterochromatin. Nuclease hypersensitivity assays for distinguishing heterochromatin and euchromatin are described, e.g., in Wu (1979) Cell 16:797; Groudine (1982) Cell 30:131; Gross (1988) Ann. Rev. Biochem. 57:159. Methods for analyzing karyotype are well known in the art, and are discussed in detail in related applications See also, e.g., Pinkel (1988) Proc. Natl. Acad. Sci. USA 85:9138; EPO Pub. No. 430,402; Choo, ed., METHODS IN MOLECULAR BIOLOGY VOL. 33: IN SITU HYBRIDIZATION PROTOCOLS, Humana Press, Totowa, N.J., 1994; Kallioniemi (1992) Science 258:818).

Screening and Isolating TERT Promoter Binding Proteins and Other TRANS-Acting Transcriptional Agents In addition to the novel TERT promoter sequences and identification of the cis-acting transcriptional regulatory sequences contained therein, the invention provides for novel in vitro and cell-based in vivo assay systems to screen for TERT promoter binding proteins (trans-acting transcriptional regulatory factors) using the nucleic acids of the invention. Many assays are available that screen for nucleic acid binding proteins and all can be adapted and used with the novel TERT sequences provided by the invention. A few illustrative example are set forth below.

One embodiment of the invention provides a method of screening and isolating a TERT promoter binding compound by contacting a TERT promoter sequence of the invention (particularly, an identified cis-acting regulatory sequence) with a test compound and measuring the ability of the test compound to bind the selected nucleic acid. The test compound, as discussed above, can be any agent capable of specifically binding to a TERT promoter activity, including compounds available in chemical (e.g., combinatorial) libraries, a cell extract, a nuclear extract, a protein or peptide. If a TERT transcriptional activating protein is the goal of the search, a cell with telomerase activity is typically chosen.

A variety of well-known techniques can be used to identify polypeptides which specifically bind to TERT promoter, e.g., mobility shift DNA-binding assays, methylation and uracil interference assays, DNase and hydroxy radical footprinting analysis, fluorescence polarization, and UV crosslinking or chemical cross-linkers. For a general overview, see, e.g., Ausubel (chapter 12, DNA-Protein Interactions). One technique for isolating co-associating proteins, including nucleic acid and DNA/RNA binding proteins, includes use of UV crosslinking or chemical cross-linkers, including e.g., cleavable cross-linkers dithiobis (succinimidylpropionate) and 3,3'-dithiobis (sulfosuccinimidyl-propionate); see, e.g., McLaughlin (1996) Am. J. Hum. Genet. 59:561–569; Tang (1996) Biochemistry 35:8216–8225; Lingner (1996) Proc. Natl. Acad. Sci. USA 93:10712; Chodosh (1986) Mol. Cell. Biol 6:4723–4733. In many cases, there is a high likelihood that a specific protein (or a related protein) may bind to an hTERT promoter sequence, e.g., a Myc, NF-kappa B, EF2, Sp1, AP-1 or CAAT box binding site. In these scenarios, where an antibody may already be available or one can be easily generated, co-immunoprecipitation analysis can be used to identify and isolate TERT promoter-binding, trans-acting factors. The trans-acting factor can be characterized by peptide sequence analysis. Once identified, the function of the protein can be confirmed by methods known in the art, for example, by competition experiments, factor depletion experiments using an antibody specific for the factor, or by competition with a mutant factor.

Alternatively, TERT promoter-affinity columns can be generated to screen for potential TERT binding proteins. In a variation of this assay, TERT promoter subsequences are biotinylated, reacted with a solution suspected of containing a binding protein, and then reacted with a strepavidin affinity column to isolate the nucleic acid or binding protein complex (see, e.g., Grabowski (1986) Science 233:1294–1299; Chodosh (1986) supra). The promoter-binding protein can then be conventionally eluted and isolated. Mobility shift DNA-protein binding assay using nondenaturing polyacrylamide gel electrophoresis (PAGE) is an extremely rapid and sensitive method for detecting specific polypeptide binding to DNA (see, e.g., Chodosh (1986) supra, Carthew (1985) Cell 43:439–448; Trejo (1997) J. Biol. Chem. 272:27411–27421; Bayliss (1997) Nucleic Acids Res. 25:3984–3990).

Interference assays and DNase and hydroxy radical footprinting can be used to identify specific residues in the nucleic acid protein-binding site, see, e.g., Bi (1997) J. Biol. Chem. 272:26562–26572; Karaoglu (1991) Nucleic Acids Res. 19:5293–5300. Fluorescence polarization is a powerful technique for characterizing macromolecular associations and can provide equilibrium determinations of protein-DNA and protein-protein interactions. This technique is particularly useful (and better suited than electrophoretic methods) to study low affinity protein-protein interactions, see, e.g., Lundblad (1996) Mol. Endocrinol. 10:607–612.

Proteins identified by these techniques can be further separated on the basis of their size, net surface charge, hydrophobicity and affinity for ligands. In addition, antibodies raised against such proteins can be conjugated to column matrices and the proteins immunopurified. All of these general methods are well known in the art. See,.e.g, Scopes, R. K., Protein Purification: Principles and Practice, 2nd ed., Springer Verlag, (1987).

Transgenic Non-Animals Incorporating TERT Genes

The invention also provides non-human transgenic animals comprising heterologous TERT or recombinant constructs comprising endogenous TERT promoter. In a preferred embodiment, the transgenic animals of the invention comprise a TERT promoter driving a heterologous gene, such as a reporter gene coding sequence. In a preferred embodiment, an hTERT promoter of the invention is operably linked to a reporter gene in a transgenic mouse. Alternatively, an mTERT promoter is operably linked to a reporter gene in a transgenic mouse. These transgenic animals are very useful as in vivo animal models to screen for modulators of TERT transcriptional activity. The introduction of hTERT, mTERT or other TERT promoters into animals to generate transgenic models is also used to assess the consequences of mutations or deletions to the transcriptional regulatory regions.

In one embodiment, the endogenous TERT gene in these mice is still functional and wild-type (native) telomerase activity can still exist. A TERT promoter of the invention (e.g., hTERT or mTERT) is used to drive a high level expression of an exogenous TERT construct, the endogenously produced mTERT protein can be competitively replaced with the introduced, exogenous TERT protein. This transgenic animal (retaining a functional endogenous telomerase activity) is preferred in situations where it is desirable to retain "normal," endogenous telomerase function and telomere structure. In other situations, where it is desirable that all telomerase activity is by the introduced exogenous TERT protein, use of an mTERT knockout line (described below) is preferred.

Promoter function, and in a preferred embodiment, hTERT promoter function, can be assessed with these transgenic animals. Alterations of TERT promoters can be constructed that drive TERT or a reporter gene to assess their function and expression pattern and characteristics (the invention also provides constructs and animals and methods for gene expression driven by a TERT promoter by transient transfection).

In one embodiment, the TERT promoters and reagents of the invention are used to create mouse cells and transgenic animals in which the endogenous TERT promoter is deleted, modified, supplemented or inhibited. For example, TERT promoter sequences can be deleted, modified or inhibited on either one or both alleles. The cells or animals can be reconstituted with a wild-type or modified TERT promoter, or, in a preferred embodiment, an exogenous TERT in the form of hTERT. Methods for the construction of transgenic animals, particularly trangenic mice, and the selection and preparation of recombinant constructs for generating transformed cells are well known in the art.

Construction of a "knockout" cell and animal is based on the premise that the level of expression of a particular gene in a mammalian cell can be decreased or completely abrogated by introducing into the genome a new DNA sequence (e.g., a TERT or other nucleic acid construct of the invention) that serves to interrupt some portion of the DNA sequence of the gene/promoter to be suppressed. To prevent expression of endogenous promoter, simple mutations that alter or disrupt the promoter can be suitable. To upregulate expression, a native TERT promoter can be substituted with a heterologous or mutated TERT promoter that induces higher levels of transcription, or with multiple copies of trangene TERT promoters. Also, "gene trap insertion" can be used to disrupt a host gene, and mouse embryonic stem (ES) cells can be used to produce knockout transgenic animals, as described herein and, e.g., in Holzschu (1997) Transgenic Res 6: 97–106.

In a preferred embodiment, cell and trangenic animal models express TERT promoter (particularly, hTERT promoter) operably linked to a reporter gene. The cell or animal can be a TERT promoter "knockout" or it can retain endogenous TERT promoter activity. The insertion of the TERT promoter-containing exogenous sequence is typically by homologous recombination between complementary nucleic acid sequences. Thus, the exogenous sequence, which is typically an hTERT or mTERT promoter of this invention, is some portion of the target (e.g., mTERT) gene to be modified, such as exonic, intronic or transcriptional regulatory sequences, or any genomic sequence which is able to affect the level of the target gene's expression; or a combination thereof. The construct can also be introduced into other (i.e., non-mTERT gene) locations in the genome. Gene targeting via homologous recombination in pluripotential embryonic stem cells allows one to modify precisely the genomic sequence of interest.

The exogenous sequence is typically inserted in a construct, usually also with a marker gene to aid in the detection of the knockout construct and/or a selection gene. The construct can be any of a variety of expression vectors, plasmids, and the like, as described above. The knockout construct is inserted in a cell, typically an embryonic stem (ES) cell, using a variety of techniques, as described above. The insertion of the exogenous DNA usually occurs by homologous recombination. The resultant transformed cell can be a single gene knockout (i.e., only one of the two copies of the endogenous TERT promoter has been modified) or a double gene knockout. The knockout construct can be integrated into one or several locations in the cell's genome due to the random nature of homologous recombination events; however, the recombination does occur between regions of sequence complementarity. Typically, less than one to five percent of the ES cells that take up the knockout construct will actually integrate exogenous DNA in these regions of complementarity; thus, identification and selection of cells with the desired phenotype is usually necessary and a selection or marker sequence is usually incorporated into the construct for this purpose. Cells which have incorporated the construct are selected for prior to inserting the genetically manipulated cell into a developing embryo; for example, the cells are subjected to positive selection (using G418, for example, to select for neomycin-resistance) and negative selection (using, for example, FIAU to exclude cells lacking thymidine kinase). A variety of selection and marker techniques are well known in the art, e.g., antibiotic resistance selection or beta-galactosidase marker expression can be used and are further described herein.

After selection of manipulated cells with the desired phenotype, i.e., complete or partial inability to express endogenous TERT promoter, or, expression of the exogenous TERT promoter (as hTERT promoter activity) the cells are inserted into a mouse embryo. Insertion can be accomplished by a variety of techniques, such as microinjection, in which about 10 to 30 cells are collected into a micropipet and injected into embryos that are at the proper stage of development to integrate the ES cell into the developing embryonic blastocyst, at about the eight cell stage, which for mice is about 3.5 days after fertilization. The embryos are obtained by perfusing the uterus of pregnant females. After the ES cell has been introduced into the embryo, it is implanted into the uterus of a pseudopregnant foster mother, which is typically prepared by mating with vascectomized males of the same species. In mice, the optimal time to implant is about two to three days pseudopregnant. Offspring are screened for integration of the TERT nucleic acid sequences and the modified promoter activity phenotype. Offspring that have the desired phenotype are crossed to each other to generate a homozygous knockout. If it is unclear whether germline cells of the offspring have modified promoter, they can be crossed with a parental or other strain and the offspring screened for heterozygosity of the desired trait. The heterozygotes can be crossed, with each other to produce mice homozygous for modified TERT genomic sequence. While the above described methodology describes a typical protocol, any technique can be used to create, screen for, propagate, a knockout animal, particularly, an mTERT knockout mice, e.g., see Bijvoet (1998) Hum. Mol. Genet. 7:53–62; Moreadith (1997) J. Mol. Med. 75:208–216; Tojo (1995) Cytotechnology 19:161–165; Mudgett (1995) Methods Mol. Biol. 48:167–184; Longo (1997) Transgenic Res. 6:321–328; U.S. Pat. No. 5,616,491 (Mak, et al.); U.S. Pat. Nos. 5,464,764; 5,631,153; 5,487,992; 5,627,059; 5,272,071; and, WO 91/09955, WO 93/09222, WO 96/29411, WO 95/31560, and WO 91/12650. Thus, the invention provides for the use of the TERT promoter sequence-containing reagents of the invention to produce "knockout" mouse cells and animals, trangenic animals, and their progeny. These cells and animals can be further reconstituted with wild type or modified endogenous mTERT promoter or exogenous TERT promoter, such as hTERT.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Example 1

Cloning of Lambda Phage Gphi5 and Characterization of hTERT Genomic Sequences

The following example details the cloning of the human hTERT promoter.

Lambda Phage Gphi5

A human genomic DNA library was screened by PCR and hybridization to identify a genomic clone containing hTERT RNA coding sequences. The library was a human fibroblast genomic library made using DNA from WI38 lung fibroblast cells (Stratagene, Cat # 946204). In this fibroblast library, partial Sau3AI fragments were ligated into the XhoI site of a commercial phage cloning vector, Lambda FIX(r)II Vector (Stratagene, San Diego, Calif.), with insert sizes ranging from approximately 9 kilobases (kb) to 22 kb.

The genomic library was divided into pools of 150,000 phage each. Each pool screened by nested PCR, with the outer primer pair TCP1.52 & TCP1.57; inner pair TCP1.49 & TCP1.50, see Table 1. These primer pairs span a putative intron in the genomic DNA of hTERT and ensured the PCR product was derived from a genomic source and not from contamination by the hTERT cDNA clone. Positive pools were further subdivided until a pool of 2000 phage was obtained. This pool was plated at low density and screened via hybridization with a DNA fragment encompassing a subset of hTERT cDNA, generated by restriction digest with SphI and EcoRV.

Two positive clones were isolated and rescreened via nested PCR as described above. At rescreening, both clones were positive by PCR. One of the lambda phage clones (designated "Gphi5" or G (5) was digested with NotI, revealing an insert size of approximately 20 kb. Subsequent mapping indicated the insert size was 15 kb and that phage Gphi5 contains approximately 13 kb of DNA upstream from the transcriptional start site (upstream from the cDNA sequence). Phage Gphi5 was mapped by restriction enzyme digestion and DNA sequencing. The resulting map is shown in FIG. 1.

Isolating, Subcloning and Sequencing the Genomic hTERT Insert

The phage DNA was digested with NcoI. This fragment was cloned into the plasmid pBBS167. The resulting subclones were screened by PCR to identify those containing sequences corresponding to the 5' region of the hTERT cDNA. A subclone (plasmid "pGRN140") containing a 9 kb NcoI fragment (with hTERT gene sequence and about 4 to 5 kb of lambda vector sequence) was partially sequenced to determine the orientation of the insert. pGRN140 was digested using SalI to remove lambda vector sequences, the resulting plasmid (with removed lambda sequences) designated pGRN144. The pGRN144 insert was then sequenced.

A NotI fragment (SEQ ID NO:1) from lambda Gphi5 (containing the complete approximately 15 kbp genomic insert including the hTERT gene promoter region) was inserted in the NotI site of plasmid pBBS185. Two plasmids were isolated with their respective inserts oriented in opposite directions. One resulted in the insert oriented with the hTERT open reading frame (ORF) in the same orientation as the plasmid's Lac promoter, designated pGRN 142; the second, pGRN 143. pGRN142 has been deposited in GenBank with the Accession Number PGRN142.INS AF121948 (see National Center for Biotechnology Information at http://www.ncbi.nlm.nih.gov/ Web/Search/index.html).

The insert in pGRN 142 was sequenced; the results of which are provided as SEQ ID NO:1. In SEQ ID NO:1, the genomic insert begins at residue 44 and ends at residue 15375. The hTERT cDNA start site is at residue 13490. The hTERT ATG codon is at residue 13545. As indicated in FIG. 1, Alu sequence elements are located 1700 base pairs upstream of the hTERT cDNA 5' end.

Example 2
TERT Promoter-Driven Reporter Constructs

This example describes the construction of plasmids in which reporter genes are operably linked to hTERT promoter sequences of the invention. This also illustrates how the TERT promoter sequence of the invention can analogously be operatively linked to heterologous sequences, such as polypeptide coding sequences, for expression in cells and tissues in vitro and in vivo and transgenic animals.

hTERT-linked reporter vectors of the invention have numerous uses, including, e.g., identification of specific cis-acting sequences and trans-acting transcriptional regulatory factors. Importantly, these hTERT-containing reporter constructs can be used for the screening of agents capable of modulating (e.g., activating or inhibiting) hTERT transcription (e.g., drug screening). These studies can be in vitro and in vivo.

A number of reporter genes, e.g., firefly luciferase, beta-glucuronidase, beta-galactosidase, chloramphenicol acetyl transferase, and GFP and the like, are known in the art and can be operably linked to hTERT promoter. In this example, the human secreted alkaline phosphatase (SEAP; ClonTech) was used. The SEAP reporter gene encodes a truncated form of the placental enzyme which lacks the membrane anchoring domain, thereby allowing the protein to be secreted efficiently from transfected cells. Levels of SEAP activity detected in the culture medium have been shown to be directly proportional to changes in intracellular concentrations of SEAP mRNA and protein. The chemiluminescence-based SEAP assay is about 10-fold more sensitive than similar assays using firefly luciferase as the reporter enzyme. The SEAP activity can also be assayed with a fluorescent substrate, which provides sensitivity comparable to luciferase. See, e.g., Berger (1988) Gene 66:1; Cullen (1992) Meth. Enzymol. 216:362; Yang (1997) Biotechniques 23:1110–1114.

hTERT5' Upstream and Intronic Sequences Have "Promoter" Activity

Experiments with reporter constructs comprising various hTERT sequences of the invention identified cis-acting regions with "promoter" transcriptional activating activity in both 5' upstream and intronic sequences. In brief, four constructs, pGRN148, pGRN150, "pSEAP2 basic" (no promoter sequences=negative control), and "pSEAP2 control" (contains the SV40 early promoter and enhancer) were constructed (see also details below) and transfected in triplicate into mortal and immortal cells. Plasmid pGRN148 was constructed as illustrated in FIG. 5. Briefly, a Bgl2-Eco47III fragment from pGRN144 (described above) was digested and cloned into the BglII-NruI site of pSeap2Basic (Clontech, San Diego, Calf.).

A second reporter-promoter, plasmid pGRN150 was made by inserting the BglII-FspI fragment from pGRN144 into the BglII-NruI sites of pSEAP2. Plasmid pGRN173 was constructed by using the EcoRV-StuI fragment from pGRN144. This makes a promoter reporter plasmid that contains the promoter region of hTERT from approximately 2.5 kb upstream from the start of the hTERT ORF to just after the first intron in the coding region. The initiating Met was mutated to Leu, so that the second ATG following the promoter region would be the initiating ATG of the SEAP ORF.

Use of the intronic sequence allows identification of regulatory sequences that may be present in the intron (the invention provides transcriptional regulatory sequences from any portion of the hTERT genomic sequence). In addition to the hTERT derived pSEAP reporter constructs, a positive control vector and a negative control vector were used. The negative control (pSEAP2-Basic) is necessary to determine the background signal associated with the DNA backbone of the vector. A positive control is necessary to confirm transfection and expression of exogenous DNA and to verify the presence of active SEAP in the culture media. The positive control is the pSEAP2-Control vector (Clontech) which contains the SEAP structural gene under transcriptional control of the SV40 promoter and enhancer.

Three constructs, the control, pGRN148 (which include hTERT 5' promoter sequences) and pGRN150, were transfected into a mortal cell line, BJ cells, a human foreskin fibroblast line; see, e.g., Feng (1995) Science 269:1236; and an immortal cell line, the human embryonic kidney line 293; see, e.g., Graham (1977) J. Gen. Virol. 36:59. All transfections were done in parallel with the two control plasmids.

In immortal cells, pGRN148 and pGRN150 constructs appear to drive SEAP expression as efficiently as the pSEAP2 positive control (containing the SV40 early promoter and enhancer). In contrast, in mortal cells only the pSEAP2 control gave detectable activity. Similar results were obtained using another normal cell line (RPE, or retinal pigmental epithelial cells, see, e.g., Aronson (1983) In vitro 19:642–650). In RPE cells transfected with pGRN150, the hTERT promoter region was inactive while the pSEAP2 control plasmid was active. These results indicate that, as expected, hTERT promoter sequences are active in tumor cells but not in mortal cells.

Identification of the Tissue Specificity Elements of the hTERT Promoter

The hTERT DNA promoter sequences were cloned into the pSEAP2-Basic transcription reporter vector (Clontech) to generate the plasmids pGRN 148, 150, 175, 176, 181,184, 261, 262, and 319. Summarized below are details of the promoter plasmid construction (nucleotide numbers refer to the number of nucleotides upstream of the translation initiation site at 13545 of SEQ ID NO:1):

pEGFP-1. *Vector from Clontech containing the "Enhanced Green Flourescent Protein".

pGRN140. *NCO1 fragment containing hTERT upstream sequences and the first intron of hTERT from lambdaG-Phi5 into the NCO1 site of a pBBS167 (variant of pUC19 cloning vector with MCS, e.g. ATGACCATGATTACGAATTCGAGCTCGGTACCCG-GGGATCCTCTAGAGTCGACCTGCAGGCATGCCC-ATGGCAGGCCTCGCGCGCGAGATCTCGGGCCC-AATCGATGCCGCGGCGATATCGCTCGAGGAAGC-TTGGCACTGGCC (SEQ ID NO:3), and a chloramphenicol sensitive gene between the F1ori and the Amp gene in the opposite orientation from the Amp gene). The fragment is oriented so that the hTERT sequences are in the same direction as the Lac promoter.

pGRN144. described above; SalI deletion of pGRN140 to remove phage (lambda) sequences.

pGRN148: *BGL2-ECO47III fragment from pGRN144 containing hTERT upstream sequences (from position −51 to −2482) into the BGL2-NRUI sites of pSEAP2-Basic to make a hTERT promoter/reporter plasmid.

pGRN150: *BGL2-FSP1 fragment from pGRN144 containing 2447nt of hTERT upstream sequences (from position −36 to −2482) into the BGL2-NRU1 sites of pSEAP2 to make a hTERT promoter/reporter plasmid.

pGRN175: *APA1(Klenow blunt)-SRF1 religation of pGRN150 to delete most of the hTERT upstream sequences. This makes a promoter/reporter plasmid that uses 82 nucleotides of hTERT upstream sequences (from position −36 to −117).

pGRN176: *PML1-SRF1 religation of pGRN150 to delete most of the hTERT upstream sequences. This makes a promoter/reporter plasmid that uses 204 nucleotides of hTERT upstream sequences (from position −36 to −239).

pGRN181: *APA1 digestion and religation of pGRN150 to delete all APA1 sites but one. This makes a promoter/reporter plasmid that comprises from −36 to −114 and −1076 to −2482 of the hTERT upstream sequences.

pGRN184: *XBA1(partial, Klenow fill)-ECOR1 digest and religation of pGRN150 to make a deletion of the hTERT promoter sequences. This makes a promoter/reporter plasmid that expresses a region from −1391 to −2484 of the hTERT upstream sequences.

pGRN213. *FSP1 fragment containing the CatS gene and the F1 ORI plus part of the AmpR gene into the FSP1 sites of pSEAP2-Basic such that the orientation reconstructs the AmpR gene.

pGRN244: *SAL1-NOT1 fragment from pSEAP2-Basic containing the SEAP region into the SAL1-NOT1 sites of pEGFP-1. This modification adds a selectable marker to the vector.

pGRN245: *SAL1-NOT1 fragment from pGRN176 containing the hTERT-promoter/SEAP region into the SAL1-NOT1 sites of pEGFP-1. This modification adds a dominant selectable marker to the vector.

pGRN246: *SAL1-NOT1 fragment from pGRN176 containing the hTERT-promoter/SEAP region into the SAL1-NOT1 sites of pEGFP-1. This modification adds a dominant selectable marker to the vector.

pGRN248 *SAL1-NOT1 fragment from pGRN175 containing the hTERT promoter/SEAP region into the SalI-NotI sites of pEGFP-1. This modification adds a dominant selectable marker to the vector.

pGRN259. *in vitro mutagenesis using RA94 (CCCGGCCACCCCCGCGAattCGCGCGCTCCCCG-CTGC) (SEQ ID NO:4) to introduce an EcoRI site at the initiating met of hTERT in pGRN144. This provides hTERT u=sequences from +1 to −2482 that can be cloned into a vector using EcoRI and BglII.

pGRN260. *in vitro mutagenesis using RA91 (TTGTACTGAGAGTGCACCATATGCGGTGTGcatgc-TACGTAAGAGGTTCCAACTTTCACCATAAT) (SEQ ID NO:5) to delete several sites from the Chloramphenicol region of pGRN213 to create a variant, more useful, MCS. This creates a Mutagenesis version of pSEAP2-Basic with more unique cloning sites in it's MCS.

pGRN261: *BGL2-ECOR1 fragment from pGRN259 containing hTERT upstream sequences into the BGL2-ECOR1 sites of pSEAP2-Basic. This makes a promoter/reporter expression plasmid that contains from +1 to −2482 of the hTERT upstream sequences.

pGRN262: *BGL2-ECOR1 fragment from pGRN259 containing hTERT upstream sequences into the BGL2-ECOR1 sites of pGRN260. This makes a promoter/reporter expression and mutagenesis plasmid that contains from +1 to −2482 of the hTERT upstream sequences.

pGRN294. *BbsI-XhoI fragment from pGRN142 containing hTERT upstream sequences from −1667 to −3278 into the BbsI-XhoI sites of pGRN259. This makes a vector containing the genomic upstream region for hTERT from +1 to −3278 that can be cloned with EcoRI and XhoI.

pGRN295: *ECOR1-XHO1 fragment from pGRN294 containing from +1 to −3282 of hTERT upstream sequences into the ECOR1-XHO1 sites of pGRN260. This makes a SEAP promoter/reporter/mutagenesis plasmid.

pGRN296: *ECOR1-XHO1 fragment from pGRN294 containing from +1 to −3282 of the hTERT upstream sequences into the ECOR1-XHO1 sites of pSEAP2-Basic. This makes a SEAP promoter/reporter plasmid.

pGRN297. *RA96 (AATTGCGAAGCTTACG) (SEQ ID NO:6) and RA97 (AATTCGTAAGCTTCGC) (SEQ ID NO:7) annealed to make an oligo linker into the ECOR1 sites of pGRN259 replacing the ECOR1 fragment of the intron-exon region of pGRN259.

pGRN299: *XHO1-HIND3 fragment from pGRN298 containing from +1 to −3282 of the hTERT upstream sequences into the XHO1-HIND3 sites of pGL2-Basic. This makes a Luciferase promoter/reporter plasmid with about 3.3 Kb of hTERT promoter sequences.

pGRN300: *XHO1-SAC1 fragment from pGRN142 containing hTERT upstream sequences into the XHO1-SAC1 sites of pGRN299 such that the resulting construct contains from +1 to −5124 of the hTERT upstream sequences. This creates an hTERT promoter/reporter construct using Luciferase as a reporter.

pGRN310: *SAC1 fragment from pGRN142 containing hTERT upstream sequences into the SAC1 site of pGRN300 such that the resulting construct contains +1 to −7984 of the hTERT upstream sequences. This creates an hTERT promoter/reporter construct using Luciferase as a reporter.

pGRN311. *SPE1 fragment from pGRN142 containing from −4773 to −13501 of the hTERT upstream sequences into the SPE1 site of pGRN300 such that the orientation reconstructs the genomic region. This makes a Luciferase promoter reporter plasmid that contains the entire pGRN142 upstream genomic region of hTERT plus a 365 bp region of genomic DNA from the middle of the 13.5 Kb genomic region repeated upstream of the T7 promoter.

pGRN312: *BGL2-FSP1 fragment from pGRN144 into the BGL2-HIND3 (Klenow filled) sites of pGL2-Basic. This makes a Luciferase promoter/reporter version of pGRN150.

pGRN313: *KPN1-NOT1 digested pGRN311 blunted with T4 polymerase and religated. This makes a Luciferase promoter/reporter plasmid using from +1 to a −13501 of the hTERT upstream sequences.

pGRN316: *oligo RA101 (5'-TAGGTACCGAGCTCTTA-CGCGTGCTAGCCCCACGTGGCGGAGGGACTGG-GGACCCGGGCA-3') (SEQ ID NO:8) used for in vitro mutagenesis to delete the genomic sequence from pGRN262 between the SRF1 site and the first PML1 site. This makes a promoter-reporter plasmid containing hTERT upstream sequences from +1 to −239.

pGRN317: *oligo RA100 (5'-TAGGTACCGAGCTCTTA-CGCGTGCTAGCCCCTCGCTGGCGTCCCTGCAC-CCTGGGAGCGC-3') (SEQ ID NO:9) used for in vitro mutagenesis to delete the genomic sequence from pGRN262 between the SRF1 site and next to the last APA1 site. This makes a promoter- reporter plasmid containing hTERT upstream sequences from +1 to −397.

pGRN319: *RA107 (5'-CGTCCTGCTGCGCACtcaGGA-AGCCCTGGCCCC-3') (SEQ ID NO:10) used for in vitro mutagenesis to inactivate the 'B' class E-box just proximal to the hTERT initiating met in pGRN262. This changes the CACGTG (SEQ ID NO:1 1) to CACTCA (SEQ ID NO:12). Also COD1941 (5'-GATGAATGCTCATGATTCCG TATGGCA-3') (SEQ ID NO:13) was used to switch from CatR to CatS introducing a BSPH1 site and COD2866 (5'-CAGCATCTTTTACTTTCACCAGCGTTTCTGGG-TGCGCAAAAACAGGAAGGCAAAATGCC-3') (SEQ ID NO:14) was used to select from AmpS to AmpR introducing an FSP 1 site. In summary, pGRN319 carries a mutation in the E-box.

pGRN350: *RA104 (5'-TAGGTACCGAGCTCTTACGC-GTGC TAGCCCCTCCCAGCCCCTCCCCTTCCTTT-CCGCGGC-3') (SEQ ID NO:15) used for in vitro mutagenesis to delete the genomic sequence from pGRN262 between the SRF1 site and the last APA1 site before the ATG of the hTERT open reading frame (orf).

pGRN351: *SAC2 fragment from pGRN319 into the SAC2 sites of pGRN350 such that the SEAP orf is recreated. This makes a "deactivated E-box" version of pGRN350.

pGRN352: *RA122 (5'-GACCGCGCTTCCCACtcaGCG-GAGGGACTGGGG-3') (SEQ ID NO:16) used for in vitro mutagenesis to "deactivate" the penultimate class "B" E-box before the translation start site of hTERT.

The pSEAP2-Basic plasmid lacks eukaryotic promoter and enhancer sequences. This vector contains the SV40 late polyadenylation signal inserted downstream of the SEAP coding sequences to ensure proper and efficient processing of the transcript in eukaryotic cells. It also contains a synthetic transcription blocker (TB), composed of adjacent polyadenylation and transcription pause sites to reduce background transcription. As noted above, the SEAP reporter gene encodes a truncated form of the placental enzyme which lacks the membrane anchoring domain, thereby allowing the protein to be efficiently secreted from transfected cells.

Levels of SEAP activity detected in the culture medium have been shown to be directly proportional to changes in intracellular concentrations of SEAP mRNA. The chemiluminescent SEAP substrate CSPDTM (Clontech) was used to detect secreted SEAP. Use of this substrate enables monitoring of the expression of the SEAP reporter gene through simple, sensitive, nonradioactive assays of secreted phosphatase activity. This chemiluminescent assay can detect as little as 10–13 g of SEAP protein. The assay is linear over a 104 fold range of enzyme concentrations. This makes the assay (and these vectors) particularly well-suited for comparative analyses.

As above, in addition to the hTERT derived pSEAP reporter constructs, a positive control vector (pSEAP2-Control vector) and a negative control vector (pSEAP2-Basic) were used. The promoter constructs (pGRN 150, 175, 176) and the control vectors were transfected into immortal (HEK 293) and mortal (BJ fibroblast, RPE, HUVEC) cells 48–72 hours after transfection. The culture media was collected and assayed for SEAP activity. The SEAP activity was detected using the chemiluminescent assay from CLONTECH, Great EscAPeTM SEAP Chemiluminescence Kit, according to the manufacturer's protocol. The transfections were performed in triplicate. The culture media from each transfection was collected after 48–72 hours and assayed in triplicate. The background values obtained by transfection of the negative control (pSEAP2-Basic) vector was subtracted from the values obtained with the test constructs. The average of nine measurements was used and plotted for each of the constructs.

Experimental Results in Immortal and Mortal Cell Lines

The results of the assays show that while the hTERT promoter constructs are capable of driving the expression of the reporter SEAP gene in immortal cells, the same constructs are silent in all mortal cells tested. The pSEAP2-Control vector however is active in all cell types regardless of their mortal or immortal status and the pSEAP2-Basic vector is silent in all cells assayed.

hTERT Promoter Driving Thymidine Kinase Expression In vitro

The invention provides constructs comprising heterologous coding sequences operably linked to hTERT promoter sequences. In one embodiment, hTERT coding sequences are operably linked to Herpes simplex virus thymidine kinase ("HSV-TK") coding sequences. HSV-TK is an enzyme that is capable of converting innocuous prodrugs, e.g. ganciclovir, into toxic metabolites that interfere with the cellular replication of proliferating cells (e.g., cancer cells, which have active hTERT promoter activity). Controlling thymidine kinase (TK) expression by subordinating it to the hTERT promoter restricts TK expression to cells where the hTERT promoter is normally active, i.e., tumor cells and other proliferating (e.g., immortalized) cells. This prevents TK expression in "normal" cells, where the hTERT promoter is usually silent.

The ability of the hTERT promoter to specifically drive the expression of the TK gene in tumor cells was tested using a variety of constructs: One construct, designated pGRN266, contains an EcoRI-FseI PCR fragment with the TK gene cloned into the EcoRI-FseI sites of pGRN263. pGRN263, containing approximately 2.5 kb of hTERT promoter sequence, is similar to pGRN150, described above, but contains a neomycin gene as selection marker. pGRN267 contains an EcoRI-FseI PCR fragment with the TK gene cloned into the EcoRI-FseI sites of pGRN264. pGRN264, containing approximately 210 bp of hTERT promoter sequence, is similar to pGRN176, described above, but contains a neomycin gene as selection marker. pGRN268 contains an EcoRI-XbaI PCR fragment with the TK gene cloned into the EcoRI-XbaI (unmethylated) sites of pGRN265. pGRN265, containing approximately 90 bp of hTERT promoter sequence, is similar to pGRN175, described above, but contains a neomycin gene as selection marker.

These hTERT promoter/TK constructs, pGRN266, pGRN267 and pGRN268, were re-introduced into mammalian cells and TK/+stable clones (and/or mass populations) were selected. Ganciclovir treatment in vitro of the TK/+ cells resulted in selective destruction of all tumor lines tested, including 143B, 293, HT1080, Bxpc-3, DAOY and NIH3T3. Significantly, ganciclovir treatment had no effect on normal BJ cells. This clearly demonstrates the tumor-specificity of all three hTERT promoter fragments used in these experiments.

Example 3
Direct In vivo hTERT Promoter Suicide Gene Therapy

The invention provides reagents and methods for treating diseases involving unwanted cell proliferation by in vivo gene therapy. To demonstrate the efficacy of this aspect of the invention, the reagents of the invention were used to treat cancer (of human origin) in an art-accepted animal model. A human cancer cell, the osteosarcoma cell line 143B, which normally expresses the telomerase gene, was transfected with a plasmid containing the TK gene driven by the hTERT promoter.

Specifically, sequences −36 to −2482 upstream of the translation start site of SEQ ID NO:1 were used to drive the TK gene. The plasmid also contained the neomycin phosphotransferase gene. After transfection of cells with the plasmid, G418 resistant clones expressing TK were selected. Two hundred thousand of the parental or TK expressing 143B cells were injected subcutaneously in the flank of Balb/c nude (nu/nu) mice to establish tumors. Four to 11 days after tumor implantation the mice were injected IP with 75 mg/kg ganciclovir (GCV) or saline twice daily. Tumor growth was monitored every 3–4 days. When GCV was administered either at 4 or at 11 days post tumor implantation to these tumor bearing animals, TK mediated cell lysis and retarded tumor growth was observed. Such inhibition of tumor cell growth is not observed when saline is administered or if the parental 143B tumor (143BP) is treated with either saline or GCV. Forty-five days after tumor implantation, only the animals implanted with the TK+ 143B clone and treated with GCV showed 100% survival. In the other groups all but one animal died from massive tumor burden.

These data indicate that the hTERT promoter is sufficient to drive TK gene expression both in vivo. It also shows that the reagents and methods of the invention can be used to promote tumor regression in vivo in animals carrying pre-established tumors; i.e., the reagents of the invention can be used to treat cancer patients with pre-existing tumors.

Example 4
Oncolytic Viruses Under Control of the hTERT Promoter

As discussed above, the invention provides "conditionally replicating" oncolytic virus constructs (e.g., gene therapy vectors) in which hTERT promoter sequences of the invention are operably linked to essential virally encoded genes. Use of hTERT promoter sequences of the invention ensures the virus will only be productively expressed in cells with telomerase activity. Thus, constructs can be used therapeutically to lyse only cells that express telomerase, such as immortal or cancer cells. Proliferation of the virus and its cytopathic effects is thus restricted to tumor cells. Details of the construction of an exemplary hTERT promoter driven, conditionally replicating oncolytic virus follows. In this embodiment, the hTERT promoter replaces the normal E1a promoter to create a virus which will only replicate in telomerase expressing cells.

Plasmid pBR/ITR/549-ClaI containing nucleotides 1–356 (Ad2 ITR and packaging signals) and 549–920 (a portion of the E1a coding sequence) of Adenovirus 2 (Ad2) linked using a polylinker was built using standard molecular biology procedures in the bacterial plasmid pBR322. In pBR/ITR/TB+phTERT176-E1A and pBR/ITR/TB+phTERT316-E1A, the normal E1a promoter (Ad2 357–548) has been replaced with the hTERT promoter. Ad2 sequences from 916–10680 are added to these plasmids to recreate the expression elements of the 5' end of the virus.

These plasmids (pBR/ITR/TB+phTERT176-10680 and pBR/ITR/TB+phTERT316-10680) are transfected into a telomerase expressing human cell line along with an adenoviral DNA fragment containing Ad2 sequences 10681–35937. Recombinant plaques are scored and selected 7–21 days post transduction. The hTERT promoter E1a containing Ad2 is propagated and produced for use employing standard schemes for recombinant Ad2 amplification and manufacturing. (Graham and Prevec, 1991, in Methods in Molecular Biology, Chapter 11, Ed E. J. Murray, The Human Press Inc., Clifton, N.J.; Kanegae et al., Jpn J Med Sci Biol, 1994, 47(3):157–66). Because the E1a gene is driven by the hTERT promoter, which is not normally expressed by most somatic cells, recombinant Ad2 genome will only replicate and be packaged into virus particles in cells expressing telomerase (i.e., immortal cells, tumor cells).

Example 5
hTERT Promoter Sequences Driving an Alkaline Phosphatase Reporter Gene for High Throughput Screening The invention provides constructs and promoter-based assays to identify small molecule activators and/or repressors of hTERT and telomerase activity. To this end, fragments of the hTERT promoter were cloned into plasmids expressing a secreted form of alkaline phosphatase and a selection marker. The SEAP constructs described above (pGRN244, pGRN245, pGRN246 and pGRN248) were re-introduced into normal human cells and into immortal cell lines. After selection of stable clones having integrated the hTERT promoter/SEAP constructs, RT-PCR was used to determine the levels of SEAP mRNAs. In 293 cells, the levels of SEAP mRNA were elevated and comparable to the levels of endogenous hTERT, whereas in BJ cells, the levels of SEAP mRNA were virtually undetectable and closely matched the levels of the endogenous hTERT in these cells.

These results indicate that hTERT promoter/SEAP constructs can be used to engineer cells suitable for promoter-based assays and to screen for chemical and/or biological activators and/or repressors of telomerase in normal and tumor cells. pGRN244, pGRN245, pGRN246 and pGRN248 were re-introduced into BJ and 293 cells. SEAP activity and mRNA levels were determined in these cells as criteria for clone selection. Several 293 and BJ lines were selected and two BJ/pGRN245 clones were expanded for high throughput screening. These constructs were also introduced into IDH4 cells, which are immortal lung fibroblasts that express the SV40 large T antigen under the control of the dexamethasone-inducible MMTV promoter. IDH4 cells are telomerase positive and proliferate in the presence of dexamethasone. However, these cells can be induced into a senescent, telomerase negative stage after dexamethasone removal. Upon re-addition of dexamethasone, the cells return to an immortal phenotype and re-activate telomerase.

pGRN244, pGRN245, pGRN246 and pGRN248 were transfected into IDH4 cells. SEAP activity was shown to parallel telomerase activity in the different clones, whereas no significant fluctuation of SEAP activity was observed with the control plasmid. These results indicate that a fragment of approximately 2.5 kb of hTERT promoter sequence (pGRN245) contains sufficient sequence elements to support both activation and repression in response to proliferation and/or growth arrest stimuli that control telomerase activity in IDH4 cells. Two clones, ID245–1 and ID245–16 whose SEAP profile closely matched telomerase activity during drug treatment, were selected and expanded for high throughput screening of small molecule activators of telomerase.

Example 6
hTERT Promoter Sequences Driving a β-galactosidase Reporter Gene to Identify Biological Regulators of hTERT and Telomerase Activity The invention also provides constructs and promoter-based assays to identify biological modulators of hTERT and telomerase activity. An exemplary construct of this aspect of the invention is pGRN353 containing a BglII-HindIII fragment from pGRN297 with approximately 2.5 kb of hTERT promoter sequences cloned into the BglII-HindIII sites of β-gal-Basic (Clontech). pGRN353 or similar constructs are re-introduced into BJ cells by co-transfection with a plasmid containing a hygromycin gene as selection marker. Clonal cell lines and/or mass populations are established and used to screen retroviral based cDNA libraries for genes or fragments of genes that can activate the hTERT promoter. pGRN353 or similar constructs are also re-introduced into 143B and 293 cells to screen retroviral libraries to identify sequences that can repress the hTERT promoter.

Example 7
Identifying Trans-Acting Transcriptional Regulatory Elements

The promoter-reporter (and other) vectors of the invention are also used to identify trans-acting transcriptional regulatory elements. As noted supra, plasmids in which reporter genes are operably linked to hTERT promoter sequences are extremely useful for identification of trans-acting transcriptional modulatory agents and for the screening of potential hTERT promoter-modulating drugs (including biological agents and small molecules, as discussed above). Both transient and stable transfection techniques can be used. In one embodiment, stable transformants of pGRN148 are made in telomerase negative and telomerase positive cells by cotransfection with a eukaryotic selectable marker (such as neo), according to Ausubel, supra.

The resulting cell lines are used for screening of putative telomerase trans-acting (e.g., promoter sequence binding) transcriptional modulatory agents, e.g., by comparing hTERT-promoter-driven expression in the presence and absence of the test compound (the putative trans-acting transcriptional modulating agent). Additional promoter-reporter vectors (including the constructs described herein, as variations thereof) are similarly used to identify and isolate trans-acting factors binding to cis-acting transcriptional regulatory elements, such as, Myc, Sp 1, TATA box binding protein, AP-1, CREB, CAAT binding factor and factors binding to hormone response elements (e.g., GRE). The identification and isolation of such trans-acting regulatory sequences provide for further methods and reagents for modulating the transcription and translation of telomerase.

Example 8
c-Myc acts as a Potent Activator of the TERT Promoter by Direct Interaction with Cis-Acting Regulatory Sequences Use of recombinant constructs comprising TERT promoter sequences of the invention has, for the first time, demonstrated that c-Myc acts as a potent activator of telomerase activity by direct interaction with cis-acting regulatory sequences in the TERT promoter. Significantly, the studies of the invention also show that transcriptional activation of the hTERT promoter by c-Myc can be abrogated by deletion or mutation of a single cis-acting regulatory sequence, the "Myc/Max binding site."

To determine whether experimental induction of c-Myc can lead to the de novo activation of telomerase in primary human cells, pre-senescent IMR90 cultures engineered to express the mouse ecotropic receptor (Serrano et al. (1997) Cell 88, 593–602) were transduced with either the pBABE retroviral vector or one encoding a hormone inducible c-Myc-Estrogen Receptor (cMycER) fusion protein (Eilers et al., 1989 Nature 340, 66–68; Littlewood (1995) Nuc. Acids Res. 23, 1686–1690). IMR90 cultures do not possess detectable telomerase activity or TERT gene expression (Nakamura et al., 1997; Meyerson et al., 1997).
Retroviral Infection The mouse ecotropic receptor was transduced into IMR90 fibroblasts and all subsequent transductions with ecotropic retrovirus were carried out according to Serrano et al. (1997). pBABE-MycER and pBABE vector control viruses were harvested from stable expressing_2 cell lines.
Cell Culture IMR90 cells were grown in Dulbecco's Modified Eagle Medium (DMEM) (Gibco/BRL) supplemented with 10% fetal bovine serum (FBS), 0.29 mg/mL L-glutamine, 0.03% penicillin and streptomycin, and 25 ug/mL gentamycin sulfate. For the Myc induction studies in IMR90 cells, MycER transduced cells were exposed to 2 uM 4-OHT for 24, 48 and 72 hours. For the promoter studies NIH 3T3 cells were exposed to 1 uM 4-OHT for 24 and 72 hours. In all cases uninduced controls were treated with an equivalent volume of ethanol, the solvent for 4-OHT.
Telomerase Assays Telomerase activity was measured by a modified telomerase repeat amplification protocol using the TRAPeze telomerase detection kit (Oncor, Gaithersburg, Md.) (Kim et al., 1994). Genomic DNA was obtained from vector control or MycER transduced IMR90 fibroblasts. TRAP assays were performed on lysates equivalent to 1000 cells for all samples, with 293T cell lysates serving as a positive control for telomerase activity. PCR internal controls from each experiment were amplified equally. Inactivation of lysate was for 5 minutes at 85° C. prior to the TRAP assay.

In the MycER system, the Myc moiety exists in a latent form bound in a complex with HSP-90 through its ER fusion (Eilers et al., 1989; Littlewood et al., 1995). Upon treatment with 4-hydroxy-tamoxifen (4-OHT), the MycER protein is liberated from HSP-90, resulting in a Myc over-expression phenotype (Eilers et al., 1989; Littlewood et al., 1995). Employing this cell culture system, 4-OHT treatment of MycER-transduced IMR90 cultures resulted in the marked and sustained activation of telomerase to a level at or above that detected in lysates derived from an equivalent number of telomerase-positive 293T tumor cells, as assayed by the sensitive TRAP assay. In contrast, untreated MycER-transduced or 4-OHT-treated pBABE-transduced IMR90 cultures remained telomerase negative. Western blot analysis confirmed abundant MycER protein levels in the MycER-transduced cultures in the presence or absence of 4-OHT.

Notably, enforced expression of oncogenes such as H-Ras, and cellular modulators of the Rb and p53 pathways (E7, cyclin D1, Mdm2, dominant-negative p53) have not been found to be capable of influencing telomerase activity in IMR90 cells (Wang et al., 1998).

c-Myc Enhancement of hTERT Transcription Requires the Presence of a Cis-Acting Promoter Element: the Proximal Myc-Binding "E-Box"

hTRT Reporter Construction: The pGRN150 (E box deleted), pGRN261 (2.5 kbp hTRT reporter) are described above. NIH 3T3 cells were grown in Dulbecco's Modified Eagle Medium (DMEM) (Gibco/BRL) supplemented with 10% fetal bovine serum (FBS), 0.29 mg/mL L-glutamine, 0.03% penicillin and streptomycin, and 25 ug/mL gentamycin sulfate. NIH 3T3 cells were transfected using Lipo-Fectamine reagent (Life Sciences) with 100 ng of a promoter reporter, and 200 ng of pCMX-β-Galactosidase which served as an internal control for transfection efficiency. Transfected cells were allowed to recover for 6 hours in complete DMEM and then treated with 1 uM 4-OHT or ethanol for 36 hours prior to analysis of secreted alkaline phosphatase activity using the Great EscAPe assay (Clontech). β-galactosidase activity was assayed by incubation of whole cell extracts with 400 ug/ml ONPG in buffer containing 60 mM Na2HPO4, 40 mM NaH2PO4, 10 mM KCl and 1 mM MgSO4 and relative transfection efficiencies determined by reading absorbance at 415 nm.

Expression of endogenous hTRT following exposure to 4-OHT (or solvent alone) was measured at various times in the presence of 1_M cyclohexamide in IMR90 fibroblasts transduced with MycER. Reverse transcription of RNA derived from each sample followed by PCR and Southern blotting of the amplified products was carried out as described above. Glyceraldehyde-6-phosphate dehydrogenase (GAPDH) was amplified from the same reverse transcription products as an internal semi-quantitative control and visualized by ethidium bromide staining. Low level expression of hTRT mRNA was detected in uninduced samples after very long exposures; however, the level of hTRT mRNA did not change over time in the uninduced samples.

The activity of the hTERT promoter was dramatically enhanced by c-Myc-ER in NIH 3T3 cells. The ability of c-Myc-ER to enhance hTERT promoter activity was dependent upon sequences in the hTERT promoter that included an evolutionarily conserved Myc binding site (E-box). To determine whether the increased telomerase activity induced by activation of c-Myc-ER was a result of increased transcription of the hTERT gene we initially examined the effect of 4-OHT induction of c-Myc-ER activity upon hTERT promoter sequences placed upstream of the secreted alkaline phosphatase reporter gene. The hTERT promoter contains two putative Myc-binding sites positioned at −242 and −34 relative to the ATG initiation codon.

NIH 3T3 cells engineered to express c-Myc-ER stably were transfected with constructs containing a secreted alkaline phosphatase reporter under the control of a 2.5 kb fragment of the hTERT promoter, a 2.5 kb fragment of the hTERT promoter lacking the proximal E-box, or a promoterless reporter construct. The basal activity of the wild-type hTERT promoter and that of the hTERT promoter lacking the proximal E-box were equivalent and approximately 3 fold higher than the activity of the promoterless reporter. Induction of c-Myc-ER activity with 1_M 4-OHT enhanced the activity of the 2.5 kb hTERT promoter approximately 10 fold. By contrast, the activity of the promoter lacking the proximal E-box was not significantly affected by induction of c-Myc-ER. Similarly, the promoterless reporter was not affected by induction of c-Myc-ER. To further confirm the role of the proximal E-box in regulating the hTERT promoter we tested the effect of changing the E-box from CACGTG to CACTCA. The mutation in the E-box reduced the promoter activity due to 4-OHT stimulation to the equivalent of the E-box deletion and 10-fold below the wild-type promoter. This demonstrates that c-Myc-ER is not able to significantly activate an hTERT promoter with an attenuated E-box at −34 and that the E-box at −242 is not able to significantly mediate c-Myc activation. These results suggest that the ability of c-Myc to stimulate the hTERT promoter is mediated via the −34 E-box.

hTERT is a Direct Target of c-Myc Regulated Transcription

To confirm the ability of c-Myc to stimulate transcription of the hTERT gene directly, we assayed for hTERT gene expression in MycER-transduced cultures of IMR90 cells 0, 1, 3 and 9 hours following the addition of 4-OHT. The cultures were treated with cyclohexamide for 30 minutes prior to addition of 4-OHT to prevent de novo protein synthesis. hTERT expression was undetectable at the zero hour time point for the Myc transduced cultures. Pretreatment of these cells with cyclohexamide alone had no effect on expression of hTERT mRNA. Induction of the c-Myc-ER activity by treatment with 2 M 4-OHT in the presence of 1 cyclohexamide led to a rapid increase in expression of hTERT message.

hTERT expression was detected by 1 hour post-induction, and increased 3 and 9 hours post induction. By contrast, cells treated with solvent alone were not induced to express hTERT. Furthermore, the expression level of GAPDH was similar at all time points in cells treated with 4-OHT or solvent alone. These observations strongly suggest that Myc acts directly upon the hTERT promoter to enhance transcription of the hTERT gene.

Lack of Equivalence of Myc and TERT in Cellular Transformation

To further explore the functional implications of Myc induction of telomerase activity in primary cells, we examined whether TERT could substitute for c-Myc as an immortalizing agent in the rat embryonic fibroblast (REF) cooperation assay. In this assay, co-transfection of Myc and activated RAS (H-RASG12V) effects the malignant transformation of early passage REFs. This cooperative activity can be quantified by monitoring the number of transformed foci appearing in the monolayer 7 to 10 days post-transfection. In two separate experiments, various combinations of the expression constructs encoding c-myc, H-RASG12V, TERT, or vector control were introduced into early passage REFs. Strong cooperative activity was observed in the RAS and Myc co-transfections as evidenced by an average of 34 foci per 10 cm plate; while Ras alone generated between 0 and 3 foci per plate; consistent with previous findings that an immortalizing agent and activated RAS are required for efficient transformation of primary rodent cells (Land et al., 1983). By contrast, co-transfection of TERT and RAS did not generate transformed foci counts above that scored for the RAS alone controls. These results indicate that expression of hTERT is insufficient to account for the immortalizing function of Myc in a rat embryonic fibroblast (REF) cooperation assay.

Effect of c-Myc-ER on the activity of the hTRT promoter in NIH3T3 cells was determined by detection of secreted alkaline phosphatase activity. Cells were treated with 4-OHT for 36 hours. Uninduced cells were treated with solvent alone for 36 hours. The detected secreted alkaline phosphatase activity was corrected for transfection efficiency in each case using β-galactosidase.

Example 9

Cloning of Mouse TERT Promoter

The following example details the cloning of the mouse mTERT promoter.

mTERT Construction

A hybridization probe (nucleotides 1586–1970) of the mTERT cDNA (pGRN188) was used to identify a recombinant phage (mTERT1) from a 129SV mouse genomic phage library (Stratagene). An 8 kb HindIII fragment of mTERT1 that hybridized to the 1586–1970 probe was subcloned into pBluescript II KS+(Stratagene) to generate clone B2.18. The regions encompassing the initiator and promoter were sequenced. The sequence is provided in FIG. 5. The sequence has been deposited as GenBank Accession No. B2.18 AF121949.

The human and mouse promoter sequences were aligned using the GAP program from the Wisconsin GCG package using a value of 48 for gap creation and a value of 3 for gap extension. Using a small portion of the coding region (~450 bases) was found to improve the initial alignment. See FIGS. 4A and 4B.

Conservation of Human and Mouse TERT Promoters

To determine whether the ability of c-Myc to enhance telomerase activity was mediated through increased transcription of the hTERT gene, we compared the sequences of the human and mouse TERT promoters. Alignment of the first 300 bases of the human and mouse promoters indicates a number of conserved regions (FIG. 4A). In particular, the Myc/Max binding site (E-box) located at –34 of the human promoter and at –32 of the mouse promoter, are highly conserved, as discussed above. A second E-box was identified at –242 of the human promoter; however, this site was not conserved in the mouse promoter. These observations raised the possibility that the conserved Myc binding site in particular might play a role in the regulation of hTERT expression by c-Myc References Bello-Fernandez. (1993). Proc Natl Acad Sci U S A. 90,7804–8.
Bishop (1991). C.S.H. Symp. Quant. Biol. 56, 99–107.
Bodnar (1996). Expt. Cell Res. 228, 58–64.
Bodnar (1998). Science 279,349–52.
Counter (1992).EMBO J. 11, 1921–1929.
Eilers (1989). Nature 340, 66–68.
Eilers (1991). EMBO J. 10,133–41.
Fujimoto.(1997). Biochem. & Biophys. Res. Comm. 241, 775–781.
Galaktionov (1996). Nature 382, 511–7
Grandori (1996). EMBO J. 15,4344–57
Grandori (1997). TIBS 22, 177–181.
Greenberg, (1998) Oncogene 16,1723–30.
Harley (1990). Nature 345, 458–460.
Harrington. (1997). Genes Dev. 11, 3109–3115.
Hastie (1990) Nature 346, 866–868.
Hiyama (1995). Nature Med. 1, 249–255.
Kilian (1997). Hum. Mol. Genet. 6, 2011–2019.
Kim, (1994) Science 266, 2011–2015.
Kiyono (1998). Nature 396, 84–88.
Klingelhutz (1996) Nature 380, 79–82.
Land (1983) Nature 304, 596–602.
Lee (1997) Proc Natl Acad Sci U S A 94,12886–91.
Marhin (1997) Oncogene 14, 2825–34.
Meyerson (1997) Cell 90, 785–795.
Nakamura (1997) Science 277, 955–959.
Nakayama (1998) Nature Genet. 18, 65–68.
Reed (1986) Proc. Natl. Acad. Sci USA 83, 3982–3986.
Schreiber-Agus (1995) Cell 80, 777–786.
Smith (1998) Science 282,1484–7.
van Steensel (1997) Nature 385,740–3.
Vaziri (1998) Curr. Biol. 8, 279–282.
Wagner. (1993) Cell Growth Differ. 4,879–83.
Wang. (1998) Genes Dev. 12, 1769–74.
Wright. (1995) Trends Cell Biol. 5, 293–297.
Xu (1997) Oncogene 15, 2589–2596.

What is claimed is:

1. A polynucleotide in which a promoter is operably linked to a heterologous encoding region,
   wherein the promoter contains a nucleotide sequence that is least 90% identical to the sequence from position −117 to position −36 from the translation initiation site (position 13545) of SEQ. ID NO:1,
   and wherein the promoter causes the encoding region to be transcribed preferentially in human cells that endogenously express telomerase reverse transcriptase (TERT) compared with human cells that do not endogenously express TERT.

2. The polynucleotide of claim 1, wherein the promoter contains a nucleotide sequence that is at least 80% identical to the sequence from position −239 to position −36 from the translation initiation site of SEQ. ID NO:1.

3. The polynucleotide of claim 1, wherein the promoter contains a nucleotide sequence that is at least 95% identical to the sequence from position −239 to position −36 from the translation initiation site of SEQ. ID NO:1.

4. The polynucleotide of claim 1, wherein the promoter contains the sequence from position −117 to position −36 from the translation initiation site of SEQ. ID NO:1.

5. The polynucleotide of claim 1, wherein the promoter contains the sequence from position −239 to position +1 from the translation initiation site of SEQ. ID NO:1.

6. The polynucleotide of claim 1, wherein the promoter is between about 400 to 900 nucleotides in length.

7. The polynucleotide of claim 1, wherein the promoter is between about 200 to 400 nucleotides in length.

8. The polynucleotide of claim 1, wherein the promoter is between about 100 to 200 nucleotides in length.

9. The polynucleotide of claim 1, wherein the encoding region encodes human telomerase reverse transcriptase.

10. The polynucleotide of claim 1, wherein the encoding region encodes a reporter protein detectable by fluorescence, phosphorescence, or enzymatic activity.

11. The polynucleotide of claim 10, wherein the reporter protein is selected from luciferase, glucuronidase, chloramphenicol acetyl transferase, green fluorescent protein, alkaline phosphatase, and galactosidase.

12. The polynucleotide of claim 1, wherein said heterologous encoding region encodes a product that is toxic to the cell or renders the cell more susceptible to toxicity of a drug,.

13. The polynucleotide of claim 12, wherein the encoding region encodes a protein selected from ricin, diphtheria toxin, other polypeptide toxins, thymidine kinase, and an enzyme that induces apoptosis.

14. The polynucleotide of claim 12, wherein the drug is ganciclovir.

15. A viral vector comprising the polynucleotide of claim 1.

16. The vector of claim 15, which is an adenovirus vector.

17. A mammalian cell comprising the polynucleotide of claim 1.

18. A method of expressing an encoding region in a cell, comprising contacting the cell in vitro with the polynucleotide of claim 1.

19. A method of killing a mammalian cell that expresses TERT, comprising expressing the polynucleotide of claim 12 in the cell in vitro, wherein said heterologous encoding region encodes a product that is toxic to the cell.

20. The method of claim 19, wherein the cell that expresses TERT is a cancer cell.

21. A method of screening a compound that modulates expression of telomerase reverse transcriptase (TERT), comprising contacting a cell transfected with a polynucleotide according to claim 10 with the compound in vitro, and correlating any resulting change in expression of the reporter protein with an ability of the compound to modulate TERT expression.

22. A method of producing a protein, comprising expressing a polynucleotide according to claim 1 in a cell in vitro, wherein said heterologous encoding region encodes the protein.

23. A method of killing a mammalian cell that expresses TERT, comprising expressing the polynucleotide of claim 12 in the cell in vitro, wherein said heterologous encoding region encodes a product that makes the cell more susceptible to toxicity of said drug.

* * * * *

SEQUENCE LISTING

```
<160> NUMBER OF SEQ ID NOS: 23

<210> SEQ ID NO 1
<211> LENGTH: 15418
<212> TYPE: DNA
<213> ORGANISM: Homo sapiens
<220> FEATURE:
<223> OTHER INFORMATION: Human TERT promoter

<400> SEQUENCE: 1
gcggccgcga gctctaatac gactcactat agggcgtcga ctcgatcaat ggaagatgag        60
gcattgccga agaaaagatt aatggatttg aacacacagc aacagaaact acatgaagtg       120
aaacacagga aaaaaagat aaagaaacga aaagaaaagg gcatcagtga gcttcagcag        180
aagttccatc ggccttacat atgtgtaagc agaggccctg taggagcaga ggcaggggga       240
aaatacttta agaaataatg tctaaaagtt tttcaaatat gaggaaaaac ataaaaccac       300
agatccaaga agctcaacaa aacaaagcac aagaaacagg aagaaattaa aagttatatc      360
```

-continued

```
acagtcaaat tgctgaaaac cagcaacaaa gagaatatct taagagtatc agaggaaaag      420
agattaatga caggccaaga aacaatgaaa acaatacaga tttcttgtag gaaacacaag      480
acaaaagaca ttttttaaaa ccaaaaggaa aaaaaatgct acattaaaat gttttttacc      540
cactgaaagt atatttcaaa acatatttta ggccaggctt ggtggctcac acctgtaatc      600
ccagcacttt gggaggccaa ggtgggtgga tcgcttaagg tcaggagttc gagaccagcc      660
tggccaatat agcgaaaccc catctgtact aaaaacacaa aaattagctg ggtgtggtga      720
cacatgcctg taatcccagg tactcaggag gctaaggcag gagaattgct tgaactggga      780
ggcagaggtg gtgagccaag attgcaccag tgcactccag ccttggtgac agagtgaaac      840
tccatctcaa aaacaaacaa acaaaataca tatacataaa tatatatgca catatatata      900
catatataaa tatatataca catatataaa tctatataca tatatacata tatacacata      960
tataaatcta tatacatata tatacatata taatatattt acatatataa atatatacat     1020
atataaatat acatatataa atacatatat aaatatacat atatataata acatatataa     1080
atatacatat ataaatatat acatatataa atatacatat ataaatatat atacatatat     1140
aaatatataa atatacaagt atatacaaat atatacatat ataaatgtat atacgtatat     1200
acatatatat ataaatatat aaaaaaactt ttggctgggc acctttccaa atctcatggc     1260
acatataagt ctcatggtaa cctcaaataa aaaaacatat aacagataca ccaaaaataa     1320
aaaccaataa attaaatcat gccaccagaa gaaattacct tcactaaaag gaacacagga     1380
aggaaagaaa gaaggaagag aagaccatga aacaaccaga aaacaaacaa caaaacagca     1440
ggagtaattc ctgacttatc aataataatg ctgggtgtaa atggactaaa ctctccaatc     1500
aaaagacata gagtggctga atggacgaaa aaaacaagac tcaataatct gttgcctaca     1560
agaatatact tcacctataa agggacacat agactgaaaa taaaaggaag gaaaaatatt     1620
ctatgcaaat ggaaaccaaa aaaagaacag aactagctac acttatatca gacaaaaatag    1680 atttcaagac aaaaagtaca aaaagagaca aagtaattat ataataataa agcaaaaaga     1740
tataacaatt gtgaatttat atgcgcccaa cactgggaca cccagatata tacagcaaat     1800
attattagaa ctaaggagag agagagatcc ccatacaata atagctggag acttcacccc     1860
gcttttagca ttggacagat catccagaca gaaaatcaac caaaaaattg gacttaatct     1920
ataatataga acaaatgtac ctaattgatg tttacaagac atttcatcca gtagttgcag     1980
aatatgcatt ttttcctcag catatggatc attctcaagg atagaccata tattaggcca     2040
cagaacaagc cattaaaaat tcaaaaaaat tgagccaggc atgatggctt atgcttgtaa     2100
ttacagcact ttggggaggg tgaggtggga ggatgtcttg agtacaggag tttgagacca     2160
gcctgggcaa aatagtgaga ccctgtctct acaaactttt ttttttaatt agccaggcat     2220
agtggtgtgt gcctgtagtc ccagctactt aggaggctga agtgggagga tcacttgagc     2280
ccaagagttc aaggctacgg tgagccatga ttgcaacacc acacaccagc cttggtgaca     2340
gaatgagacc ctgtctcaaa aaaaaaaaaa aaaattgaaa taatataaag catcttctct     2400
ggccacagtg gaacaaaacc agaaatcaac aacaagagga attttgaaaa ctatacaaac     2460
acatgaaaat taaacaatat acttctgaat aaccagtgag tcaatgaaga aattaaaaag     2520
gaaattgaaa aatttattta agcaaatgat aacggaaaca taacctctca aaacccacgg     2580
tatacagcaa aagcagtgct aagaaggaag tttatagcta taagcagcta catcaaaaaa     2640
gtagaaaagc caggcgcagt ggctcatgcc tgtaatccca gcactttggg aggccaaggc     2700
gggcagatcg cctgaggtca ggagttcgag accagcctga ccaacacaga gaaaccttgt     2760
```

```
cgctactaaa aatacaaaat tagctgggca tggtggcaca tgcctgtaat cccagctact      2820
cgggaggctg aggcaggata accgcttgaa cccaggaggt ggaggttgcg gtgagccggg      2880
attgcgccat tggactccag cctgggtaac aagagtgaaa ccctgtctca agaaaaaaaa      2940
aaaagtagaa aaacttaaaa atacaaccta atgatgcacc ttaaagaact agaaaagcaa      3000
gagcaaacta aacctaaaat tggtaaaaga aaagaaataa taaagatcag agcagaaata      3060
aatgaaactg aaagataaca atacaaaaga tcaacaaaat taaaagttgg tttttttgaaa      3120 agataaacaa aattgacaaa cctttgccca gactaagaaa aaaggaaaga agacctaaat      3180
aaataaagtc agagatgaaa aaagagacat tacaactgat accacagaaa ttcaaaggat      3240
cactagaggc tactatgagc aactgtacac taataaattg aaaaacctag aaaaaatagda      3300 taaattccta gatgcataca acctaccaag attgaaccat gaagaaatcc aaagcccaaa      3360
cagaccaata acaataatgg gattaaagcc ataataaaaa gtctcctagc aaagagaagc      3420
ccaggaccca atggcttccc tgctggattt taccaatcat ttaaagaaga atgaattcca      3480
atcctactca aactattctg aaaaatagag gaaagaatac ttccaaactc attctacatg      3540
gccagtatta ccctgattcc aaaaccagac aaaaacacat caaaaacaaa caaacaaaaa      3600
aacagaaaga aagaaaacta caggccaata tccctgatga atactgatac aaaaatcctc      3660
aacaaaacac tagcaaacca aattaaacaa caccttcgaa agatcattca ttgtgatcaa      3720 gtgggatttta ttccagggat ggaaggatgg ttcaacatat gcaaatcaat caatgtgata      3780
catcatccca acaaaatgaa gtacaaaaac tatatgatta tttcactttta tgcagaaaaa      3840 gcatttgata aaattctgca cccttcatga taaaaaccct caaaaaacca ggtatacaag      3900
aaacatacag gccaggcaca gtggctcaca cctgcgatcc cagcactctg ggaggccaag      3960
gtgggatgat tgcttgggcc caggagtttg agactagcct gggcaacaaa atgagacctg      4020
gtctacaaaa aactttttta aaaaattagc caggcatgat ggcatatgcc tgtagtccca      4080
gctagtctgg aggctgaggt gggagaatca cttaagccta ggaggtcgag gctgcagtga      4140
gccatgaaca tgtcactgta ctccagccta gacaacagaa caagaccccca ctgaataaga      4200 agaaggagaa ggagaaggga gaaaggaggg agaagggagg aggaggagaa ggaggaggtg      4260
gaggagaagt ggaagggggaa ggggaaggga aagaggaaga agaagaaaca tatttcaaca      4320
taataaaagc cctatatgac agaccgaggt agtattatga ggaaaaactg aaagcctttc      4380
ctctaagatc tggaaaatga caagggccca ctttcaccac tgtgattcaa catagtacta      4440
gaagtcctag ctagagcaat cagataagag aaagaaataa aaggcatcca aactggaaag      4500
gaagaagtca aattatcctg tttgcagatg atatgatctt atatctggaa aagacttaag      4560
acaccactaa aaaactatta gagctgaaat ttggtacagc aggatacaaa atcaatgtac      4620
aaaaatcagt agtatttcta tattccaaca gcaaacaatc tgaaaagaaa ccaaaaaag      4680 cagctacaaa taaaattaaa cagctaggaa ttaaccaaag aagtgaaaga tctctacaat      4740
gaaaactata aaatattgat aaaagaaatt gagagggca caaaaaaga aaagatattc      4800 catgttcata gattggaaga ataaatactg ttaaatgtc catactaccc aaagcaattt      4860
acaaattcaa tgcaatccct attaaaatac taatgacgtt cttcacagaa atagaagaaa      4920
caattctaag atttgtacag aaccacaaaa gacccagaat agccaaagct atcctgacca      4980
aaaagaacaa aactggaagc atcacattac ctgacttcaa attatactac aaagctatag      5040
taacccaaac tacatggtac tggcataaaa acagatgaga catggaccag aggaacagaa      5100
tagagaatcc agaaacaaat ccatgcatct acagtgaact cattttttgac aaaggtgcca      5160
```

```
agaacatact ttggggaaaa gataatctct tcaataaatg gtgctggagg aactggatat   5220
ccatatgcaa aataacaata ctagaactct gtctctcacc atatacaaaa gcaaatcaaa   5280
atggatgaaa ggcttaaatc taaaacctca aactttgcaa ctactaaaag aaaacaccgg   5340
agaaactctc caggacattg gagtgggcaa agacttcttg agtaattccc tgcaggcaca   5400
ggcaaccaaa gcaaaacag acaaatggga tcatatcaag ttaaaaagct tctgcccagc    5460
aaaggaaaca atcaacaaag agaagagaca acccacagaa tgggagaata tatttgcaaa   5520
ctattcatct aacaaggaat taataaccag tatatataag gagctcaaac tactctataa   5580 gaaaacacc taataagctg attttcaaaa ataagcaaaa gatctgggta gacatttctc     5640
aaaataagtc atacaaatgg caaacaggca tctgaaaatg tgctcaacac cactgatcat   5700
cagagaaatg caaatcaaaa ctactatgag agatcatctc accccagtta aaatggcttt   5760
tattcaaaag acaggcaata acaaatgcca gtgaggatgt ggataaaagg aaaccctgg    5820 acactgttgg tgggaatgga aattgctacc actatggaga acagtttgaa agttcctcaa   5880
aaaactaaaa ataaagctac catacagcaa tcccattgct aggtatatac tccaaaaaag   5940
ggaatcagtg tatcaacaag ctatctccac tcccacattt actgcagcac tgttcatagc   6000
agccaaggtt tggaagcaac ctcagtgtcc atcaacagac gaatggaaaa agaaaatgtg   6060
gtgcacatac acaatggagt actacgcagc cataaaaaag aatgagatcc tgtcagttgc   6120
aacagcatgg ggggcactgg tcagtatgtt aagtgaaata agccaggcac agaaagacaa   6180
acttttcatg ttctcccctta cttgtgggag caaaaattaa acaattgac atagaaatag    6240 aggagaatgg tggttctaga ggggtggggg acagggtgac tagagtcaac aataatttat   6300
tgtatgtttt aaaataacta aaagagtata attggggttgt ttgtaacaca agaaaggat     6360 aaatgcttga aggtgacaga tacccccattt accctgatgt gattattaca cattgtatgc   6420
ctgtatcaaa atatctcatg tatgctatag atataaaccc tactatatta aaaattaaaa   6480
ttttaatggc caggcacggt ggctcatgtc cataatccca gcactttggg aggccgaggc   6540
ggtggatcac ctgaggtcag gagtttgaaa ccagtctggc caccatgatg aaaccctgtc   6600
tctactaaag atacaaaaat tagccaggcg tggtggcaca tacctgtagt cccaactact   6660
caggaggctg agacaggaga attgcttgaa cctgggaggc ggaggttgca gtgagccgag   6720
atcatgccac tgcactgcag cctgggtgac agagcaagac tccatctcaa aacaaaaaca   6780 aaaaaagaa gattaaaatt gtaattttta tgtaccgtat aaatatatac tctactatat    6840
tagaagttaa aaattaaaac aattataaaa ggtaattaac cacttaatct aaaataagaa   6900
caatgtatgt ggggtttcta gcttctgaag aagtaaaagt tatggccacg atggcagaaa   6960
tgtgaggagg aacagtggaa agttactgtt gttagacgct catactctct gtaagtgact   7020
taattttaac caaagacagg ctgggagaag ttaaagaggc attctataag ccctaaaaca   7080
actgctaata atggtgaaag gtaatctcta ttaattacca ataattacag atatctctaa   7140
aatcgagctg cagaattggc acgtctgatc acaccgtcct ctcattcacg gtgcttttt    7200 tcttgtgtgc ttggagattt tcgattgtgt gttcgtgttt ggttaaactt aatctgtatg   7260
aatcctgaaa cgaaaaatgg tggtgatttc ctccagaaga attagagtac ctggcaggaa   7320
gcaggtggct ctgtggacct gagccacttc aatcttcaag ggtctctggc caagacccag   7380
gtgcaaggca gaggcctgat gacccgagga caggaaagct cggatgggaa ggggcgatga   7440
gaagcctgcc tcgttggtga gcagcgcatg aagtgccctt atttacgctt tgcaaagatt   7500
gctctggata ccatctggaa aaggcggcca gcgggaatgc aaggagtcag aagcctcctg   7560
```

```
ctcaaaccca ggccagcagc tatggcgccc acccgggcgt gtgccagagg gagaggagtc   7620
aaggcacctc gaagtatggc ttaaatcttt ttttcacctg aagcagtgac caaggtgtat   7680
tctgagggaa gcttgagtta ggtgccttct ttaaaacaga aagtcatgga agcacccttc   7740
tcaagggaaa accagacgcc cgctctgcgg tcatttacct ctttcctctc tccctctctt   7800
gccctcgcgg tttctgatcg ggacagagtg accccgtgg agcttctccg agcccgtgct    7860
gaggaccctc ttgcaaaggg ctccacagac ccccgccctg gagagaggag tctgagcctg   7920
gcttaataac aaactgggat gtggctgggg gcggacagcg acggcgggat tcaaagactt   7980
aattccatga gtaaattcaa cctttccaca tccgaatgga tttggatttt atcttaatat   8040
tttcttaaat ttcatcaaat aacattcagg agtgcagaaa tccaaaggcg taaaacagga   8100
actgagctat gtttgccaag gtccaaggac ttaataacca tgttcagagg gattttcgc    8160 cctaagtact ttttattggt tttcataagg tggcttaggg tgcaagggaa agtacacgag   8220
gagaggactg ggcggcaggg ctatgagcac ggcaaggcca ccggggagag agtccccggc   8280
ctgggaggct gacagcagga ccactgaccg tcctccctgg gagctgccac attgggcaac   8340
gcgaaggcgg ccacgctgcg tgtgactcag gaccccatac cggcttcctg ggcccaccca   8400
cactaaccca ggaagtcacg gagctctgaa cccgtggaaa cgaacatgac ccttgcctgc   8460
ctgcttccct gggtgggtca agggtaatga agtggtgtgc aggaaatggc catgtaaatt   8520
acacgactct gctgatgggg accgttcctt ccatcattat tcatcttcac ccccaaggac   8580
tgaatgattc cagcaacttc ttcgggtgtg acaagccatg acaacactca gtacaaacac   8640
cactctttta ctaggcccac agagcacggc ccacacccct gatatattaa gagtccagga   8700
gagatgaggc tgctttcagc caccaggctg gggtgacaac agcggctgaa cagtctgttc   8760
ctctagacta gtagaccctg gcaggcactc ccccagattc tagggcctgg ttgctgcttc   8820
ccgagggcgc catctgccct ggagactcag cctggggtgc cacactgagg ccagccctgt   8880
ctccacaccc tccgcctcca ggcctcagct tctccagcag cttcctaaac cctgggtggg   8940
ccgtgttcca gcgctactgt ctcacctgtc ccactgtgtc ttgtctcagc gacgtagctc   9000
gcacggttcc tcctcacatg gggtgtctgt ctccttcccc aacactcaca tgcgttgaag   9060
ggaggagatt ctgcgcctcc cagactggcc cctctgagcc tgaacctggc tcgtggcccc   9120
cgatgcaggt tcctggcgtc cggctgcacg ctgacctcca tttccaggcg ctccccgtct   9180
cctgtcatct gccggggcct gccgtgtgt tcttctgttt ctgtgctcct ttccacgtcc     9240
agctgcgtgt gtctctgtcc gctagggtct cggggttttt ataggcatag gacggggggcg   9300 tggtgggcca gggcgctctt gggaaatgca acatttgggt gtgaaagtag gagtgcctgt   9360
cctcacctag gtccacgggc acaggcctgg ggatggagcc cccgcagggg acccgcccctt   9420 ctctgcccag cacttttctg cccccctccc tctggaacac agagtggcag tttccacaag   9480
cactaagcat cctcttccca aaagacccag cattggcacc cctggacatt tgccccacag   9540
ccctgggaat tcacgtgact acgcacatca tgtacacact cccgtccacg accgaccccc   9600
gctgttttat tttaatagct acaaagcagg gaaatccctg ctaaaatgtc ctttaacaaa   9660
ctggttaaac aaacgggtcc atccgcacgg tggacagttc ctcacagtga agaggaacat   9720
gccgtttata aagcctgcag gcatctcaag ggaattacgc tgagtcaaaa ctgccacctc   9780
catgggatac gtacgcaaca tgctcaaaaa gaaagaattt caccccatgg caggggagtg   9840 gttgggggggt taaggacggt gggggcagca gctgggggct actgcacgca ccttttacta   9900
aagccagttt cctggttctg atggtattgg ctcagttatg ggagactaac cataggggag   9960
```

```
tggggatggg ggaacccgga ggctgtgcca tctttgccat gcccgagtgt cctgggcagg    10020
ataatgctct agagatgccc acgtcctgat tcccccaaac ctgtggacag aacccgcccg    10080
gccccagggc ctttgcaggt gtgatctccg tgaggaccct gaggtctggg atccttcggg    10140
actacctgca ggcccgaaaa gtaatccagg ggttctggga agaggcgggc aggagggtca    10200
gagggggggca gcctcaggac gatggaggca gtcagtctga ggctgaaaag ggagggaggg    10260
cctcgagccc aggcctgcaa gcgcctccag aagctggaaa aagcggggaa gggaccctcc    10320
acggagcctg cagcaggaag gcacggctgg cccttagccc accagggccc atcgtggacc    10380
tccggcctcc gtgccatagg agggcactcg cgctgcccct ctagcatgaa gtgtgtgggg    10440
atttgcagaa gcaacaggaa acccatgcac tgtgaatcta ggattatttc aaaacaaagg    10500
tttacagaaa catccaagga cagggctgaa gtgcctccgg gcaagggcag ggcaggcacg    10560
agtgattta tttagctatt ttattttatt tacttactttt ctgagacaga gttatgctct    10620
tgttgcccag gctggagtgc agcggcatga tcttggctca ctgcaacctc cgtctcctgg    10680
gttcaagcaa ttctcgtgcc tcagcctccc aagtagctgg gatttcaggc gtgcaccacc    10740
acacccggct aattttgtat ttttagtaga gatgggcttt caccatgttg gtcaggctga    10800
tctcaaaatc ctgacctcag gtgatccgcc cacctcagcc tcccaaagtg ctgggattac    10860
aggcatgagc cactgcacct ggcctattta accatttaa aacttccctg gctcaagtc     10920
acacccactg gtaaggagtt catggagttc aatttccct ttactcagga gttaccctcc     10980
tttgatattt tctgtaattc ttcgtagact ggggatacac cgtctcttga catattcaca    11040
gtttctgtga ccacctgtta tcccatggga cccactgcag gggcagctgg gaggctgcag    11100
gcttcaggtc ccagtggggt tgccatctgc cagtagaaac ctgatgtaga atcagggcgc    11160
gagtgtggac actgtcctga atctcaatgt ctcagtgtgt gctgaaacat gtagaaatta    11220
aagtccatcc ctcctactct actgggattg agccccttcc ctatccccc ccaggggcag     11280
aggagttcct ctcactcctg tggaggaagg aatgatactt tgttattttt cactgctggt    11340
actgaatcca ctgtttcatt tgttggtttg tttgttttgt tttgagaggc ggtttcactc    11400
ttgttgctca ggctggaggg agtgcaatgg cgcgatcttg gcttactgca gcctctgcct    11460
cccaggttca agtgattctc ctgcttccgc ctcccatttg gctgggatta caggcacccg    11520
ccaccatgcc cagctaattt tttgtatttt tagtagagac ggggtgggg gtggggttca     11580
ccatgttggc caggctggtc tcgaacttct gacctcagat gatccacctg cctctgcctc    11640
ctaaagtgct gggattacag gtgtgagcca ccatgcccag ctcagaattt actctgttta    11700
gaaacatctg ggtctgaggt aggaagctca ccccactcaa gtgttgtggt gttttaagcc    11760
aatgatagaa ttttttttatt gttgttagaa cactcttgat gttttacact gtgatgacta    11820
agacatcatc agcttttcaa agacacacta actgcaccca taatactggg gtgtcttctg    11880
ggtatcagcg atcttcattg aatgccggga ggcgtttcct cgccatgcac atggtgttaa    11940
ttactccagc ataatcttct gcttccattt cttctcttcc ctcttttaaa attgtgtttt    12000
ctatgttggc ttctctgcag agaaccagtg taagctacaa cttaactttt gttgaacaa     12060
attttccaaa ccgccccttt gccctagtgg cagagacaat tcacaaacac agcccttaa     12120
aaaggcttag ggatcactaa ggggattct agaagagcga cccgtaatcc taagtattta    12180
caagacgagg ctaacctcca gcgagcgtga cagcccaggg agggtgcgag gcctgttcaa    12240
atgctagctc cataaataaa gcaatttcct ccggcagttt ctgaaagtag gaaaggttac    12300
atttaaggtt gcgtttgtta gcatttcagt gtttgccgac ctcagctaca gcatccctgc    12360
```

```
aaggcctcgg gagacccaga agtttctcgc cccttagatc caaacttgag caacccggag   12420
tctggattcc tgggaagtcc tcagctgtcc tgcggttgtg ccggggcccc aggtctggag   12480
gggaccagtg gccgtgtggc ttctactgct gggctggaag tcgggcctcc tagctctgca   12540
gtccgaggct tggagccagg tgcctggacc ccgaggctgc cctccaccct gtgcgggcgg   12600
gatgtgacca gatgttggcc tcatctgcca gacagagtgc cggggcccag ggtcaaggcc   12660
gttgtggctg gtgtgaggcg cccggtgcgc ggccagcagg agcgcctggc tccatttccc   12720
acccttctc gacgggaccg ccccggtggg tgattaacag atttggggtg gtttgctcat    12780
ggtggggacc cctcgccgcc tgagaacctg caaagagaaa tgacgggcct gtgtcaagga   12840
gcccaagtcg cggggaagtg ttgcaggag gcactccggg aggtcccgcg tgcccgtcca    12900
gggagcaatg cgtcctcggg ttcgtcccca gccgcgtcta cgcgcctccg tcctcccctt   12960
cacgtccggc attcgtggtg cccggagccc gacgccccgc gtccggacct ggaggcagcc   13020
ctgggtctcc ggatcaggcc agcggccaaa ggtcgccgc acgcacctgt tcccagggcc    13080
tccacatcat ggcccctccc tcgggttacc ccacagccta ggccgattcg acctctctcc   13140
gctgggcc tcgctggcgt ccctgcaccc tgggagcgcg agcggcgcgc gggcggggaa     13200
gcgcggccca gaccccgggg tccgcccgga gcagctgcgc tgtcggggcc aggccgggct   13260
cccagtggat tcgcgggcac agacgcccag gaccgcgctt ccacgtggc ggagggactg    13320
gggacccggg cacccgtcct gccccttcac cttccagctc cgcctcctcc gcgcggaccc   13380
cgccccgtcc cgacccctcc cgggtccccg gcccagcccc ctccgggccc tcccagcccc   13440
tccccttcct ttccgcggcc ccgccctctc ctcgcggcgc gagtttcagg cagcgctgcg   13500
tcctgctgcg cacgtgggaa gccctggccc cggccacccc cgcgatgccg cgcgctcccc   13560
gctgccgagc cgtgcgctcc ctgctgcgca gccactaccg cgaggtgctg ccgctggcca   13620
cgttcgtgcg gcgcctgggg ccccagggct ggcggctggt gcagcgcggg gaccggcgg   13680
cttttccgcgc gctggtggcc cagtgcctgg tgtgcgtgcc ctgggacgca cggccgcccc   13740
ccgccgcccc ctccttccgc caggtgggcc tccccggggt cggcgtccgg ctggggttga   13800
gggcggccgg ggggaaccag cgacatgcgg agagcagcgc aggcgactca gggcgcttcc   13860
cccgcaggtg tcctgcctga aggagctggt ggcccgagtg ctgcagaggc tgtgcgagcg   13920
cggcgcgaag aacgtgctgg ccttcggctt cgcgctgctg acggggcccc gcgggggccc   13980
ccccgaggcc ttcaccacca gcgtgcgcag ctacctgccc aacacggtga ccgacgcact   14040
gcggggagc ggggcgtggg ggctgctgct gcgccgcgtg ggcgacgacg tgctggttca    14100
cctgctggca cgctgcgcgc tctttgtgct ggtggctccc agctgcgcct accaggtgtg   14160
cgggccgccg ctgtaccagc tcggcgctgc cactcaggcc cggcccccgc cacacgctag   14220
tggaccccga aggcgtctgg gatgcgaacg ggcctggaac catagcgtca gggaggccgg   14280
ggtcccctg ggcctgccag ccccgggtgc gaggaggcgc gggggcagtg ccagccgaag    14340
tctgccgttg cccaagaggc ccaggcgtgg cgctgcccct gagccggagc ggacgcccgt   14400
tgggcagggg tcctgggccc acccgggcag gacgcgtgga ccgagtgacc gtggtttctg   14460
tgtggtgtca cctgccagac ccgccgaaga agccacctct ttggagggtg cgctctctgg   14520
cacgcgccac tccacccat ccgtgggccg ccagcaccac gcgggccccc catccacatc    14580
gcggccacca cgtccctggg acacgccttg tccccggtg tacgccgaga ccaagcactt    14640
cctctactcc tcaggcgaca aggagcagct gcggccctcc ttcctactca gctctctgag   14700
gcccagcctg actggcgctc ggaggctcgt ggagaccatc tttctggtt ccaggccctg    14760
```

-continued

```
gatgccaggg actccccgca ggttgccccg cctgccccag cgctactggc aaatgcggcc      14820
cctgtttctg gagctgcttg ggaaccacgc gcagtgcccc tacggggtgc tcctcaagac      14880
gcactgcccg ctgcgagctg cggtcacccc agcagccggt gtctgtgccc gggagaagcc      14940
ccagggctct gtggcggccc ccgaggagga ggacacagac ccccgtcgcc tggtgcagct      15000
gctccgccag cacagcagcc cctggcaggt gtacggcttc gtgcgggcct gcctgcgccg      15060
gctggtgccc ccaggcctct ggggctccag gcacaacgaa cgccgcttcc tcaggaacac      15120
caagaagttc atctccctgg ggaagcatgc caagctctcg ctgcaggagc tgacgtggaa      15180
gatgagcgtg cgggactgcg cttggctgcg caggagcccag gtgaggagg tggtggccgt      15240 cgagggccca ggccccagag ctgaatgcag tagggctca gaaaagggg caggcagagc       15300 cctggtcctc ctgtctccat cgtcacgtgg gcacacgtgg cttttcgctc aggacgtcga      15360
gtggacacgg tgatcgagtc gactccctt agtgagggtt aattgagctc gcggccgc        15418
```

<210> SEQ ID NO 2
<211> LENGTH: 7498
<212> TYPE: DNA
<213> ORGANISM: Mus sp.
<220> FEATURE:
<223> OTHER INFORMATION: Mouse TERT promoter

<400> SEQUENCE: 2

```
aagcttccag caaaccagtt agagctgagt tgatgctctg aagaagagaa aatgtagaga        60
cggtactgaa caaataatgt ctgggcaaac ctcagacatg aaaatggaag acgtggaaat       120
ccagagaact ctgagggaaa ataaaacaca actccaggtc atcacgggac tcatcaaact       180
gctgaggtgc agccacagag aaaaatctta aaatagccta gaacgatgca tgacacataa       240
agcacagaga agacgaagct gagtctgtct tgtaggaaca acttgagaag acctaaacca       300
ctgcaatgag tgcattctgc taacttagaa tttgctaccc agttcagatc caaaaagggt       360
ttcacaaagt tcaacacaaa acagtagcag gagtggctaa ggggacaca ctgataggaa         420 ttcagagaag tagggaatgc tcatatgggg acattacaaa atgtactttc atgttgctta       480
aatcatttta attgtcaacc acatcaagct aaataatgct ttgaggttca taacatttgg       540
agattatgtc tacactagca gagaaggcac caataacatc ccaattgcta gattctcata       600
gaatcatgag tcacaatggc agagacaggt tctgagagtg tgtccttgtt gtaaacagta       660
tgctctacaa actaagttgg ctgcaatatc actaggcagt gttgtcccat aagcaaacta       720
tcacatatgt ggtccagtga tgaccaaagc atctttttagc attttgcaaa tgaagctcaa      780
atcgaatatg actaagctca tgcagtacaa atcaaaggta cactgggata gtttaaaaga      840
tacatacttg tactggttag ttttgtgtca gcttgacaca gctggagtta tcacagagaa       900
aagagcttca gttgaggaaa ttcctccatg agatccagct ataggggcatt ttctcaatta      960 gtgatcaagg ggggaaggcc ccttgtgggt gggaccatct ctgggctggt agtcttggtt     1020
ctataagaga gcaggctgag caagccagga gaagcaagcc agtaaagaac atccctccat     1080
ggcttctgca tcagctcctg ctccctgacc tgcttgagtt ccagttctaa cttctttcag     1140
tgatgaacag caatgtggaa atgaaagctg ataaaccct ttcctcccca ttttgcttct      1200
tggtcatgat gtttgtgcag gaatagaaac cctgactaag acaatactat aaaccctaaa     1260
agttgtaaac caaacacatg tgtttccatt aagccatcgt agaacaataa gtactcaacc     1320
ccaagtcaca taactataat cccagccttt gaaaaccggg atcaggaatt caaggctagc     1380
ctcatctata tgtaagatta agcctgtttt gggctgcatg agactttgtt tcaaaaaaaa     1440
```

-continued

```
aaaaaaaaaa gcaaacaggc aaaaacaaac acaagacaag acagatgtaa aatgaaggag    1500
gggtagatgg gtcaagtaga aaatagcata ggaaacgagt caagtataga agaggtggta    1560
gtaaccagat catgcagaag gactcaaggc catctcctca cagtggctta ggtaggcctt    1620
cctctgctct tgagcagggg cagagttgcc gctttaagga ggggatcagt caccttaag     1680 aactgaaaag ctgaacagtc ttctcaagtc agaagccagt ggcttcatct tacacctctc    1740
ttccttccct tgctactcat attggatctg atgatttgcc caacttggaa gaaacatctc    1800
ttctgaaggg tttcacagac accccatctt tccgagaaag gaccgcatag gctggccatc    1860
cctgtgctta caaaggaat aattaagaaa cttaattcca taagcaaata caaccttcc     1920 aagccccaag tggatgattt tatcttactg tttttttata tctcatcaaa taacttccaa    1980
gggctcaaaa atccaaagat gtaaaaaagg aactgagctc tgtttgccaa gcatgagga    2040 ttaaataatg acattcaaag gattttttgt gccctaagta cttttattg gttttcatag     2100 atggtttaat gtgcaagatg aagcaaacag agatgggagt ggtatcagca tggattaagg    2160
tggcagttgt gagggaggg tactgagaga acaggacaag gtaacctatc taaggagagg    2220
ccaagttggc aagtgccagg gacttctaag cccagaacta gtacacattc cttaggtgct    2280
gtttgggaag tcagggagtc accagccttg ggatctataa aagtgcatgg tggcattcac    2340
tcacatactt cctgagctgt tcgatgttga tgaagtcgtg ggtatgagac tgttgtgtca    2400
gtgacaaact atgtaaatga gaatgattgt ttccatcttg accactaaga cgtaaaccgg    2460
ttccagtgat ctccaaacat ggcaagctac agcagagcag cagccccatc cagagccttg    2520
ccctggttct gaatggggga gaatccagtg ggagtcggtt gctgccagca tgttggggta    2580
gaaggctgga gcatgacagg tccccgagga tttcctgctt cctatatggg tagggatact    2640
tgaggtcctc tcttctacct ccttccctgc agggtttata acctctacca ctgtctgtct    2700
ctgggatagc tcctagggtg cagccccctcc ccaaaaaggc ctctccctgg cctcatgtct    2760
ctaagaacag ctttctaaag caggcctgtt acacaaaggc tcccttttcc tggcttcatc    2820
gttgctggta gacaacttcc actcgttttc cacttcagtt tcttctactc tgttgttatt    2880
tgattctgat gcttgaaccc agggttgtgt agtcagcaag tgctaccccc tccctcctct    2940 tctttgttt tttgaggcag ggtctcattt tgcccaagtg gacctaaatt tcagcatgta    3000
gctggcctgg ttttgaatgc cttctcatcc tgcctctact tcccaagagt agcttacaag    3060
tgtgcaccac catgccccgc gatattctta ttttttgagac tgttttctat gctggtttct    3120
ttggggaact acactaaggt agcttacaag tgtgcaccac catgccccgc gatattctta    3180 ttttttgagac tgttttctat gctggtttct ttggggaact acactaaggt agcttcattg    3240
ttggcataaa tttctcagtt caggcccata tctcctaagt agcagaacta agcaaatctc    3300
aaacaaaccc ctcaaaaaga ctgatgtcca ctaaacggac ttctaaaata gctcctgtaa    3360
tcctgagcat ttacaaggcg gcagacctcc tataaggag taaatatgaa aacgcgcctg     3420
ttcaaatgct aggtcggtgg atagaagcaa tttcctcaga agctgaagg caccaaaggt     3480 tatatttgtt agcatttcag tgtttgccaa actcagctac agtagagatc acagattccc    3540
tatttcccag agattcaaaa ttcagcagcc cctctctaac tatggctcag agtcgtgtca    3600
ttacatatgc cccaacaaca accccacacc ctatcctacc cccgcctcac acgtgcaagt    3660
actatcacag ttgccaacct agcagagctg ccatcctaag gtcgaggtcg ccgctttggc    3720
tgtgtgcaca gcaagcgcc ctcacccaat ggccctggcc ttgctatggg tgcgtgagtt     3780
gagatgatgc tctggactct gaggtgaagg ccactggaac agtgaaaaaa gctaacgcag    3840
```

```
ggcttttacc tagtcccctt cctttggtgg tgggtgttta cggaacatat ttgggatctg   3900
agtgtatggt cgcaccacaa taaagcctta acctatatag tagaatttca gctgtaatca   3960
ttaagaactg agattgccac cacccacctc actgtctgtg tcaaccacag caggctggag   4020
cagtcagctc aggaacaggc aaaaccttag gtccctccgc ctacctaacc ttcaatacat   4080
caaggatagg cttctttgct tgcccaaacc tcgccccagt ctagaccacc tgggattcc    4140 cagctcaggg cgaaaaggaa gcccgagaag cattctgtag agggaaatcc tgcatgagtg   4200
cgcccccttt cgttactcca acacatccag caaccactga acttggccgg ggaacacacc   4260
tggtcctcat gcaccagcat tgtgaccatc aacggaaaag tactattgct gcgacccgc    4320 cccttccgct acaacgcttg gtccgcctga atcccgcccc ttcctccgtt cccagcctca   4380 tcttttcgt cgtggactct cagtggcctg ggtcctggct gttttctaag cacacccttg    4440
catcttggtt cccgcacgtg ggaggcccat cccggccttg agcacaatga cccgcgctcc   4500
tcgttgcccc gcggtgcgct ctctgctgcg cagccgatac cgggaggtgt ggccgctggc   4560
aacctttgtg cggcgcctgg ggcccgaggg caggcggctt gtgcaacccg ggacccgaa    4620 gatctaccgc actttggttg cccaatgcct agtgtgcatg cactgggct cacagcctcc    4680 acctgccgac ctttccttcc accaggtggg cctccaggcg ggatccccat gggtcagggg   4740
cggaaagccg ggaggacgtg ggatagtgcg tctagctcat gtgtcaagac cctcttctcc   4800
ttaccaggtg tcatccctga aagagctggt ggccagggtt gtgcagagac tctgcgagcg   4860
caacgagaga aacgtgctgg cttttggctt tgagctgctt aacgaggcca gaggcgggcc   4920
tcccatggcc ttcactagta gcgtgcgtag ctacttgccc aacactgtta ttgagaccct   4980
gcgtgtcagt ggtgcatgga tgctactgtt gagccgagtg ggcgacgacc tgctggtcta   5040
cctgctggca cactgtgctc tttatcttct ggtgcccccc agctgtgcct accaggtgtg   5100
tgggtctccc ctgtaccaaa tttgtgccac cacggatatc tggccctctg tgtccgctag   5160
ttacaggccc acccgacccg tgggcaggaa tttcactaac cttaggttct tacaacagat   5220
caagagcagt agtcgccagg aagcaccgaa accccctggcc ttgccatctc gaggtacaaa   5280
gaggcatctg agtctcacca gtacaagtgt gccttcagct aagaaggcca gatgctatcc   5340
tgtcccgaga gtggaggagg gaccccacag gcaggtgcta ccaacccat caggcaaatc    5400 atgggtgcca agtcctgctc ggtcccccga ggtgcctact gcagagaaag atttgtcttc   5460
taaaggaaag gtgtctgacc tgagtctctc tgggtcggtg tgctgtaaac acaagcccag   5520
ctccacatct ctgctgtcac cacccgcca aaatgccttt cagctcaggc catttattga    5580
gaccagacat ttcctttact ccaggggaga tggccaagag cgtctaaacc cctcattcct   5640
actcagcaac ctccagccta acttgactgg ggccaggaga ctggtggaga tcatctttct   5700
gggctcaagg cctaggacat caggaccact ctgcaggaca caccgtctat cgcgtcgata   5760
ctggcagatg cggcccctgt tccaacagct gctggtgaac catgcagagt gccaatatgt   5820
cagactcctc aggtcacatt gcaggtttcg aacagcaaac caacaggtga cagatgcctt   5880
gaacaccagc ccaccgcacc tcatggattt gctccgcctg cacagcagtc cctggcaggt   5940
atatggtttt cttcgggcct gtctctgcaa ggtggtgtct gctagtctct ggggtaccag   6000
gcacaatgag cgccgcttct ttaagaactt aaagaagttc atctcgttgg ggaaatacgg   6060
caagctatca ctgcaggaac tgatgtggaa gatgaaagta gaggattgcc actggctccg   6120
cagcagcccg ggtgagcatg gctggtctcc agctgaatgc attaggggcc cagaaaaggg   6180
agacaatggg tggcagtaac ccaggtcccc agtggtgtgg tggctttatg cagtccgtgg   6240
```

```
ttgGatgagt tccatcttat ggtctctgac tccaagctcc ctccagctcg ccttgcacaa    6300
actaagattc ttgtccaagc cctgggcagg ttctcagggc tggggacatt gtggtgaaca    6360
gataagcaga cggggagcat ggtggatagg agttctggca cagtgcacca gagagagtct    6420
ggaagcgcta gtgagagcta atgtaagggc ccgtggttcg ccaaagaatg ataaccccgg    6480
actcaaatag tatgccaaag caaggagcat tcattctgc agaaatcaag catgcaggtg     6540
gggggggggg gttgctctca ttccaagatg gagagacaac caagtataga ttttaagggg    6600
atcgggggcc tttatcttac tccatctcta ggggcattcc attactgggg catgggggttg   6660 gaggttggaa actgttaatg gggaggtctg gaaacttgct gccccattgt ccttgcttca    6720
ggctaggtag ctgagtagct tctaatggca ggatagtttc tgactagctg tctaaagtct    6780
ggggtgtttg ttttttttgtt ttttctagta acttacttgc ctgaacttgc tcagttttta   6840
ggcctggtct cctggactgc caatttgaag cctattaagg agtcagcctg tctcactact    6900
ccaggttatc tataatcccc ctgtagaacg gtacctcact gataacaatg acagaccaac    6960
ataggaaccc actatccttg tggtgcatga gtttcaaagg ttcttctggt cctcccagtg    7020
tgcagatcca tgcttaagct atggtcctcc cagtgtgcag atccgtgctt aagctatggt    7080
cttgcagctg ctcgatctac aaagggtagg gtgaacgaag gaaagataaa tgaaaaaaaa    7140
aaaactgttt cctacagtga agatcgctgc cccatcttag ctatgagaag ggactgggga    7200
gtggagcctg gtgcataaaa gaggattgtg ttacttggaa ggctgcagag cctggactcc    7260
tgtgccctcc ttgcctggtt ttctgggttt aatgttgagg ttggccctct gtagtcacta    7320 cctgaccct tcccttcag ccaaccctcc ggttacaccc tgtgcatgta tggaaggggc      7380
caaacgccct atcctgctct cccttcccca aaattcttag gatattaaca acttatgggg    7440
aaaagatggt agagctatgt ttacccacca tgtacttggg aagctccgaa gtaagctt     7498
```

<210> SEQ ID NO 3
<211> LENGTH: 144
<212> TYPE: DNA
<213> ORGANISM: Artificial Sequence
<220> FEATURE:
<223> OTHER INFORMATION: NCO1 fragment containing hTERT upstream
      sequences and the first intron of hTERT from lambdaGPhi5
      into the NCO1 site of a pBBS167 (variant of pUC
      cloning vector with MCS)

<400> SEQUENCE: 3

```
atgaccatga ttacgaattc gagctcggta cccggggatc ctctagagtc gacctgcagg     60
catgcccatg gcaggcctcg cgcgcgagat ctcgggccca atcgatgccg cggcgatatc    120
gctcgaggaa gcttggcact ggcc                                            144
```

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: RA94

<400> SEQUENCE: 4

```
cccggccacc cccgcgaatt cgcgcgctcc ccgctgc                              37
```

<210> SEQ ID NO 5
<211> LENGTH: 65
<212> TYPE: DNA
<213> ORGANISM: Artificial Sequence -continued

```
<220> FEATURE:
<223> OTHER INFORMATION: Description of Artificial Sequence: RA91

<400> SEQUENCE: 5
ttgtactgag agtgcaccat atgcggtgtg catgctacgt aagaggttcc aactttcacc    60
ataat                                                                65

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: RA96

<400> SEQUENCE: 6
aattgcgaag cttacg                                                    16

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: RA97

<400> SEQUENCE: 7
aattcgtaag cttcgc                                                    16

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence: oligo RA101

<400> SEQUENCE: 8
taggtaccga gctcttacgc gtgctagccc cacgtggcgg agggactggg gacccgggca    60

<210> SEQ ID NO 9
<211> LENGTH: 58
<212> TYPE: DNA
<213> ORGANISM: Artificial Sequence
<220> FEATURE:
<223> OTHER INFORMATION: Description of Artificial Sequence: oligo RA100

<400> SEQUENCE: 9
taggtaccga gctcttacgc gtgctagccc ctcgctggcg tccctgcacc ctgggagc      58

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: RA107

<400> SEQUENCE: 10
cgtcctgctg cgcactcagg aagccctggc ccc                                 33

<210> SEQ ID NO 11
<211> LENGTH: 6
<212> TYPE: DNA
<213> ORGANISM: Artificial Sequence
<220> FEATURE:
<223> OTHER INFORMATION: Description of Artificial Sequence: 'B' class
      E-Box just proximal to the hTERT initiating Met in
      pGRN262
```

```
<400> SEQUENCE: 11 cacgtg                                                                     6

<210> SEQ ID NO 12
<211> LENGTH: 6
<212> TYPE: DNA
<213> ORGANISM: Artificial Sequence
<220> FEATURE:
<223> OTHER INFORMATION: Description of Artificial Sequence: changed 'B'
      class E-Box just proximal to the hTERT initiating
      Met in pGRN262

<400> SEQUENCE: 12 cactca                                                                     6

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: COD1941

<400> SEQUENCE: 13
gatgaatgct catgattccg tatgg                                               25

<210> SEQ ID NO 14
<211> LENGTH: 57
<212> TYPE: DNA
<213> ORGANISM: Artificial Sequence
<220> FEATURE:
<223> OTHER INFORMATION: Description of Artificial Sequence: COD2866

<400> SEQUENCE: 14
cagcatcttt tactttcacc agcgtttctg ggtgcgcaaa aacaggaagg caaaatg           57

<210> SEQ ID NO 15
<211> LENGTH: 58
<212> TYPE: DNA
<213> ORGANISM: Artificial Sequence
<220> FEATURE:
<223> OTHER INFORMATION: Description of Artificial Sequence: RA104

<400> SEQUENCE: 15
taggtaccga gctcttacgc gtgctagccc ctcccagccc ctccccttcc tttccgcg          58

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: RA122

<400> SEQUENCE: 16
gaccgcgctt cccactcagc ggagggactg ggg                                     33

<210> SEQ ID NO 17
<211> LENGTH: 298
<212> TYPE: DNA
<213> ORGANISM: Homo sapiens
<220> FEATURE:
<223> OTHER INFORMATION: Human TERT promoter

<400> SEQUENCE: 17
caggccgggc tcccagtgga ttcgcgggca cagacgccca ggaccgcgct tcccacgtgg         60
cggagggact ggggacccgg gcacccgtcc tgccccttca ccttccagct ccgcctcctc        120
```

```
cgcgcggacc ccgccccgtc ccgacccctc ccgggtcccc ggcccagccc cctccgggcc    180
ctcccagccc ctccccttcc tttccgcggc cccgccctct cctcgcggcg cgagtttcag    240
gcagcgctgc gtcctgctgc gcacgtggga agccctggcc ccggccaccc ccgcgatg     298
```

```
<210> SEQ ID NO 18
<211> LENGTH: 262
<212> TYPE: DNA
<213> ORGANISM: Mus sp.
<220> FEATURE:
<223> OTHER INFORMATION: Mouse TERT promoter

<400> SEQUENCE: 18
```

```
cagcaaccac tgaacttggc cggggaacac acctggtcct catgcaccag cattgtgacc    60
atcaacggaa aagtactatt gctgcgaccc cgccccttcc gctacaacgc ttggtccgcc    120
tgaatcccgc cccttcctcc gttcccagcc tcatctttt cgtcgtggac tctcagtggc     180
ctgggtcctg gctgttttct aagcacaccc ttgcatcttg gttcccgcac gtgggaggcc    240
catcccggcc ttgagcacaa tg                                             262
```

```
<210> SEQ ID NO 19
<211> LENGTH: 77
<212> TYPE: DNA
<213> ORGANISM: Homo sapiens
<220> FEATURE:
<223> OTHER INFORMATION: Human TERT promoter

<400> SEQUENCE: 19
```

```
ctcgcggcgc gagtttcagg cagcgctgcg tcctgctgcg cacgtgggaa gccctggccc    60
cggccacccc cgcgatg                                                   77
```

```
<210> SEQ ID NO 20
<211> LENGTH: 89
<212> TYPE: DNA
<213> ORGANISM: Artificial Sequence
<220> FEATURE:
<223> OTHER INFORMATION: Description of Artificial Sequence: E-box
      reporter construct

<400> SEQUENCE: 20
```

```
ctcgcggcgc gagtttcagg cagcgctgcg tcctgctgcg cacgtgggaa gccctggccc    60
cggccacccc cgcgaattcg cccaccatg                                      89
```

```
<210> SEQ ID NO 21
<211> LENGTH: 56
<212> TYPE: DNA
<213> ORGANISM: Artificial Sequence
<220> FEATURE:
<223> OTHER INFORMATION: Description of Artificial Sequence: E-box
      reporter construct (with portion deleted)

<400> SEQUENCE: 21
```

```
ctcgcggcgc gagtttcagg cagcgctgcg tcctgctgcc gaattcgccc accatg        56
```

```
<210> SEQ ID NO 22
<211> LENGTH: 497
<212> TYPE: DNA
<213> ORGANISM: Homo sapiens
<220> FEATURE:
<223> OTHER INFORMATION: Human TERT promoter
```

```
<400> SEQUENCE: 22
actccagcat aatcttctgc ttccatttct tctcttccct cttttaaaat tgtgttttct        60
atgttggctt ctctgcagag aaccagtgta agctacaact taacttttgt tggaacaaat       120
tttccaaacc gcccctttgc cctagtggca gagacaattc acaaacacag ccctttaaaa       180
aggcttaggg atcactaagg ggatttctag aagagcgacc cgtaatccta agtatttaca       240
agacgaggct aacctccagc gagcgtgaca gcccagggag ggtgcgaggc ctgttcaaat       300
gctagctcca taaataaagc aatttcctcc ggcagtttct gaaagtagga aaggttacat       360
ttaaggttgc gtttgttagc atttcagtgt ttgccgacct cagctacagc atccctgcaa       420
ggcctcggga gacccagaag tttctcgccc cttagatcca aacttgagca acccggagtc       480
tggattcctg ggaagtc                                                      497

<210> SEQ ID NO 23
<211> LENGTH: 425
<212> TYPE: DNA
<213> ORGANISM: Mus sp.
<220> FEATURE:
<223> OTHER INFORMATION: Mouse TERT promoter

<400> SEQUENCE: 23
caagtgtgca ccaccatgcc ccgcgatatt cttattttg agactgtttt ctatgctggt         60
ttctttgggg aactacacta aggtagcttc attgttggca taaatttctc agttcaggcc       120
catatctcct aagtagcaga actaagcaaa tctcaaacaa accctcaaa aagactgatg        180 tccactaaac ggacttctaa aatagctcct gtaatcctga gcatttacaa ggcggcagac       240
ctcctataag ggagtaaata tgaaaacgcg cctgttcaaa tgctaggtcg gtggatagaa       300
gcaatttcct cagaaagctg aaggcaccaa aggttatatt tgttagcatt tcagtgtttg       360
ccaaactcag ctacagtaga gatcacagat tccctatttc ccagagattc aaaattcagc       420
agccc                                                                   425
```